(12) United States Patent
Nielsen et al.

(10) Patent No.: US 6,876,780 B1
(45) Date of Patent: Apr. 5, 2005

(54) PROVIDING FOR AUTOMATED NOTE COMPLETION

(75) Inventors: Peter E. Nielsen, Gig Harbor, WA (US); Brook A. Thomson, Lakewood, WA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 627 days.

(21) Appl. No.: 10/038,472

(22) Filed: Jan. 3, 2002

Related U.S. Application Data

(60) Provisional application No. 60/261,151, filed on Jan. 16, 2001.

(51) Int. Cl.⁷ .................................................. G06K 7/00
(52) U.S. Cl. ........................ 382/312; 382/115; 382/116
(58) Field of Search ............................... 382/312, 115, 382/116; 600/22; 701/1; 719/315; 340/517

(56) References Cited

U.S. PATENT DOCUMENTS

| | | | | | |
|---|---|---|---|---|---|
| 5,682,526 | A | * | 10/1997 | Smokoff et al. | 707/104.1 |
| 6,155,603 | A | * | 12/2000 | Fox | 283/62 |
| 6,198,389 | B1 | * | 3/2001 | Buccola | 340/517 |
| 6,385,203 | B2 | * | 5/2002 | McHale et al. | 370/401 |

FOREIGN PATENT DOCUMENTS

| JP | 404057187 A | * | 2/1992 | G07D/7/00 |
|---|---|---|---|---|

OTHER PUBLICATIONS

Author Unknown, Consult Tracking, Jun. 2000, pp. 1–47.

* cited by examiner

*Primary Examiner*—Anh Hong Do
(74) *Attorney, Agent, or Firm*—Elizabeth Arwine

(57) ABSTRACT

A method and system which provide for automated note completion. In one embodiment, the method is characterized by sensing a presence of a first provider; detecting at least one incomplete provider note; and presenting the at least one incomplete provider note to the first provider. In another embodiment of the method, the sensing a presence of a first provider is characterized by accepting an identifier associated with the first provider. In another embodiment of the method, the accepting an identifier associated with the first provider is characterized by accepting user input of the identifier via either a keyboard, a touch-screen reader, a graphical user interface, or a biometrics identifier. In another embodiment of the method, the detecting at least one incomplete provider note is characterized by checking at least one database for flagged-incomplete notes associated with the at least one provider. In one or more various embodiments, related systems include but are not limited to circuitry and/or programming for effecting the foregoing-referenced method embodiments; the circuitry and/or programming can be virtually any combination of hardware, software, and/or firmware configured to effect the foregoing-referenced method embodiments depending upon the design choices of the system designer.

10 Claims, 55 Drawing Sheets

2650

2652

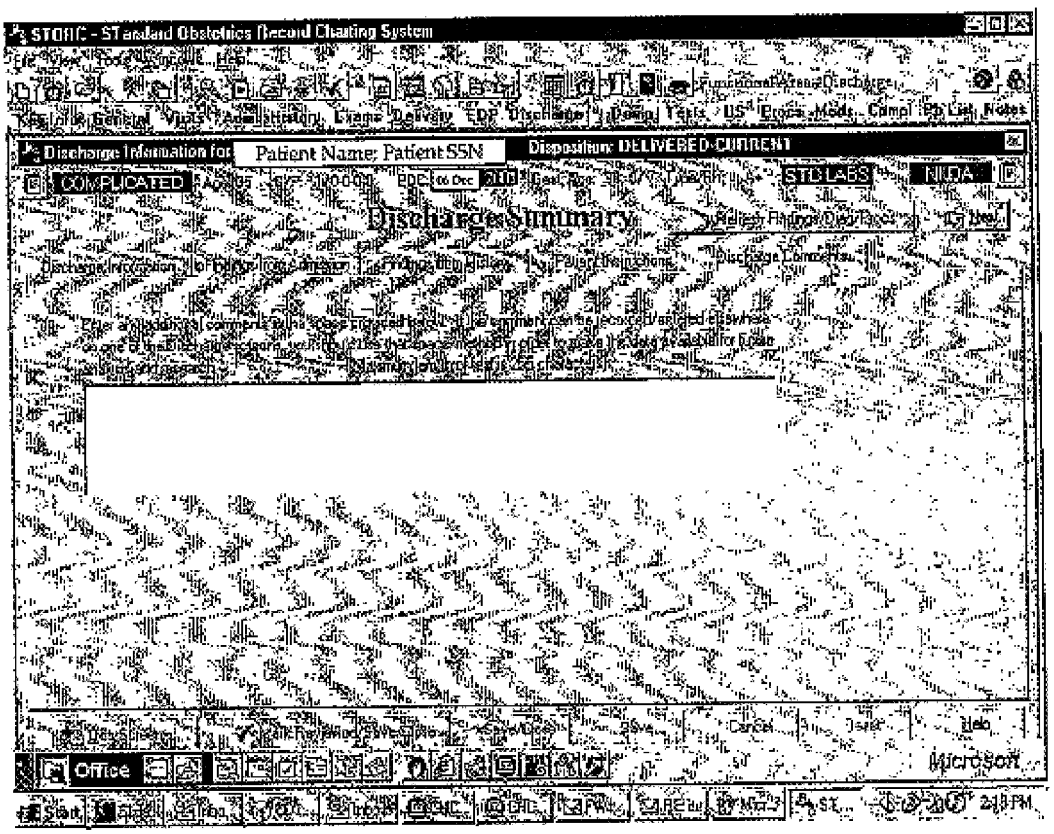
33E

PROVIDING FOR AUTOMATED NOTE COMPLETION

CROSS-REFERENCE TO RELATED APPLICATION

This patent application incorporates by reference in its entirety the subject matter of the currently co-pending U.S. Provisional Patent Application No. 60/261,151, filed 16 Jan. 2001, entitled, STANDARD OBSTETRIC RECORD CHARTING SYSTEM (STORC): ELECTRONIC OBSTETRIC RECORD, naming Dr. Peter E. Nielsen and Dr. Brook A. Thomson as inventors, filed substantially contemporaneously herewith.

This patent application incorporates by reference in its entirety the subject matter of the currently co-pending U.S. Patent Application entitled, STANDARDIZED INPATIENT-OUTPATIENT NOMENCLATURES AND ACCEPTING BOTH OUTPATIENT AND INPATIENT DATA TO COMMONLY ACCESSIBLE STORAGE, naming Dr. Peter E. Nielsen and Dr. Brook A. Thomson as inventors, filed substantially contemporaneously herewith.

This patent application incorporates by reference in its entirety the subject matter of the currently co-pending U.S. Patent Application entitled, PROVIDING OUTPATIENT AND INPATIENT DATA ACROSS OUTPATIENT AND INPATIENT FACILITIES AND PROVIDING AUTOMATED DISCHARGE SUMMARY NARRATION, naming Dr. Peter E. Nielsen and Dr. Brook A. Thomson as inventors, filed substantially contemporaneously herewith.

This patent application incorporates by reference in its entirety the subject matter of the currently co-pending U.S. Patent Application entitled, COLLECTING COUNTERSIGNATURES, naming Dr. Peter E. Nielsen and Dr. Brook A. Thomson as inventors, filed substantially contemporaneously herewith.

This patent application incorporates by reference in its entirety the subject matter of the currently co-pending U.S. Patent Application entitled, PROVIDING A SUGGESTED COURSE OF TREATMENT, naming Dr. Peter E. Nielsen and Dr. Brook A. Thomson as inventors, filed substantially contemporaneously herewith.

STATEMENT REGARDING FEDERALLY SPONSORED RESEARCH OR DEVELOPMENT

This invention was made with government support provided by the United States Army. The government has certain rights in this invention.

BACKGROUND OF THE INVENTION

1. Field of the Invention

The present application relates, in general, to methods and systems which support the practice of medicine.

2. Description of the Related Art

The practice of medicine is inherently difficult, due to many factors. One difficulty that exists in the practice of medicine is making sure that various health care providers (e.g., nurse practitioners, intern physicians, resident physicians, general practice physicians, and specialist physicians) associated with a particular patient's care are privy to information relevant to the care and treatment of the particular patient.

The inventors named herein have devised several methods and systems which support the practice of medicine. The several methods and systems which support the practice of medicine are described following.

BRIEF SUMMARY OF THE INVENTION

The inventors have devised a method and system which provide for automated note completion. In one embodiment, the method is characterized by sensing a presence of a first provider; detecting at least one incomplete provider note; and presenting the at least one incomplete provider note to the first provider.

In another embodiment of the method, the sensing a presence of a first provider is characterized by accepting an identifier associated with the first provider.

In another embodiment of the method, the accepting an identifier associated with the first provider is characterized by accepting user input of the identifier via either a keyboard, a touch-screen reader, a graphical user interface, or a biometrics identifier.

In another embodiment of the method, the detecting at least one incomplete provider note is characterized by checking at least one database for flagged-incomplete notes associated with the at least one provider.

In one or more various embodiments, related systems include but are not limited to circuitry and/or programming for effecting the foregoing-referenced method embodiments; the circuitry and/or programming can be virtually any combination of hardware, software, and/or firmware configured to effect the foregoing-referenced method embodiments depending upon the design choices of the system designer.

The foregoing is a summary and thus contains, by necessity; simplifications, generalizations and omissions of detail; consequently, those skilled in the art will appreciate that the summary is illustrative only and is NOT intended to be in any way limiting. Other aspects, inventive features, and advantages of the devices and/or processes described herein, as defined solely by the claims, will become apparent in the non-limiting detailed description set forth herein.

BRIEF DESCRIPTION OF THE SEVERAL VIEWS OF THE DRAWING(S)

Figure 7:
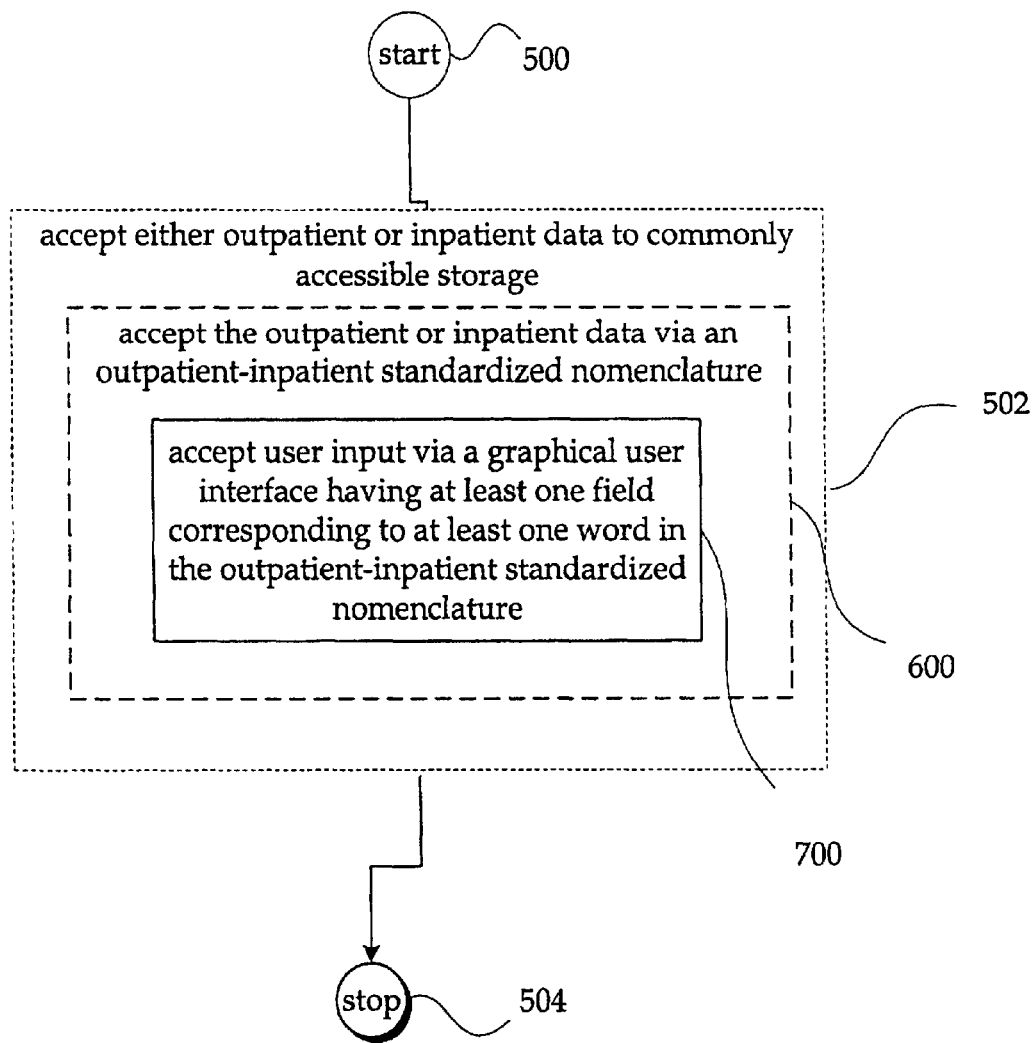
FIG. 7 illustrates a graphical user interface depicting an example of the implementation illustrated in method step 600.
Figure 7A:
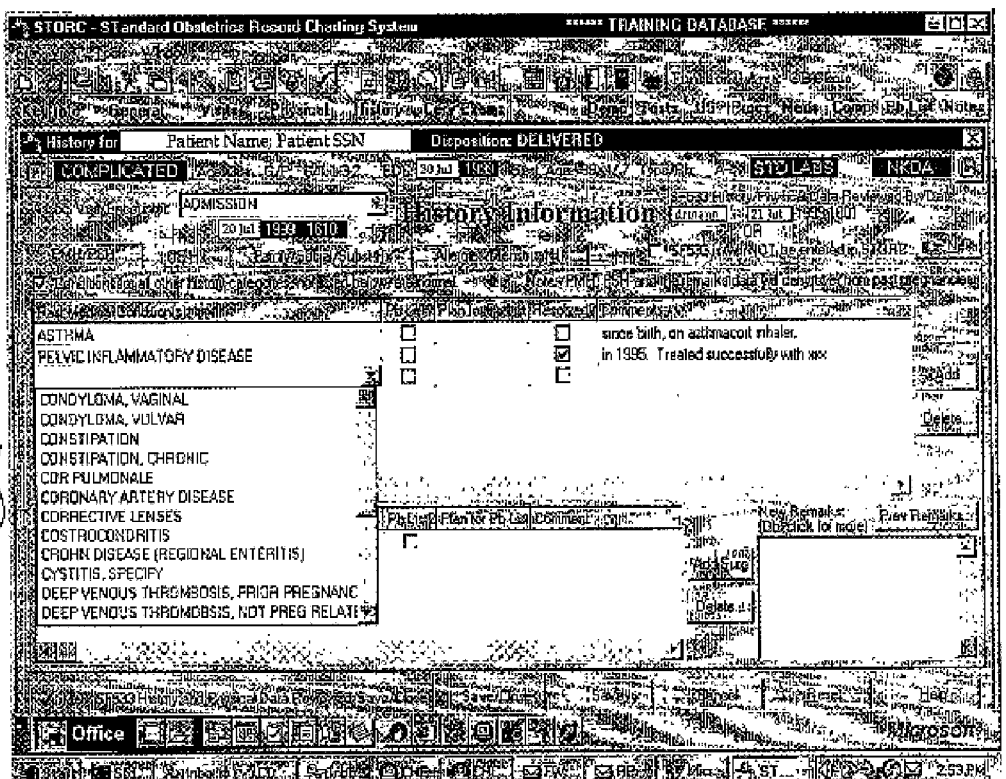
FIG. 7A illustrates a GUI used in one implementation of method step 600.
Figure 7B:
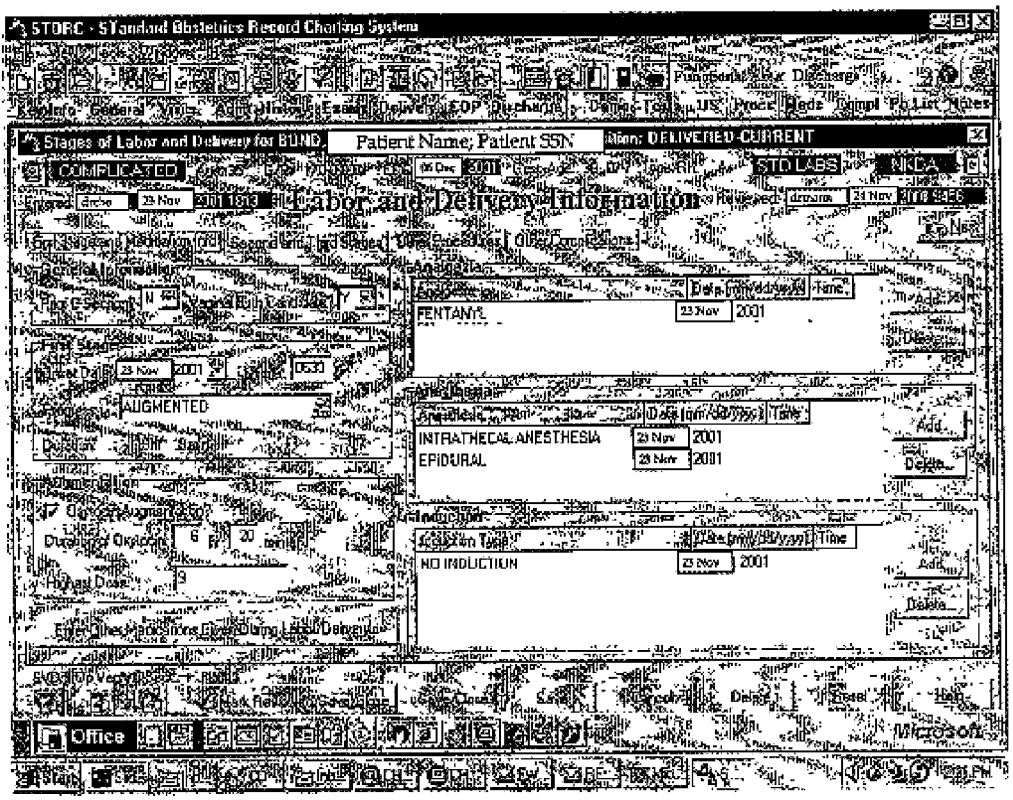
FIG. 7B depicts a labor and delivery information GUI which is used to acquire labor and delivery information as shown in FIG. 7B (in addition, in one implementation, an automated Narrative Summary culls database information gathered at least in part from the GUI shown in FIG. 7B.
Figure 7C:
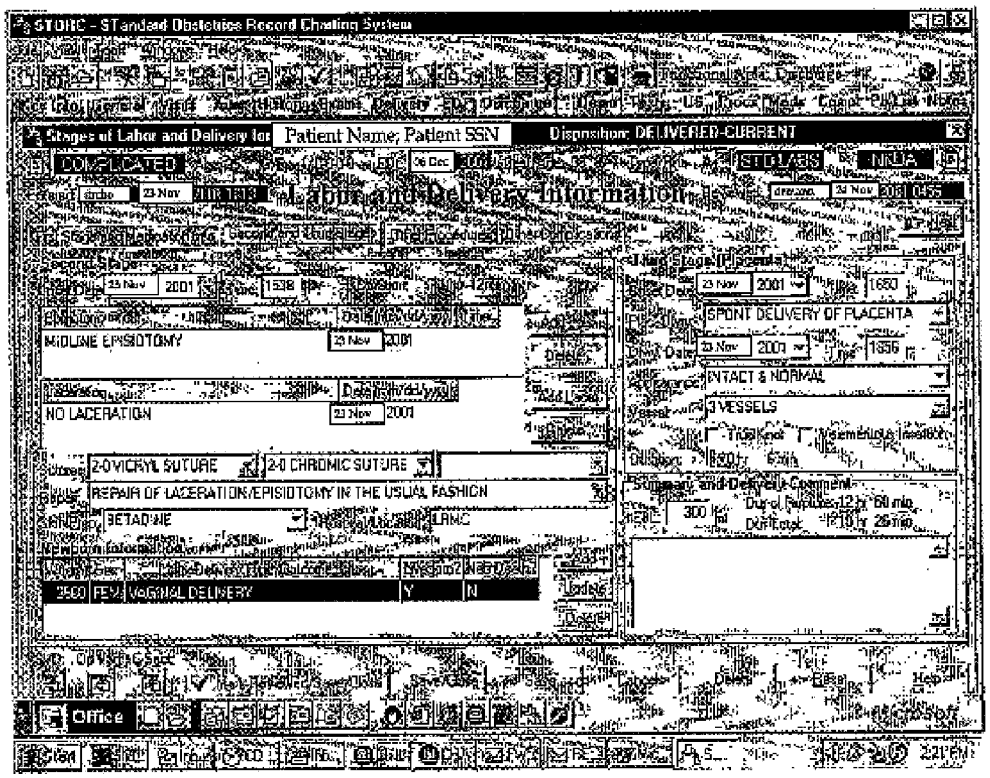
FIG. 7C depicts another labor and delivery GUI analogous to FIG. 7A.
Figure 7D:
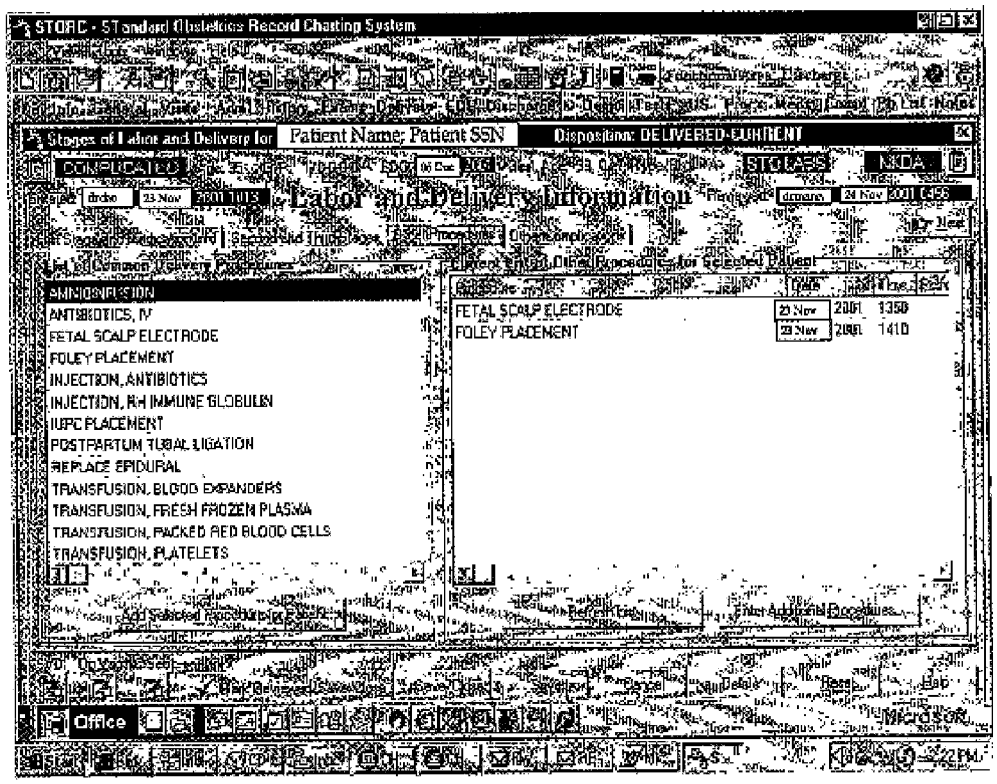
Figure 7E:
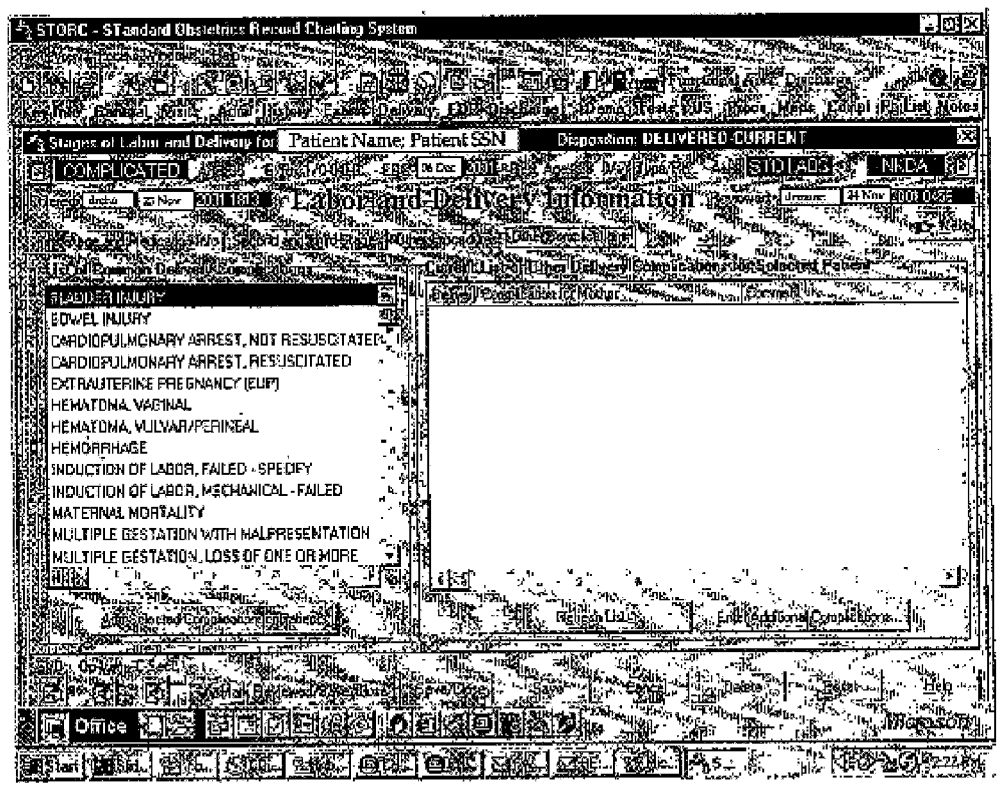

FIGS. 7D–E shows two GUIs respectively having a procedure and a complication "picklist."

Figure 6:
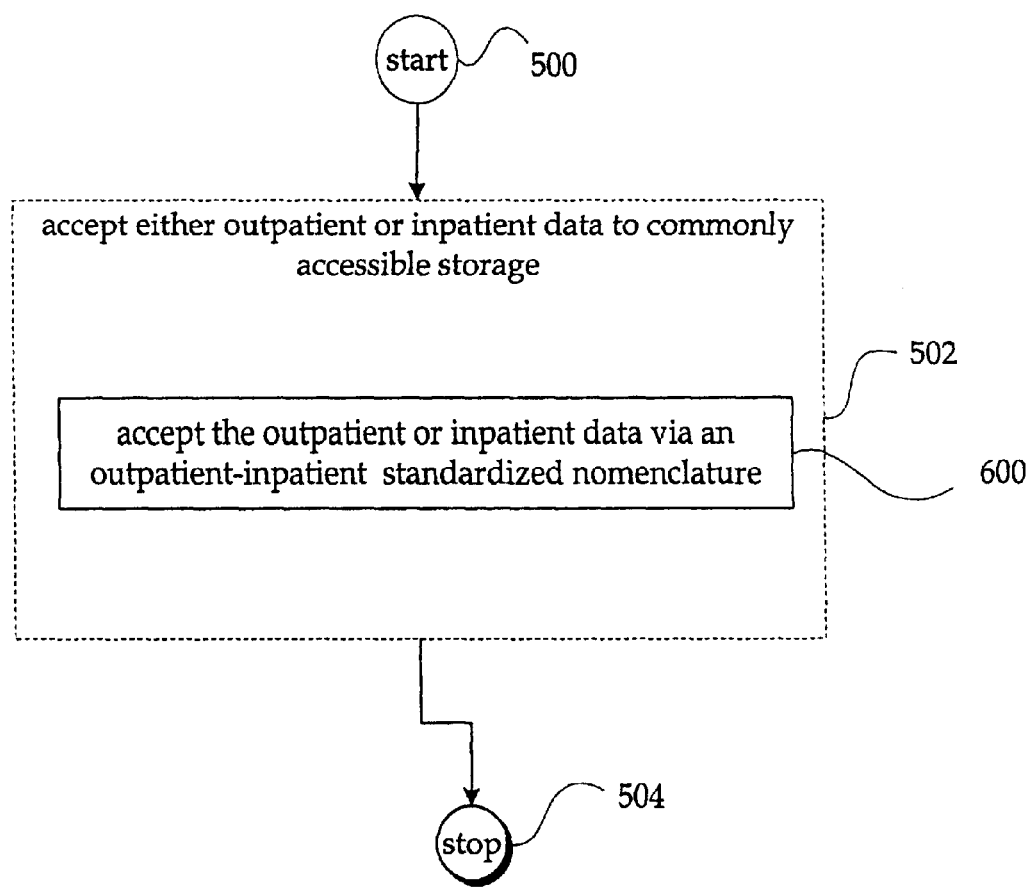
FIG. 6 depicts a high-level logic flowchart depicting an alternate implementation of the process shown in FIG. 5.
Figure 8:
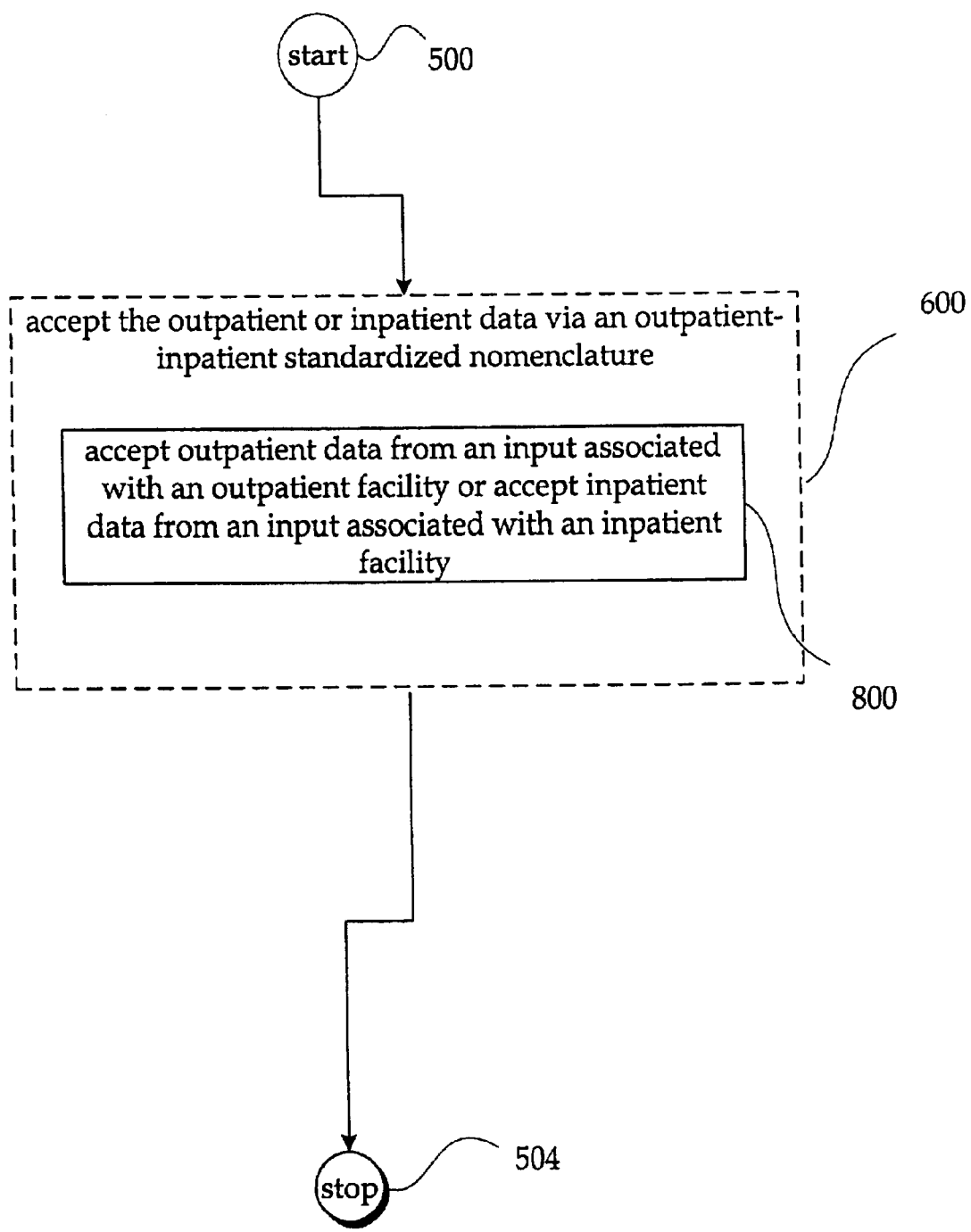

FIG. 8 depicts a high-level logic flowchart depicting an alternate implementation of the process shown in FIG. 6.

Figure 9:
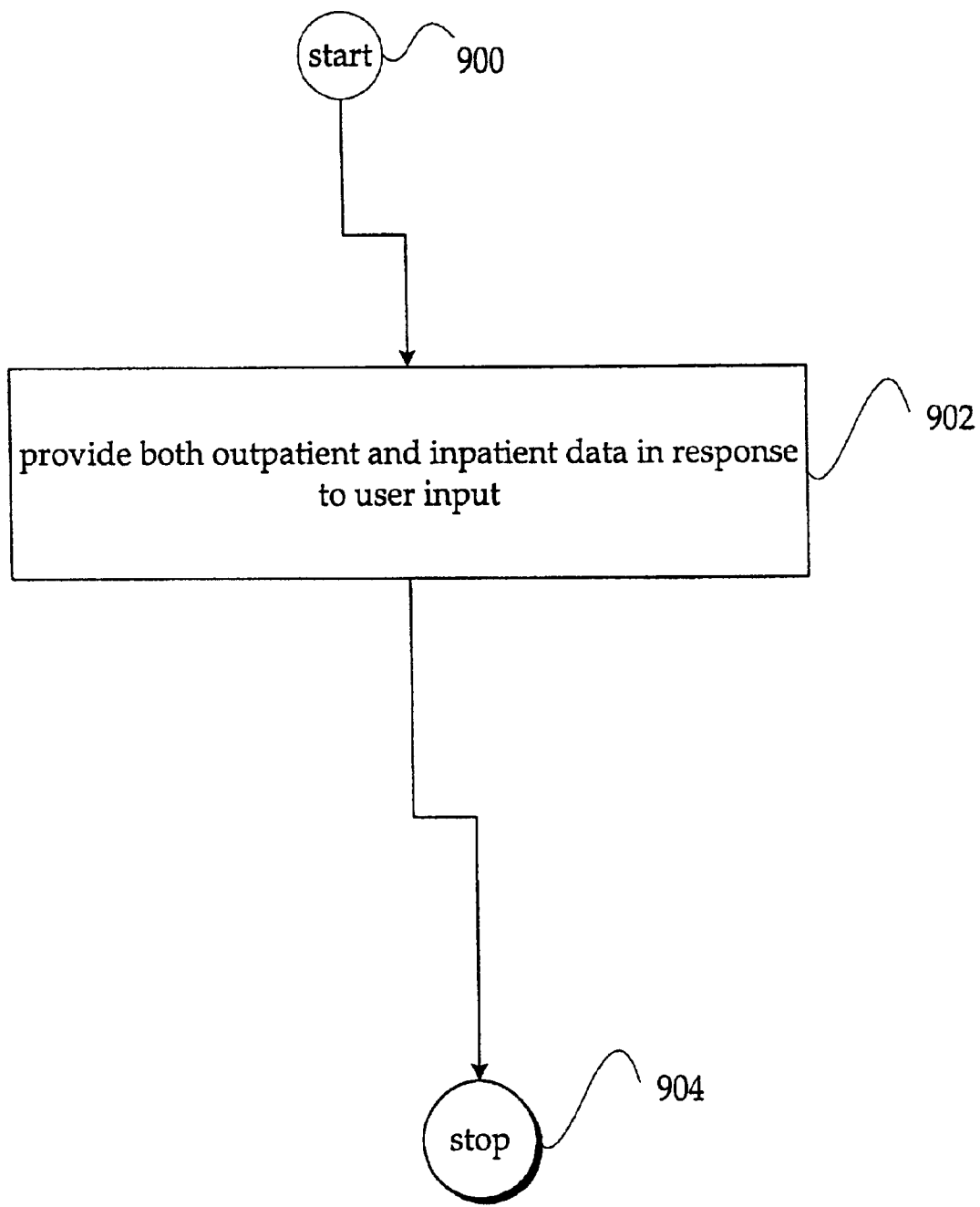

FIG. 9 shows a high-level logic flowchart depicting a process.

Figure 10:
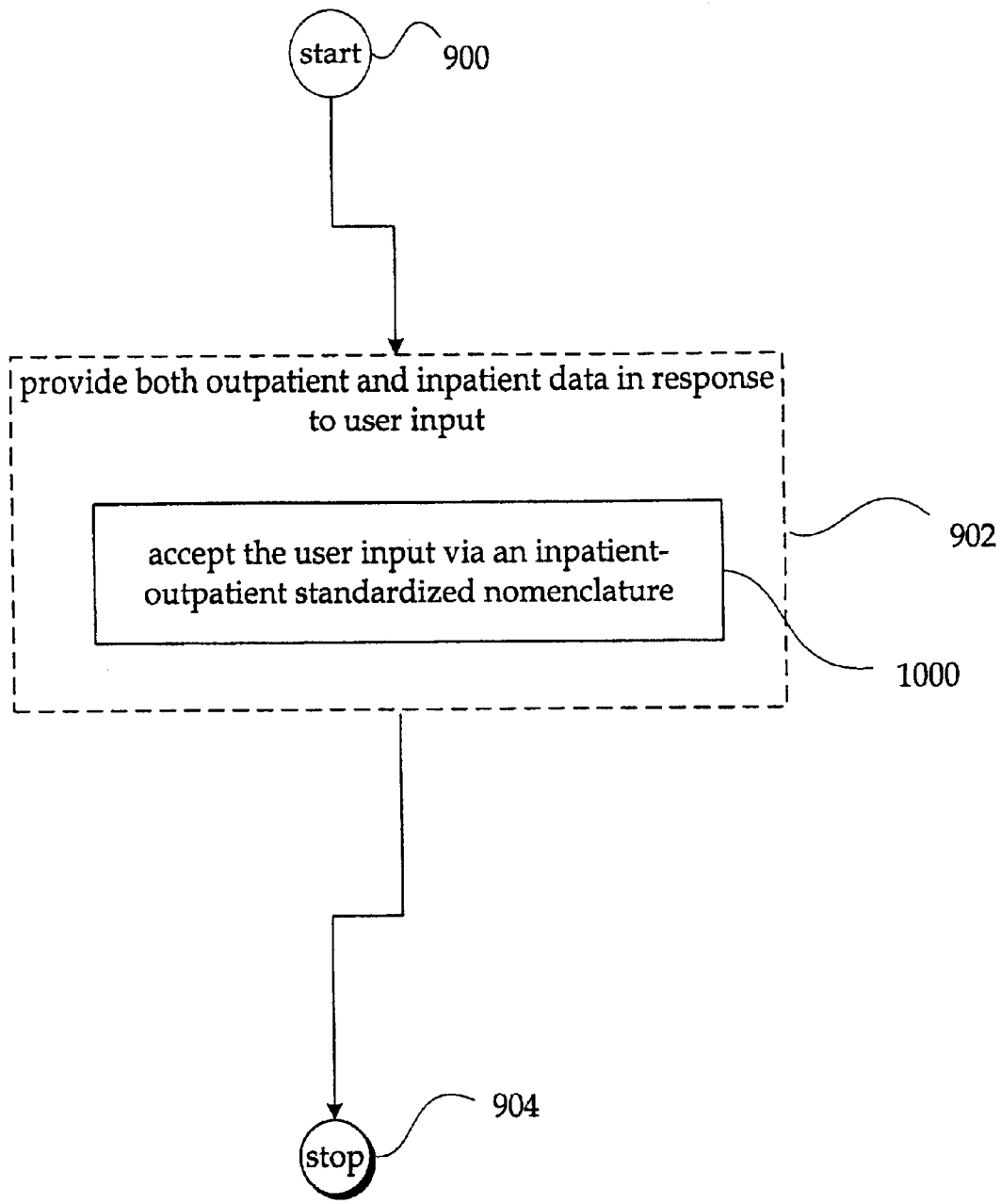

FIG. 10 depicts a high-level logic flowchart depicting an alternate implementation of the process shown in FIG. 9.

Figure 11:
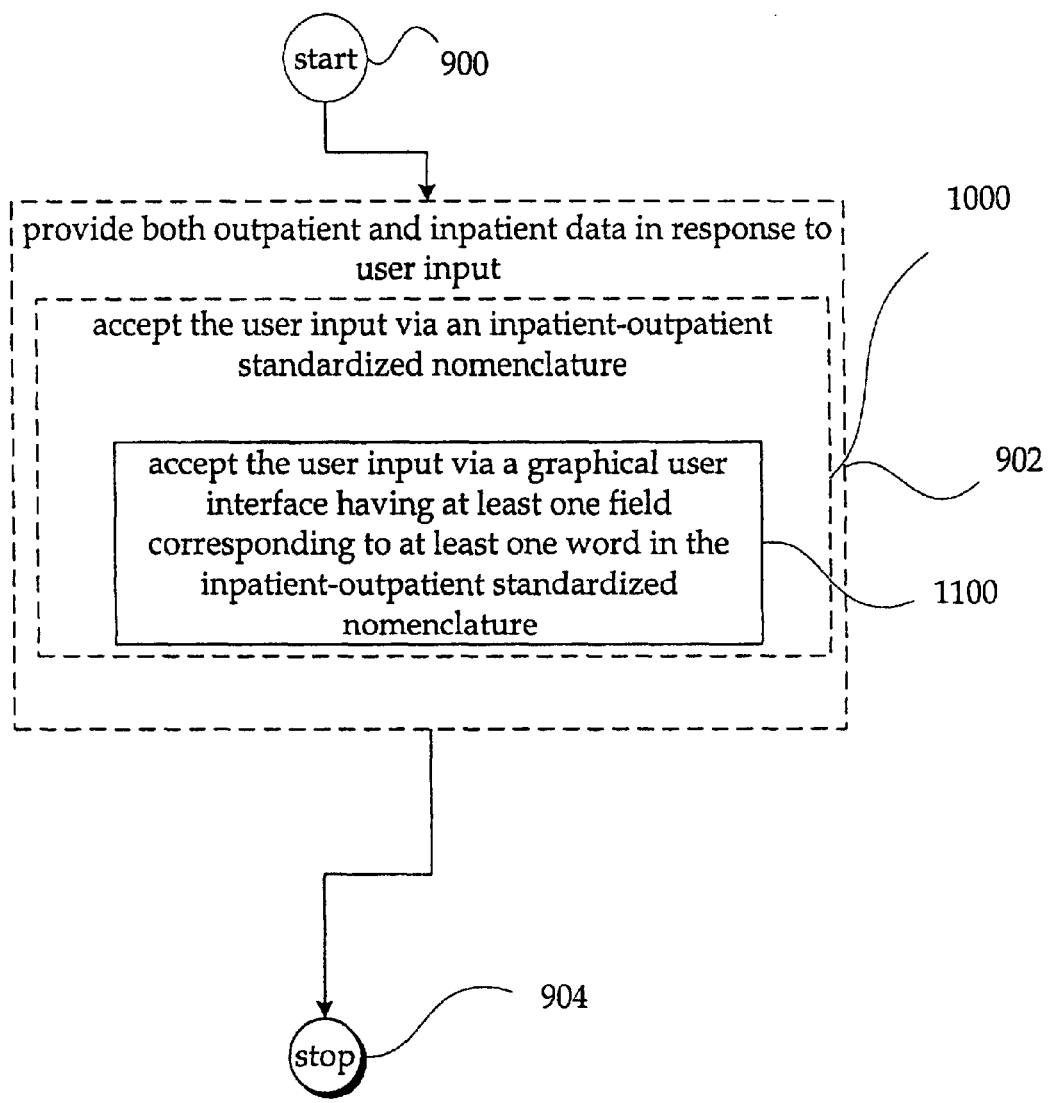

FIG. 11 depicts a high-level logic flowchart depicting an alternate implementation of the process shown in FIG. 9.

Figure 12:
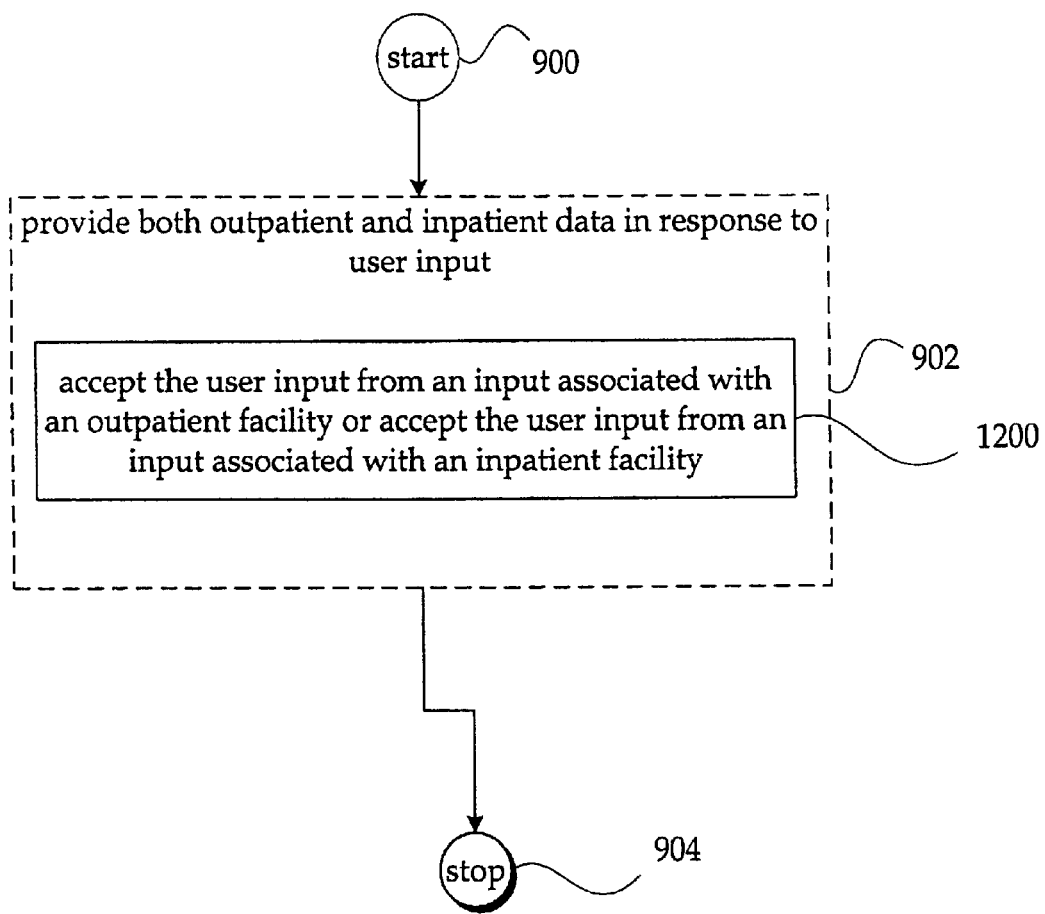

FIG. 12 depicts a high-level logic flowchart depicting an alternate implementation of the process shown in FIG. 9.

Figure 13:
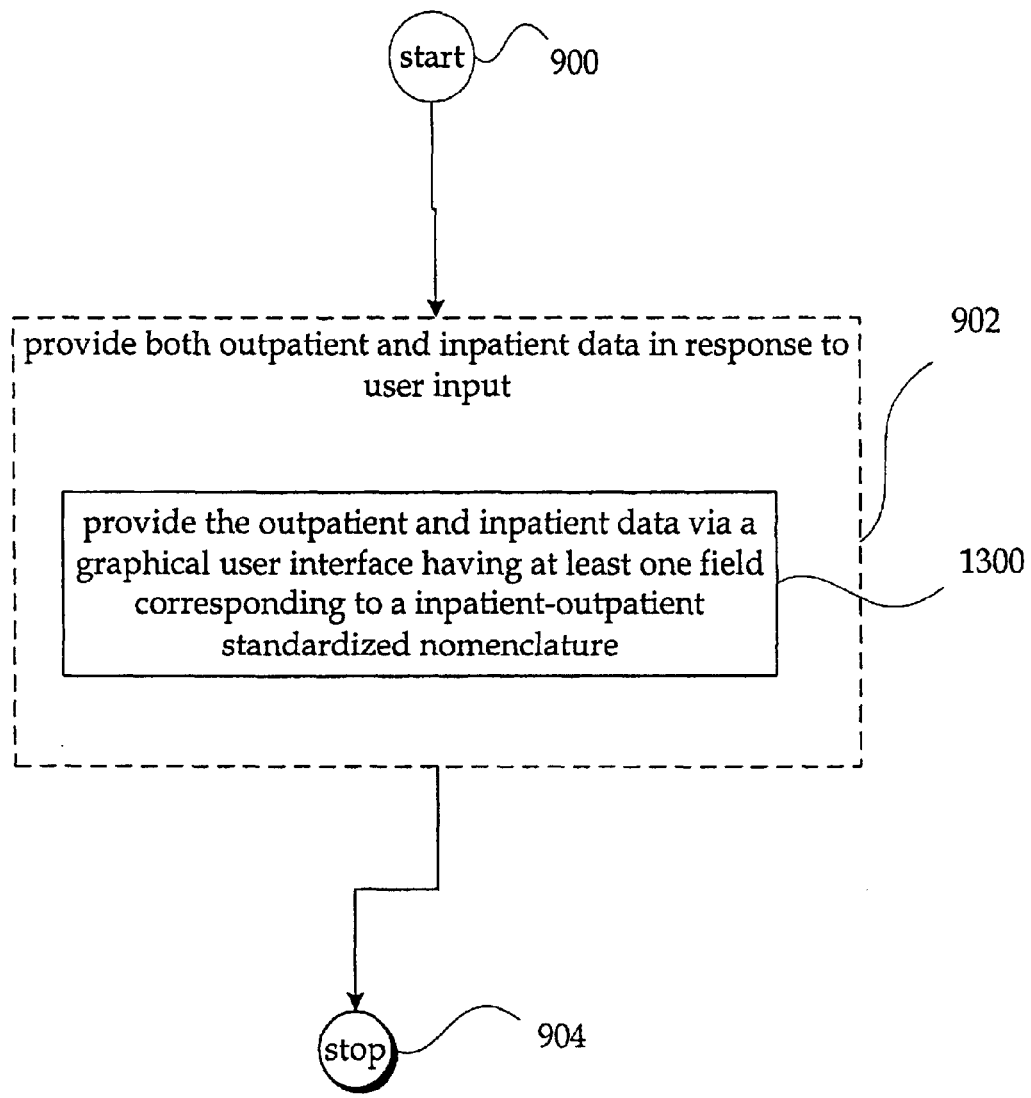

FIG. 13 illustrates a user interface depicting an alternative of the implementation illustrated in method step 900.

Figure 14:
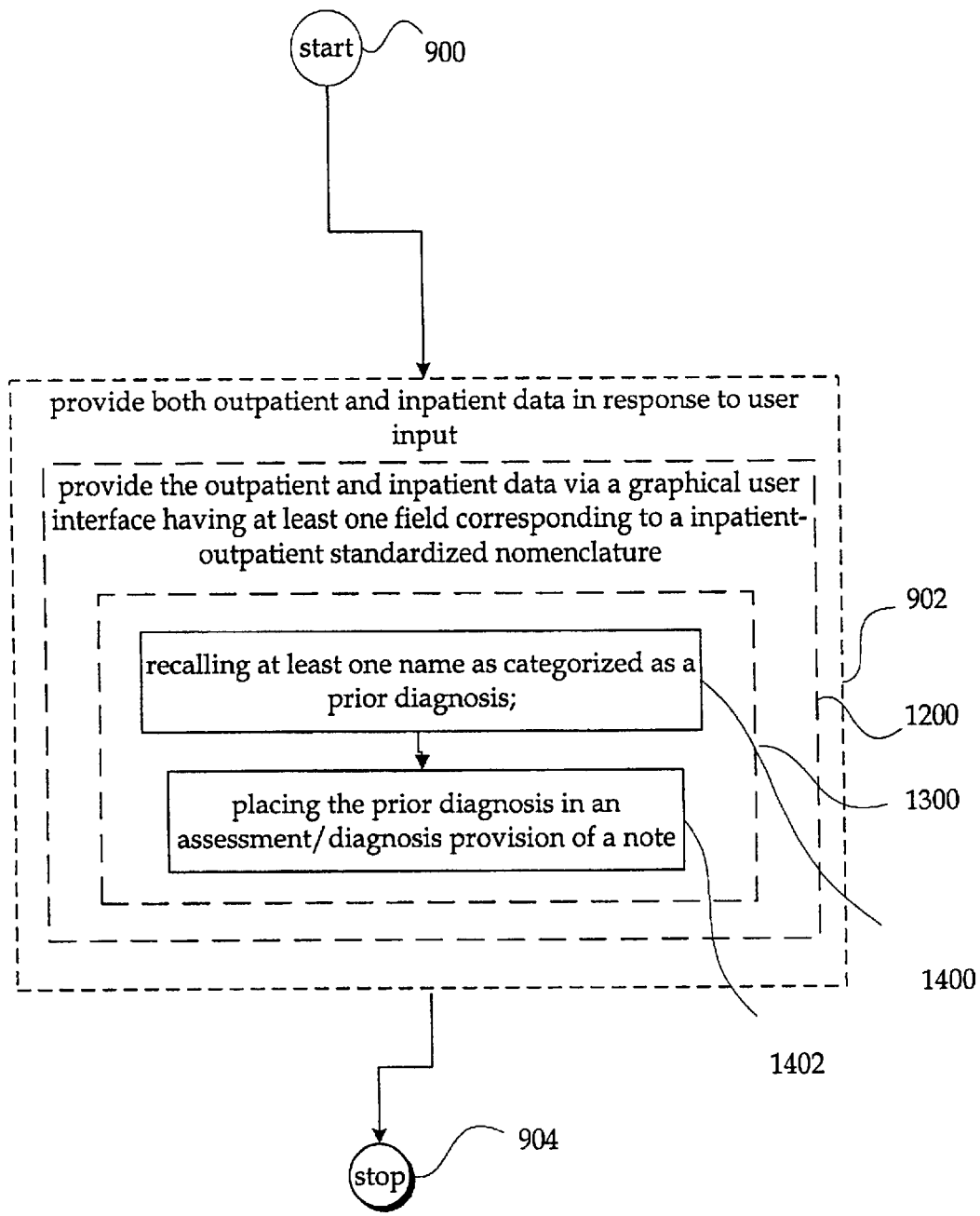

FIG. 14 depicts a high-level logic flowchart depicting an alternate implementation of the process shown in FIG. 13.

Figure 14A:
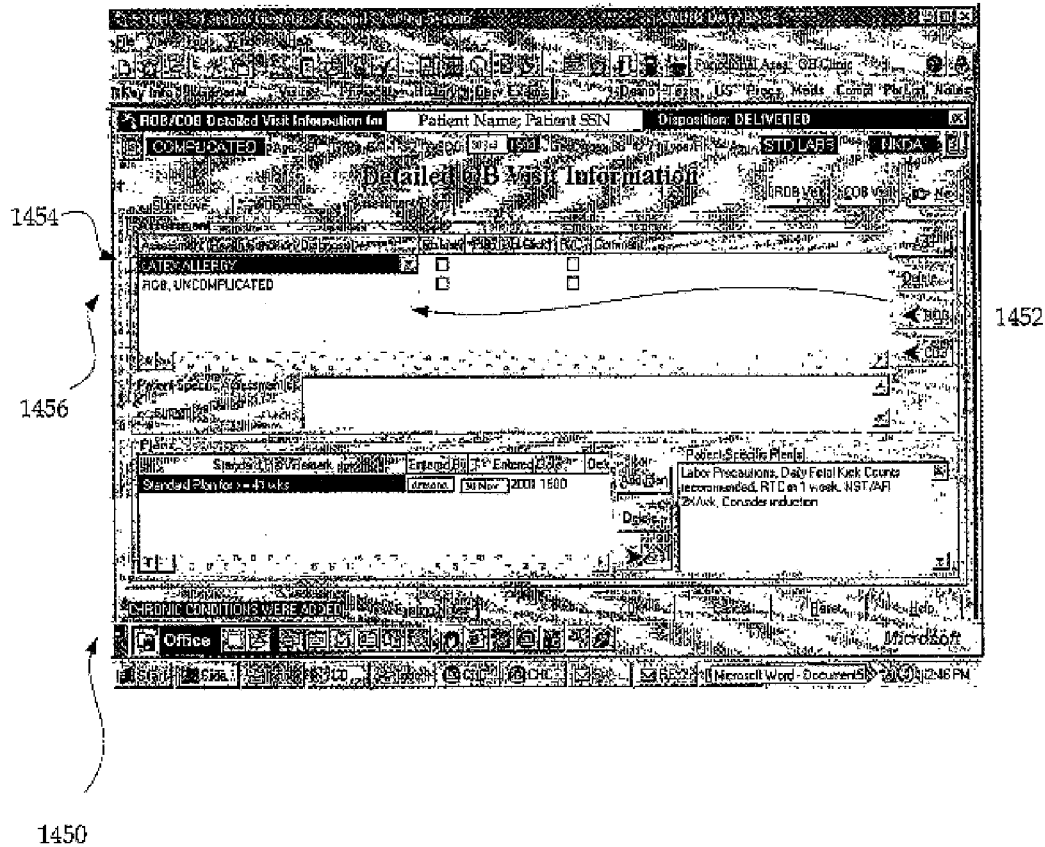

FIG. 14A illustrates a GUI used in one implementation of method step 1402.

Figure 15:
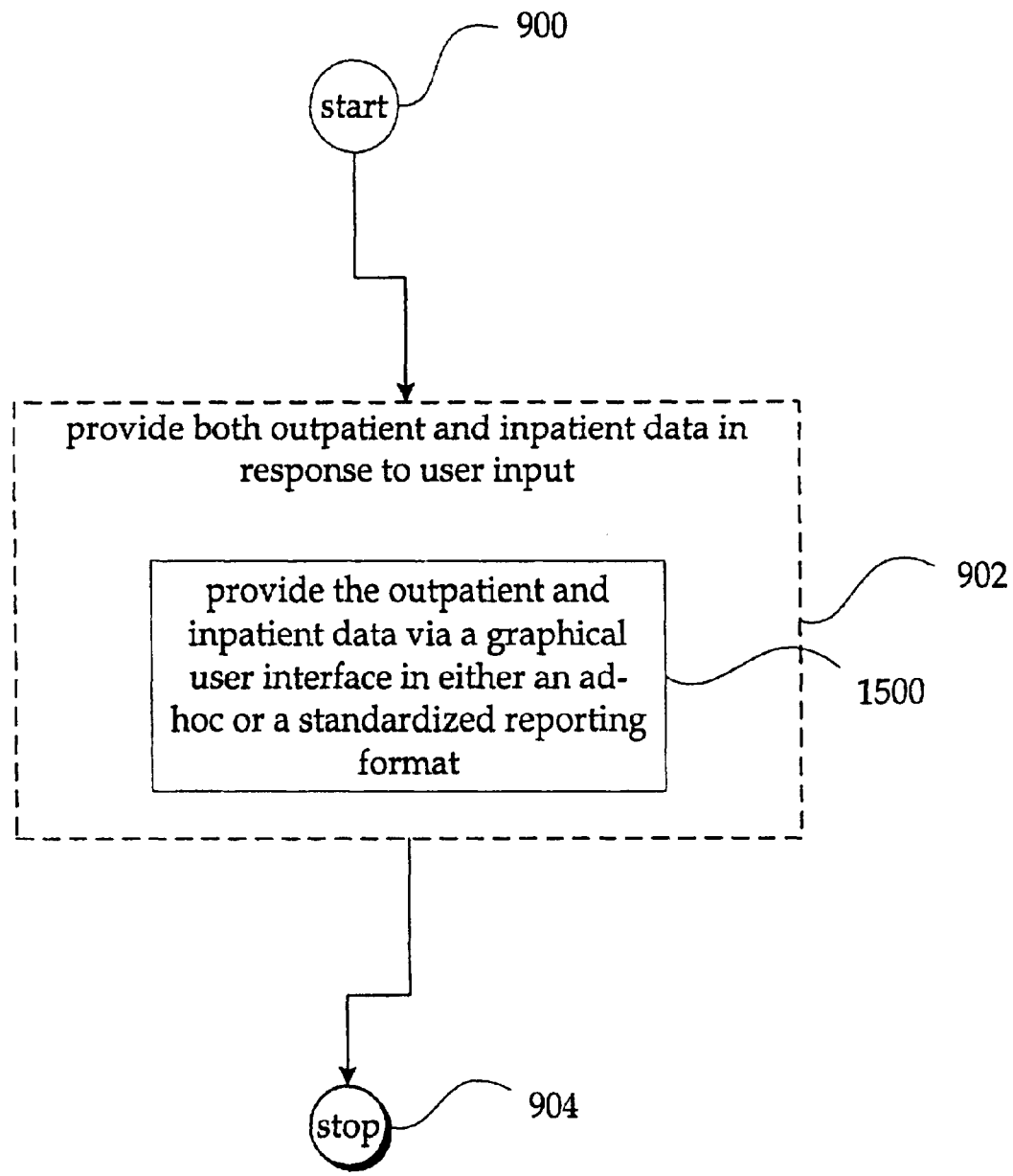

FIG. 15 depicts a high-level logic flowchart depicting an alternate implementation of the process shown in FIG. 9.

Figure 15A:
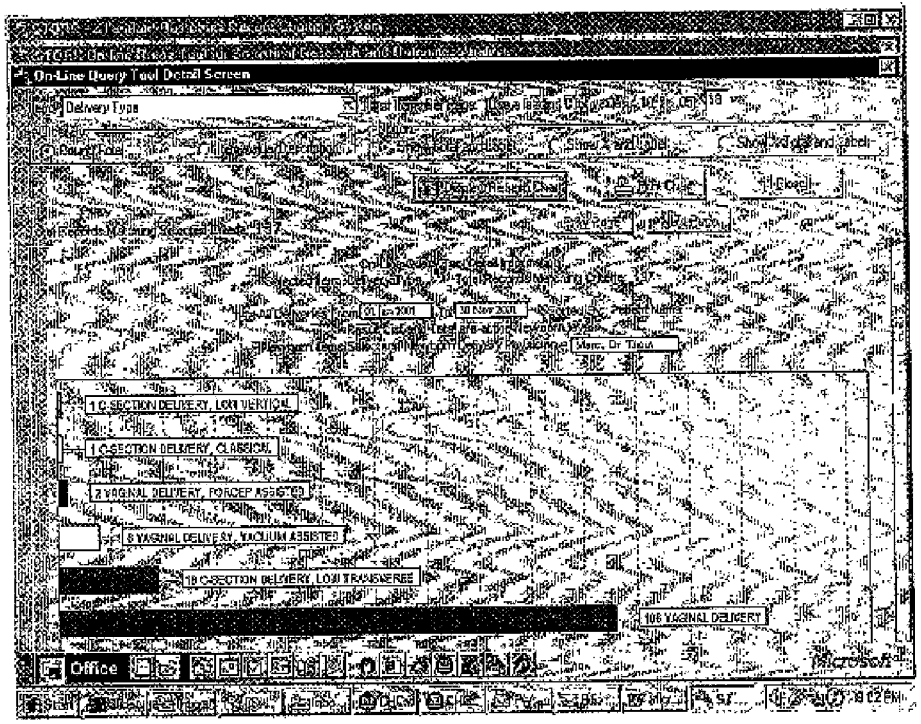

FIG. 15A illustrates a GUI used in one implementation of method step 1500.

Figure 15B:
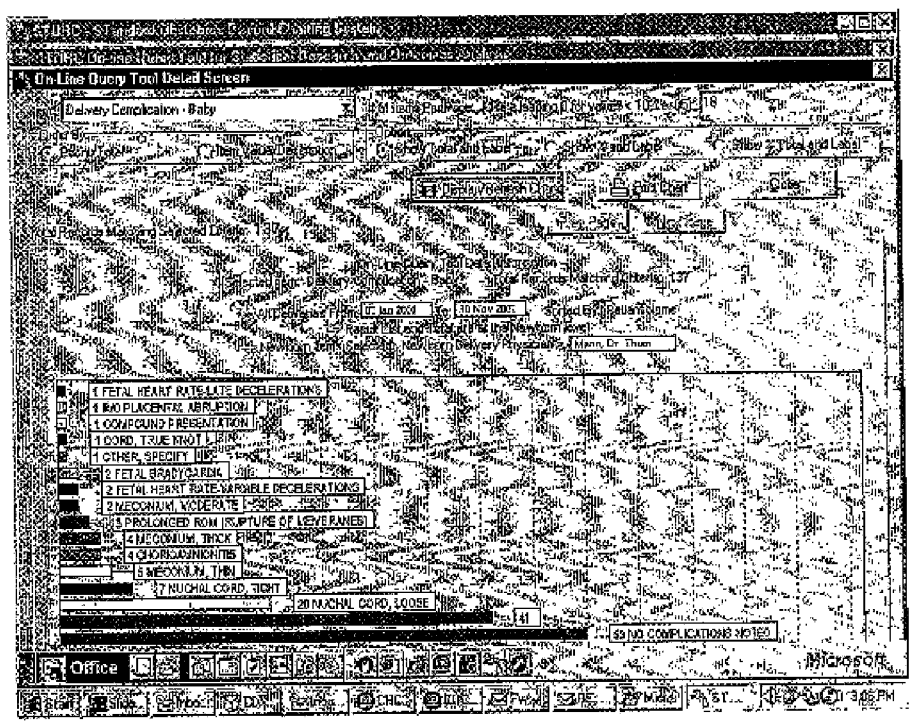

FIG. 15B shows a GUI 1570 which depicts a GUI used in another ad hoc reporting screen 1572 implementation of method step 1500.

Figure 15C:
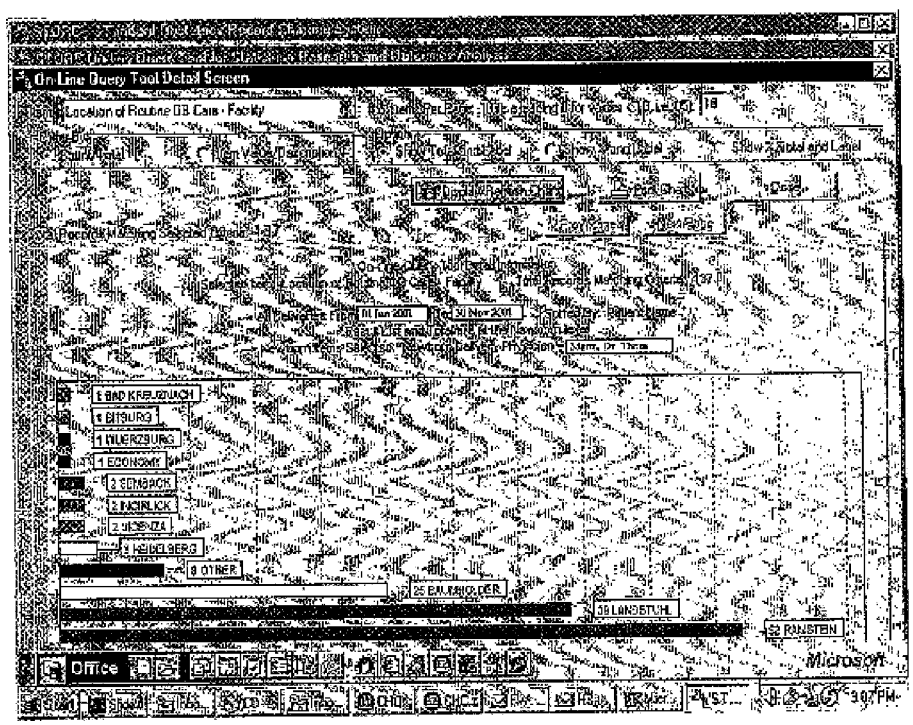

FIG. 15C shows a GUI 1580 which depicts a GUI used in another ad hoc reporting screen 1582 implementation of method step 1500; ad hoc reporting screen 1582 shows an administrative data implementation in that it lists the outpatient facilities from which inpatients originated (e.g., German cites in which the outpatients were treated).

Figure 16:
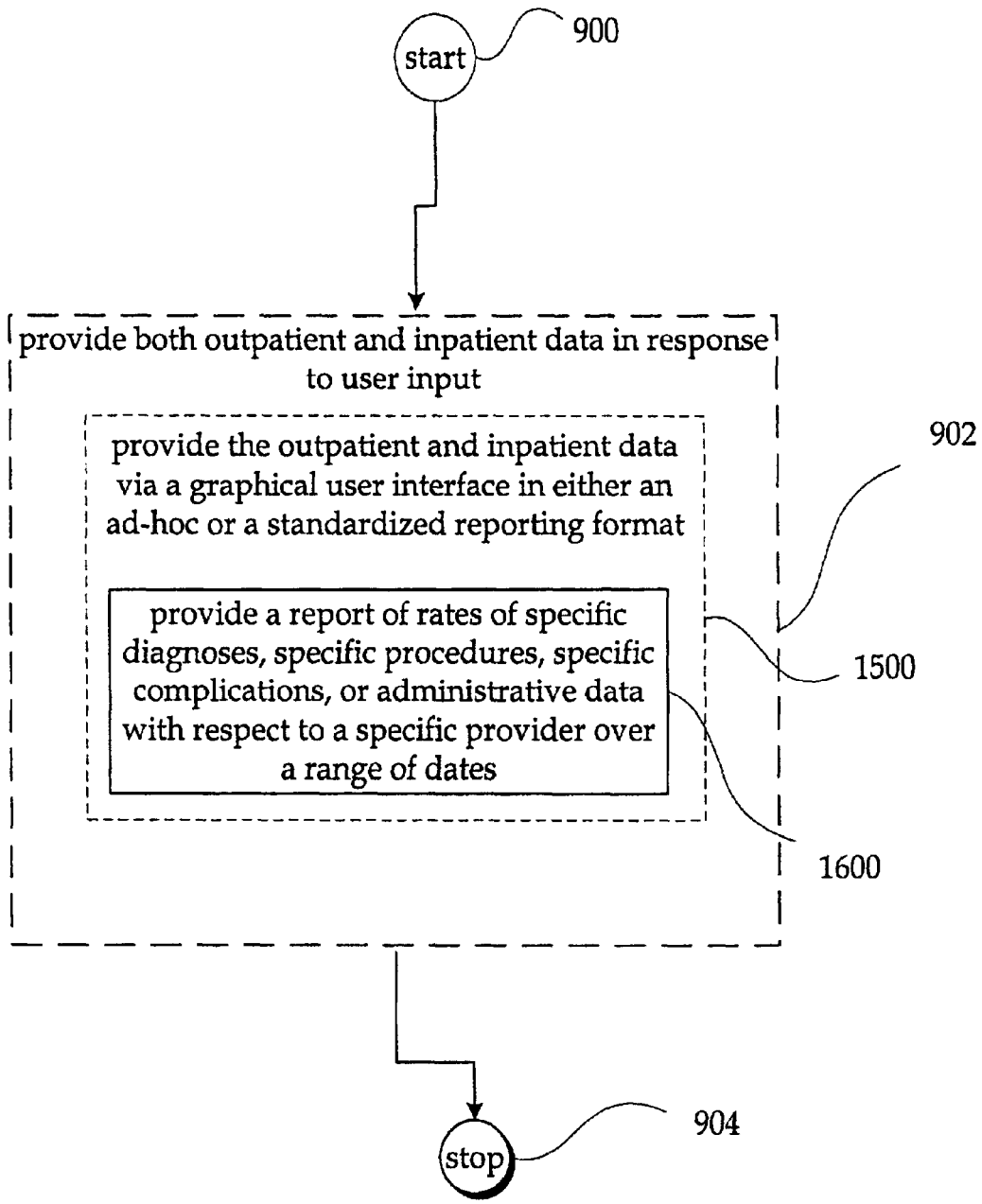

FIG. 16 depicts a high-level logic flowchart depicting an alternate implementation of the process shown in FIG. 15.

Figure 17:
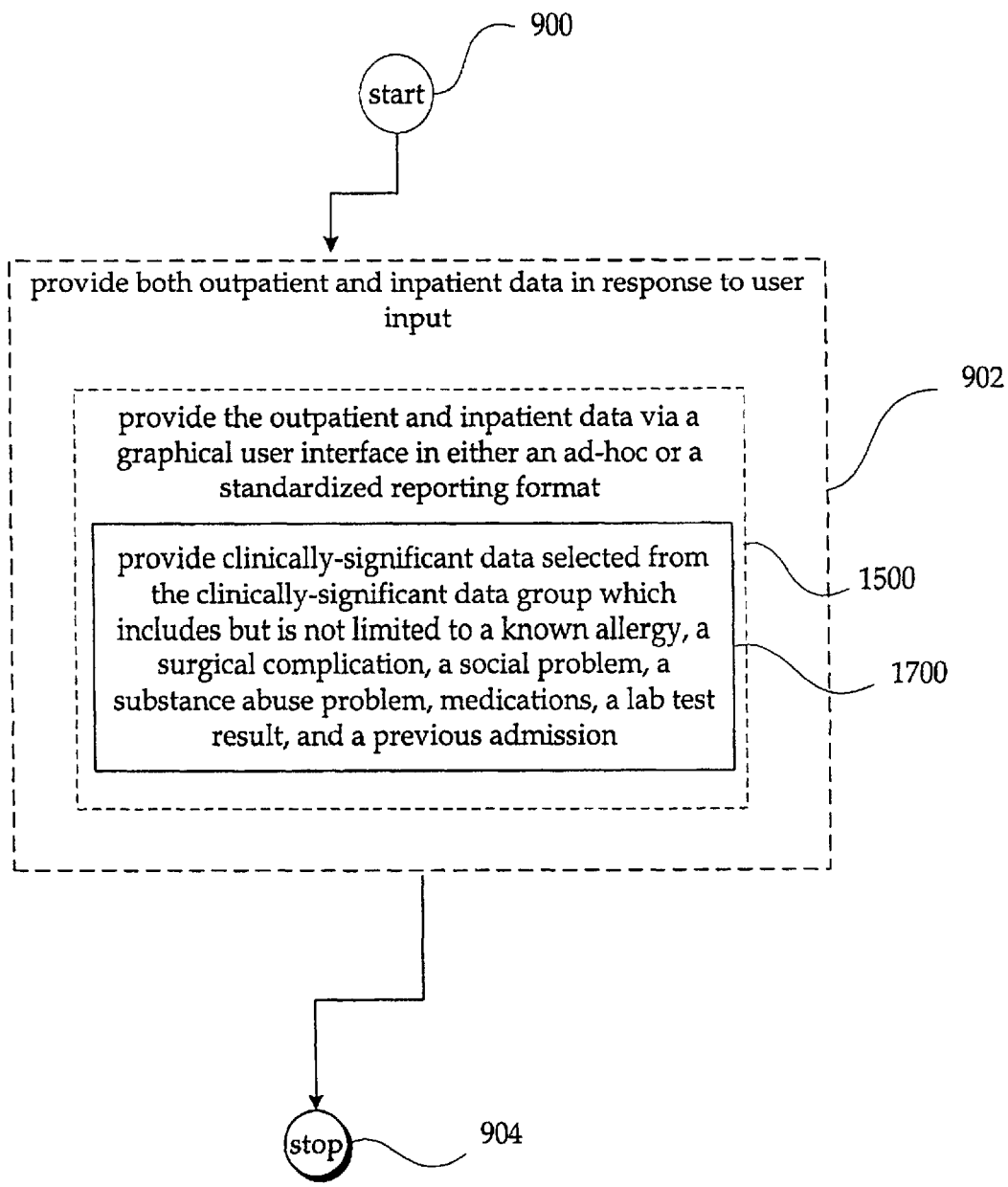

FIG. 17 illustrates graphical user interface depicting an example of the implementation illustrated in method step 15.

Figure 18:
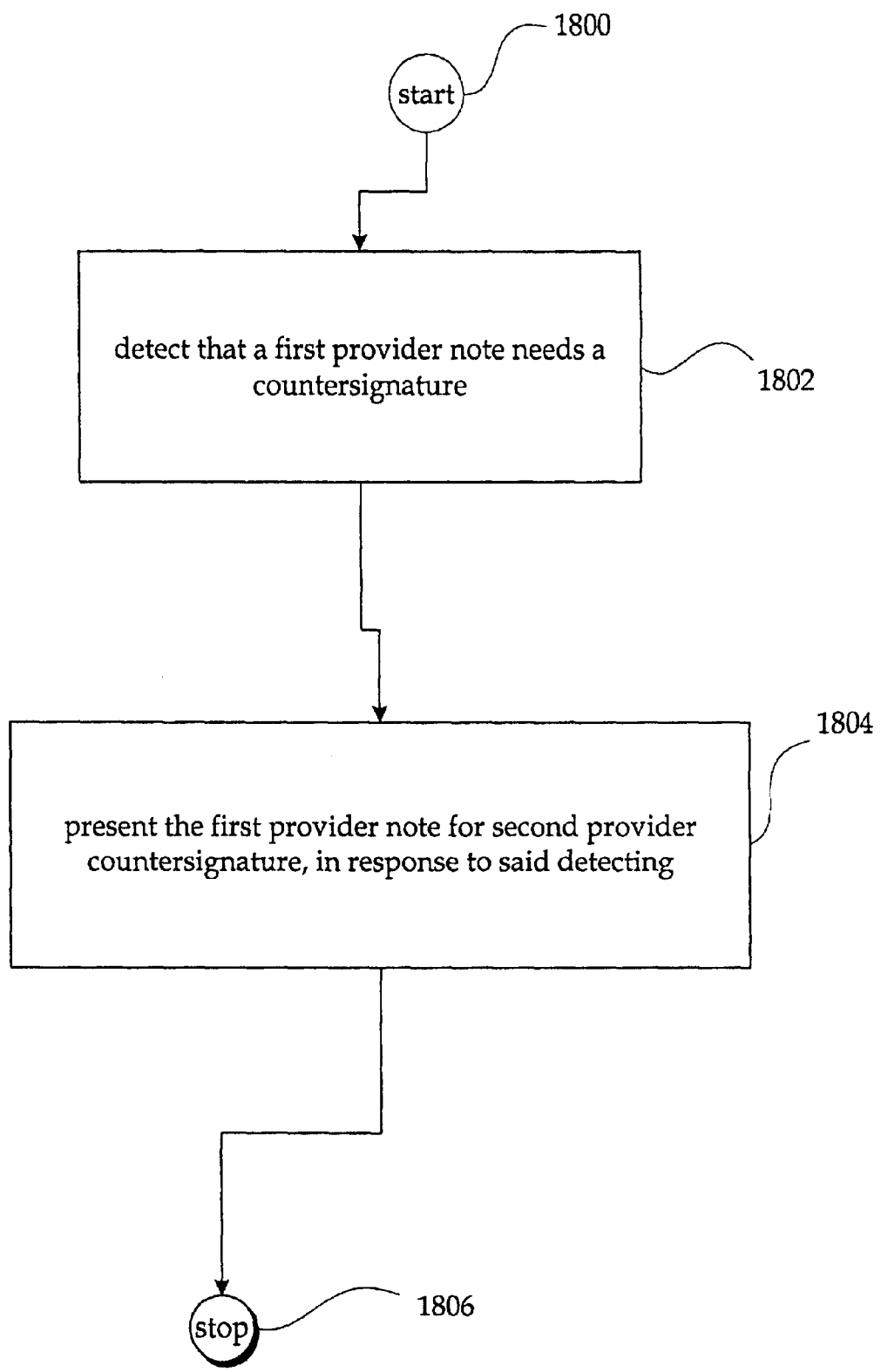

FIG. 18 shows a high-level logic flowchart depicting a process.

Figure 19:
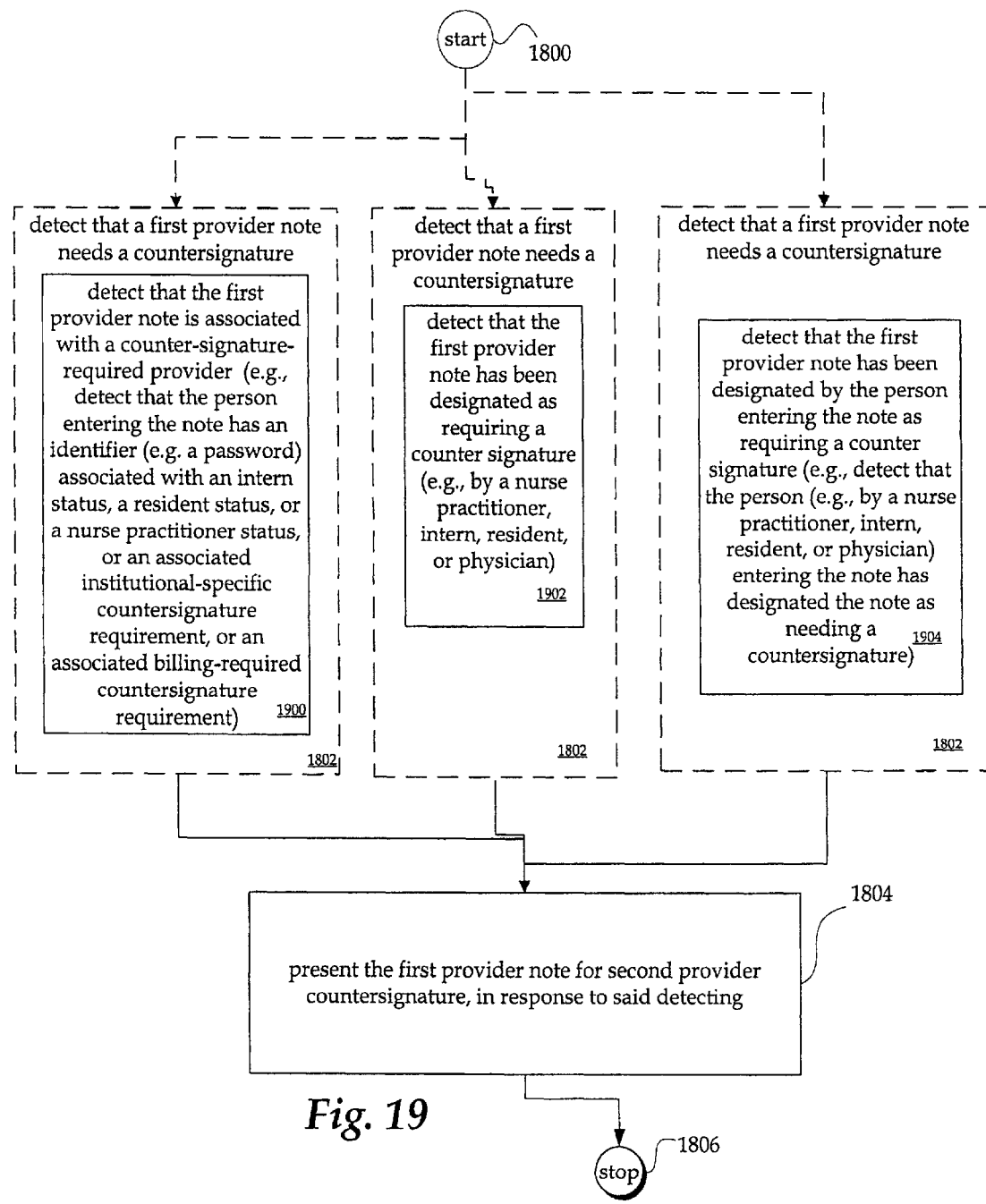

FIG. 19 depicts a high-level logic flowchart depicting alternate implementations of the process shown in FIG. 18.

Figure 19A:
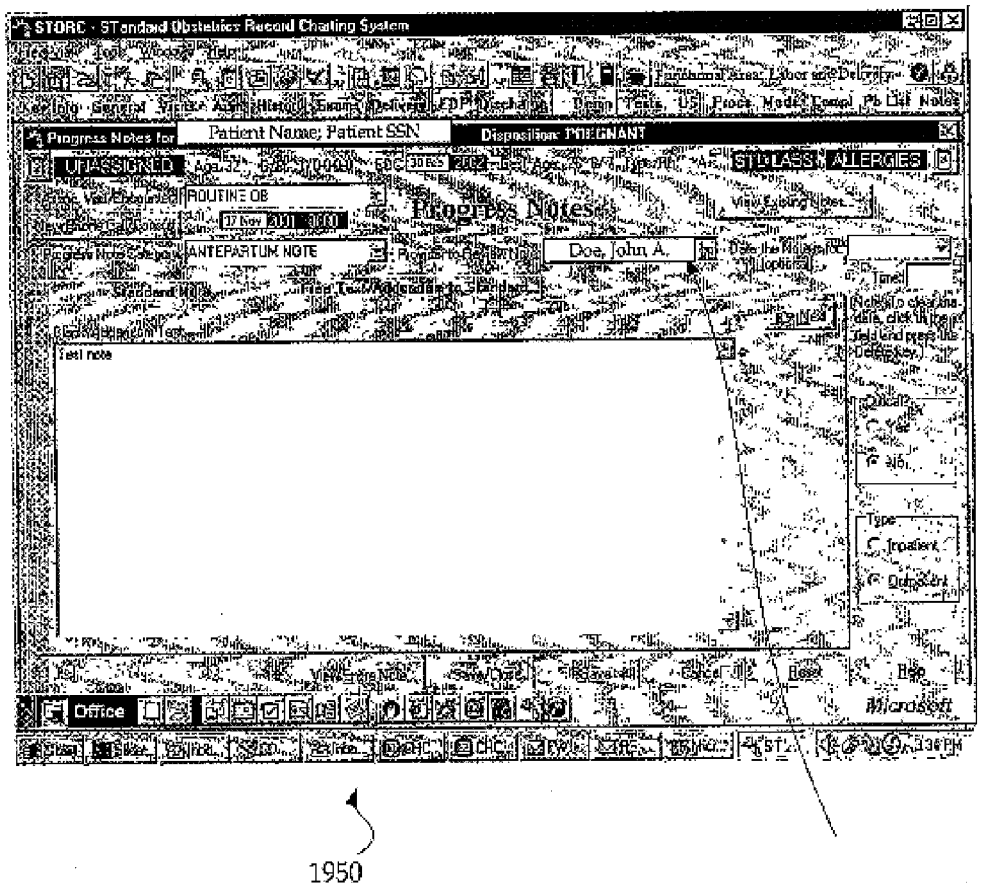

FIG. 19A illustrates a GUI used in one implementation of method step 1902 and in one implementation of method step 1904. Shown is an example GUI 1950, having a progress notes screen, wherein "provider to review note" designator 1952 is shown.

Figure 20:
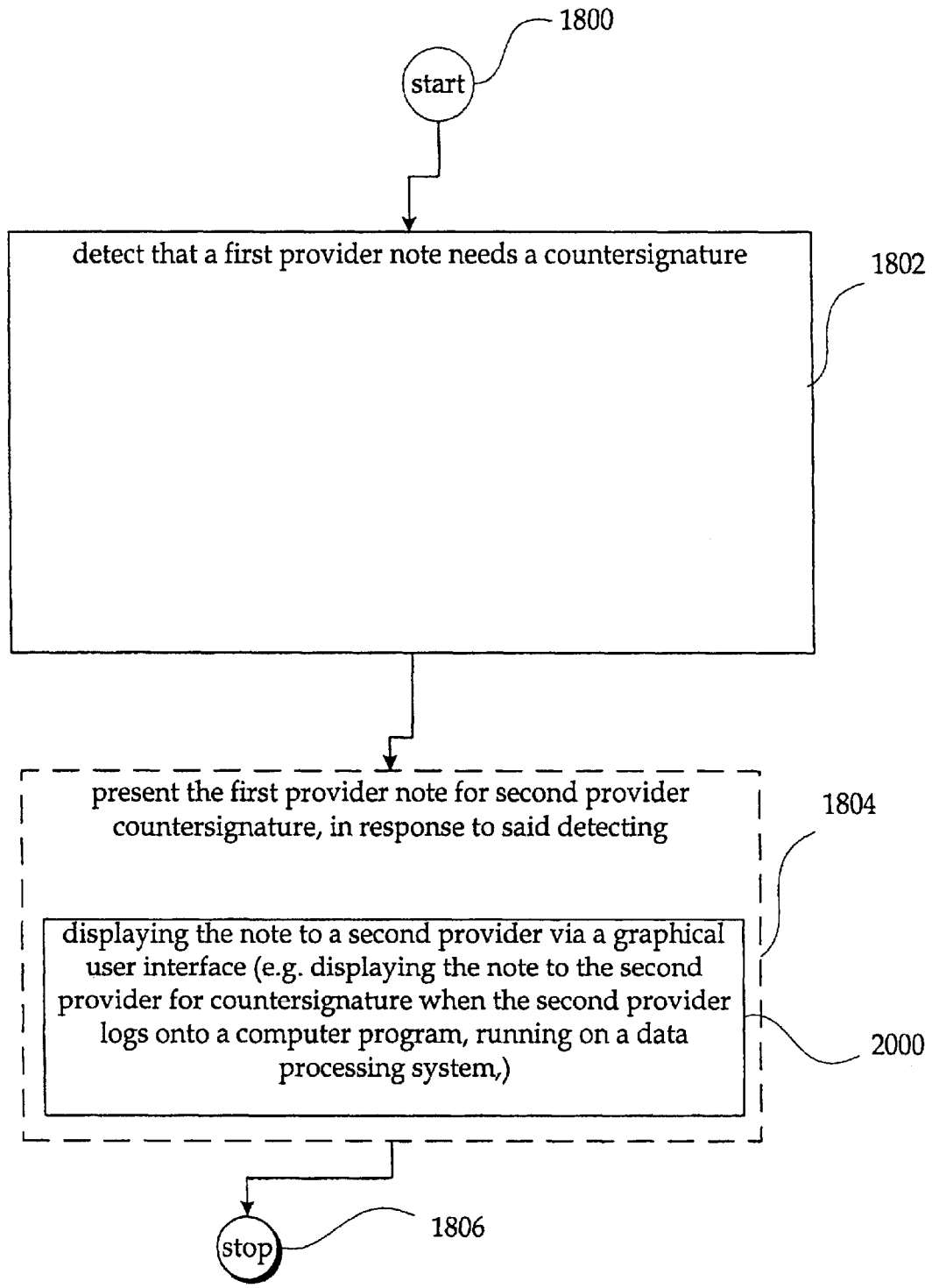

FIG. 20 depicts a high-level logic flowchart depicting an alternate implementation of the process shown in FIG. 18.

Figure 21:
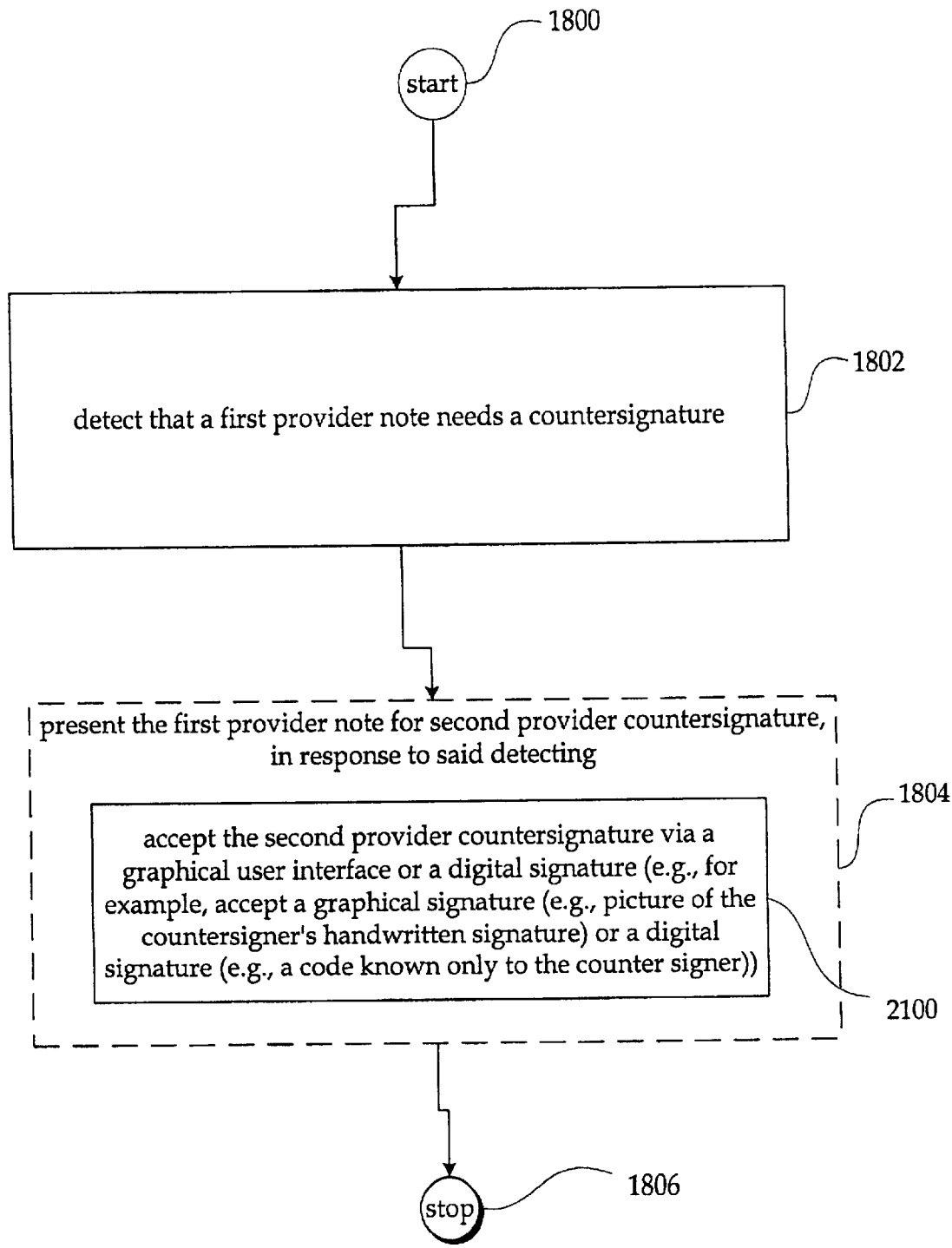

FIG. 21 depicts a high-level logic flowchart depicting an alternate implementation of the process shown in FIG. 18.

Figure 22:
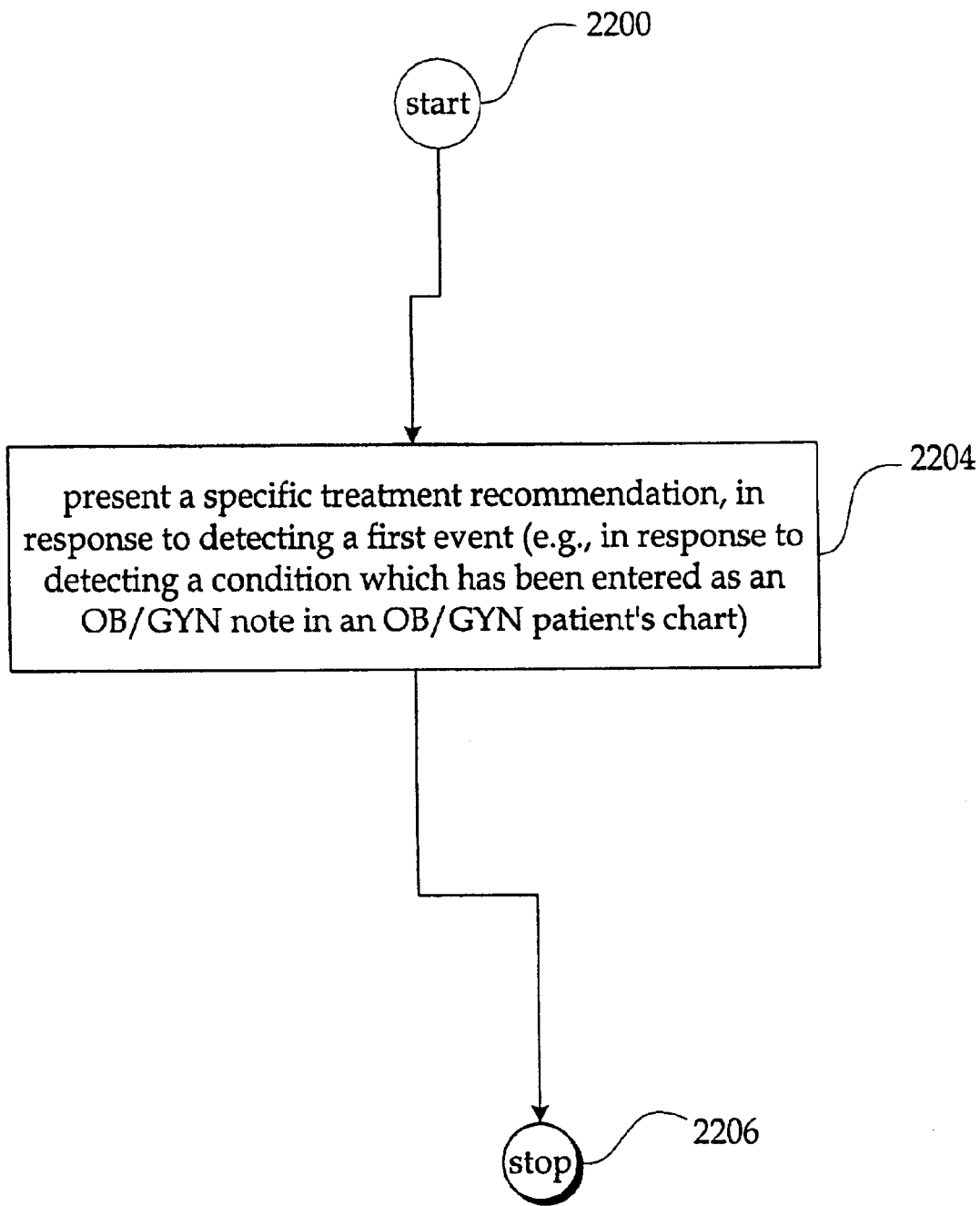

FIG. 22 shows a high-level logic flowchart depicting a process.

Figure 22A:
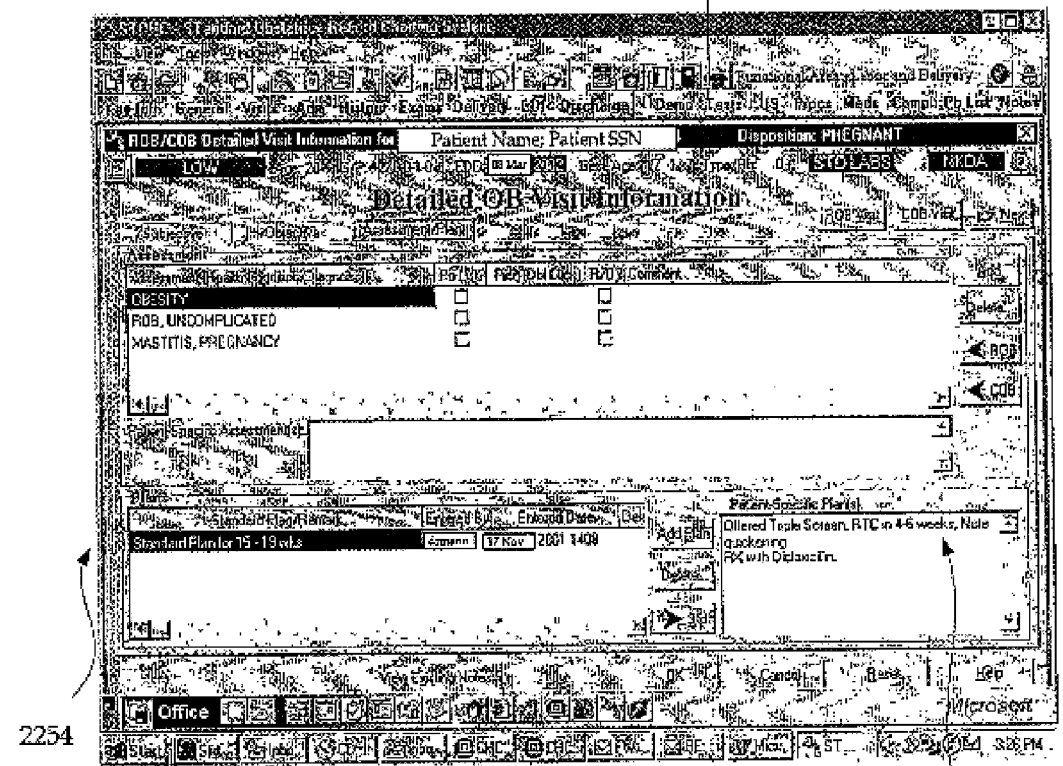

FIG. 22A shows an example GUI 2250 having a gestational age field 2252, wherein is shown standard plan overview field 2254, which in one implementation identifies the plan (e.g., "a standard plan for 15–19 wks is shown"), who authorized the plan (e.g., health care provider "jdoe"), and the date the plan was authorized (e.g., 16 Oct. 2001); and further wherein is shown a patient-specific plan field 2256, which in one implementation gives the details of the plan identified in the standard plan overview field 2254 as well as any additional plan specific to the patient which may have been entered, free text, by a health care provider.

Figure 22B:
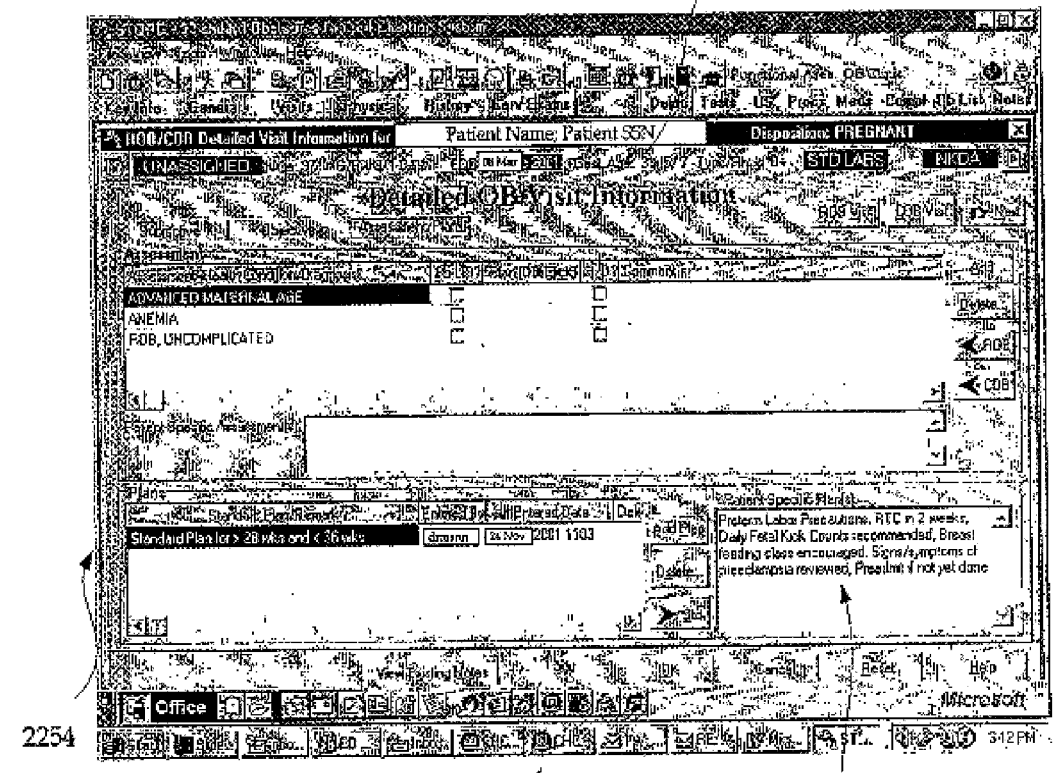
Figure 22C:
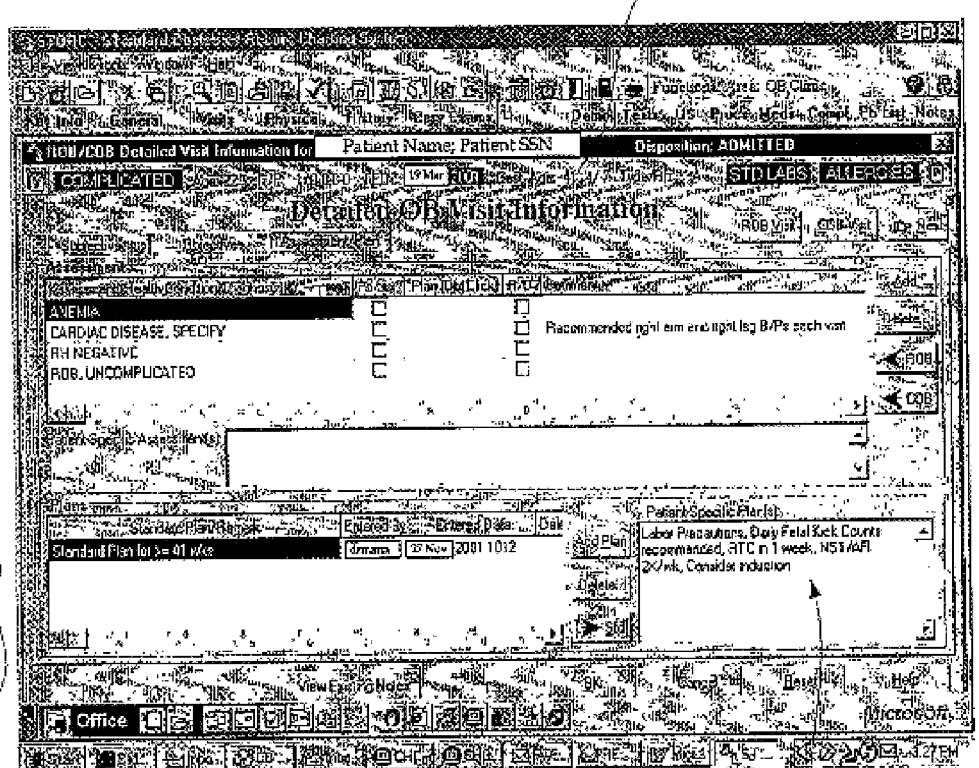

FIGS. 22B–C are substantially analogous to FIG. 22A except for respectively depicting plans for gestational age 28 to 36 weeks and gestational age greater than 41 weeks.

Figure 23:
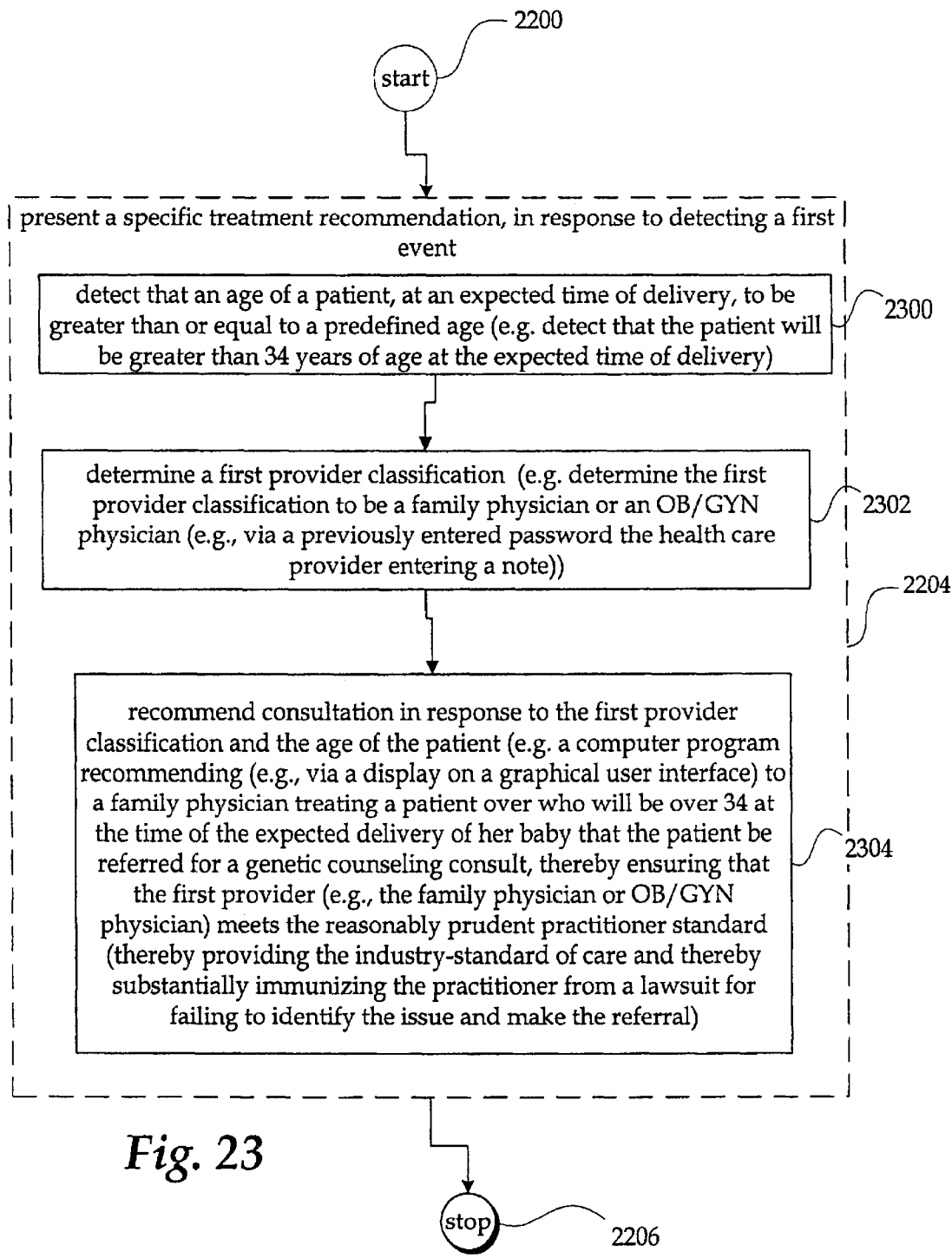

FIG. 23 depicts a high-level logic flowchart depicting an alternate implementation of the process shown in FIG. 22.

Figure 24:
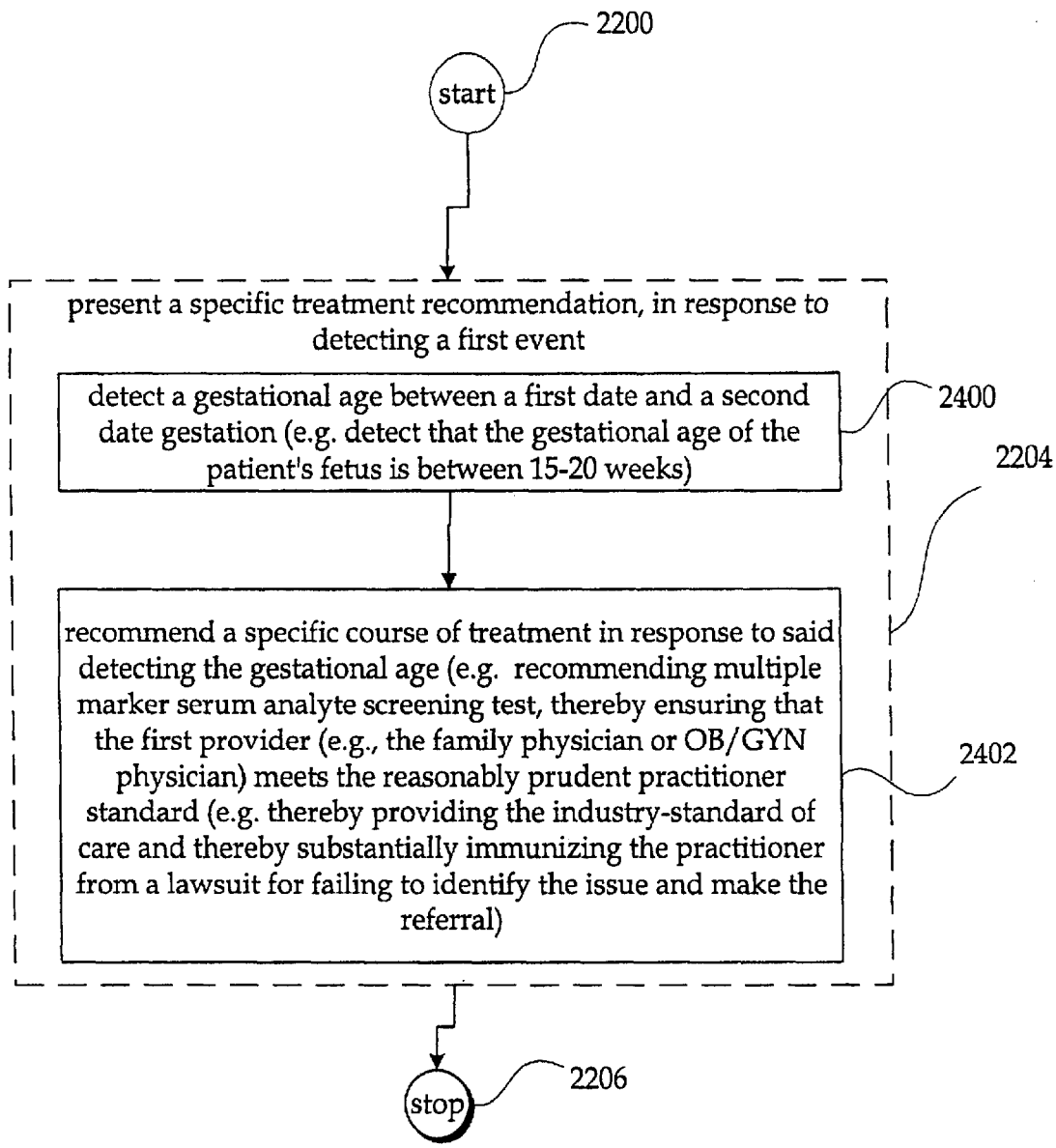

FIG. 24 depicts a high-level logic flowchart depicting an alternate implementation of the process shown in FIG. 22.

Figure 25:
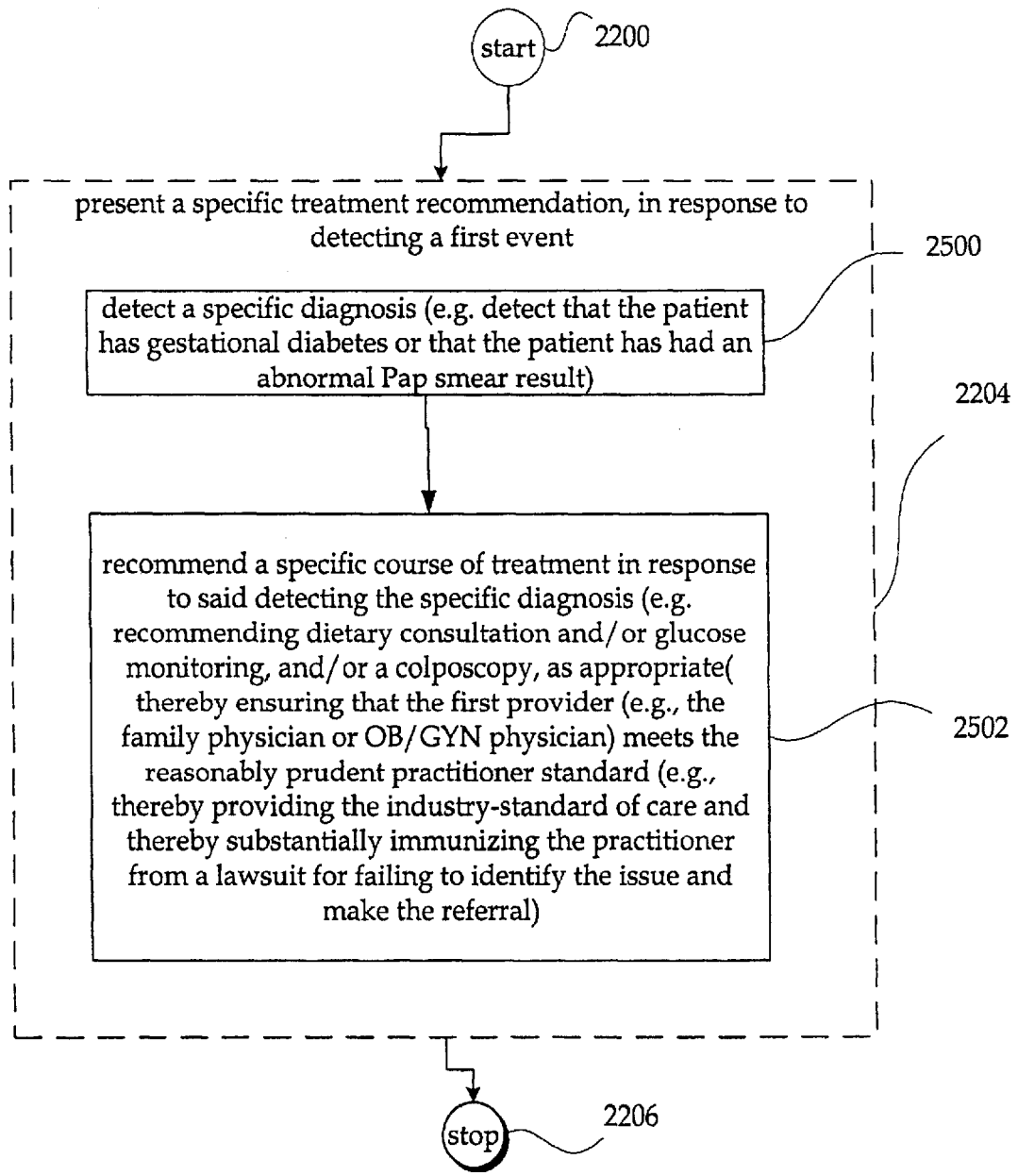

FIG. 25 depicts a high-level logic flowchart depicting an alternate implementation of the process shown in FIG. 22.

Figure 26:
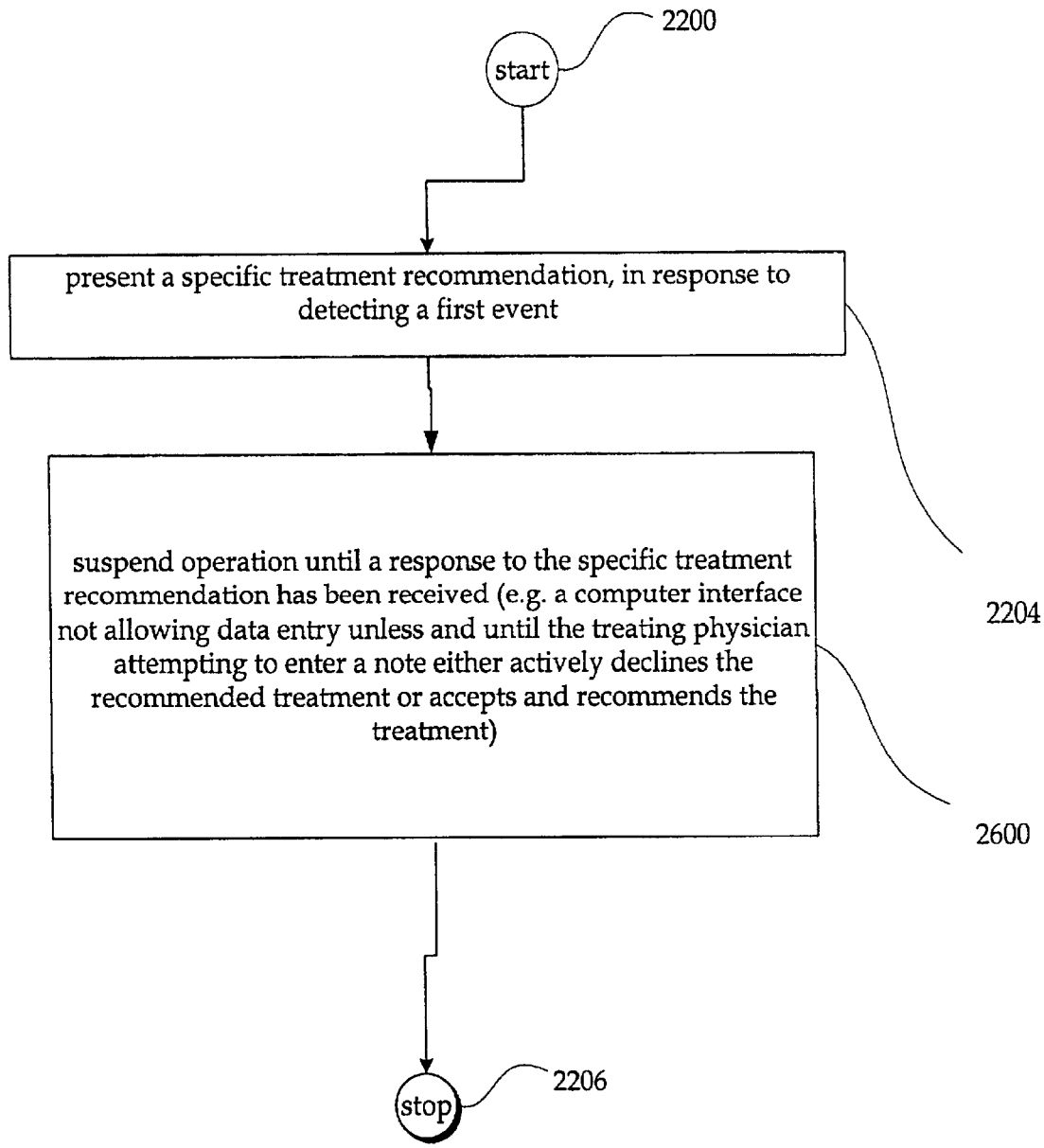

FIG. 26 depicts a high-level logic flowchart depicting an alternate implementation of the process shown in FIG. 22.

Figure 26A:
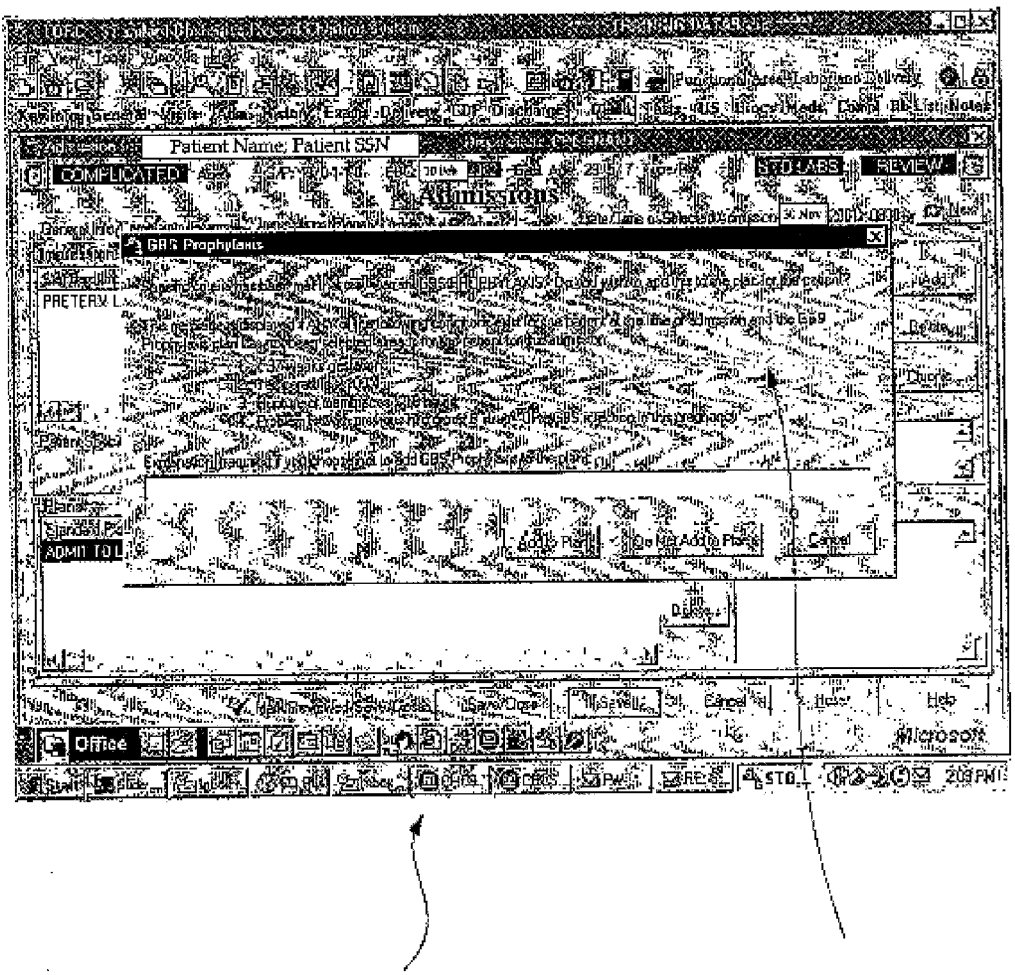

FIG. 26A illustrates a GUI used in one implementation of method step 2600.

Figure 27:
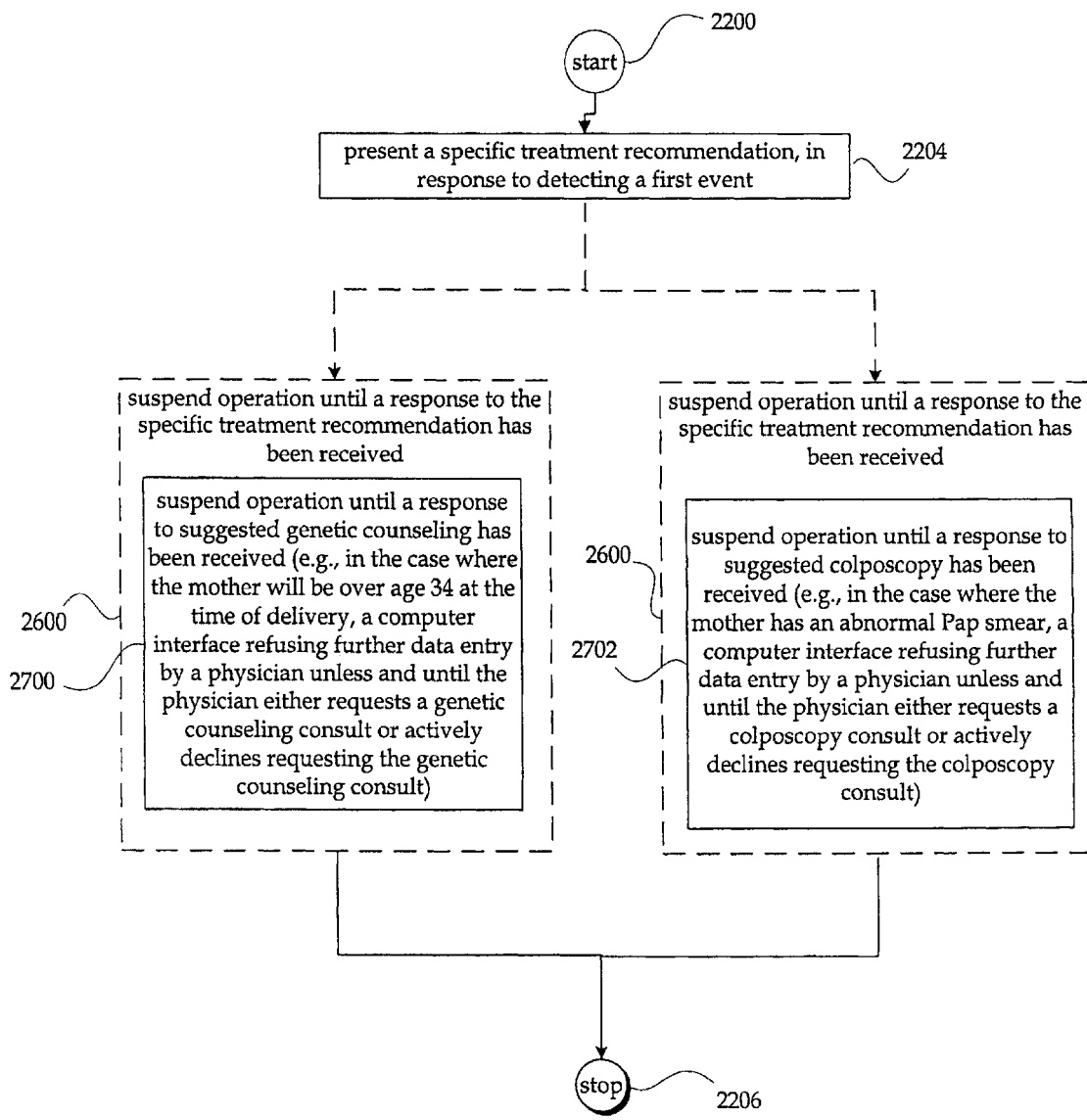

FIG. 27 depicts a high-level logic flowchart depicting alternate implementations of the process shown in FIG. 26.

Figure 28:
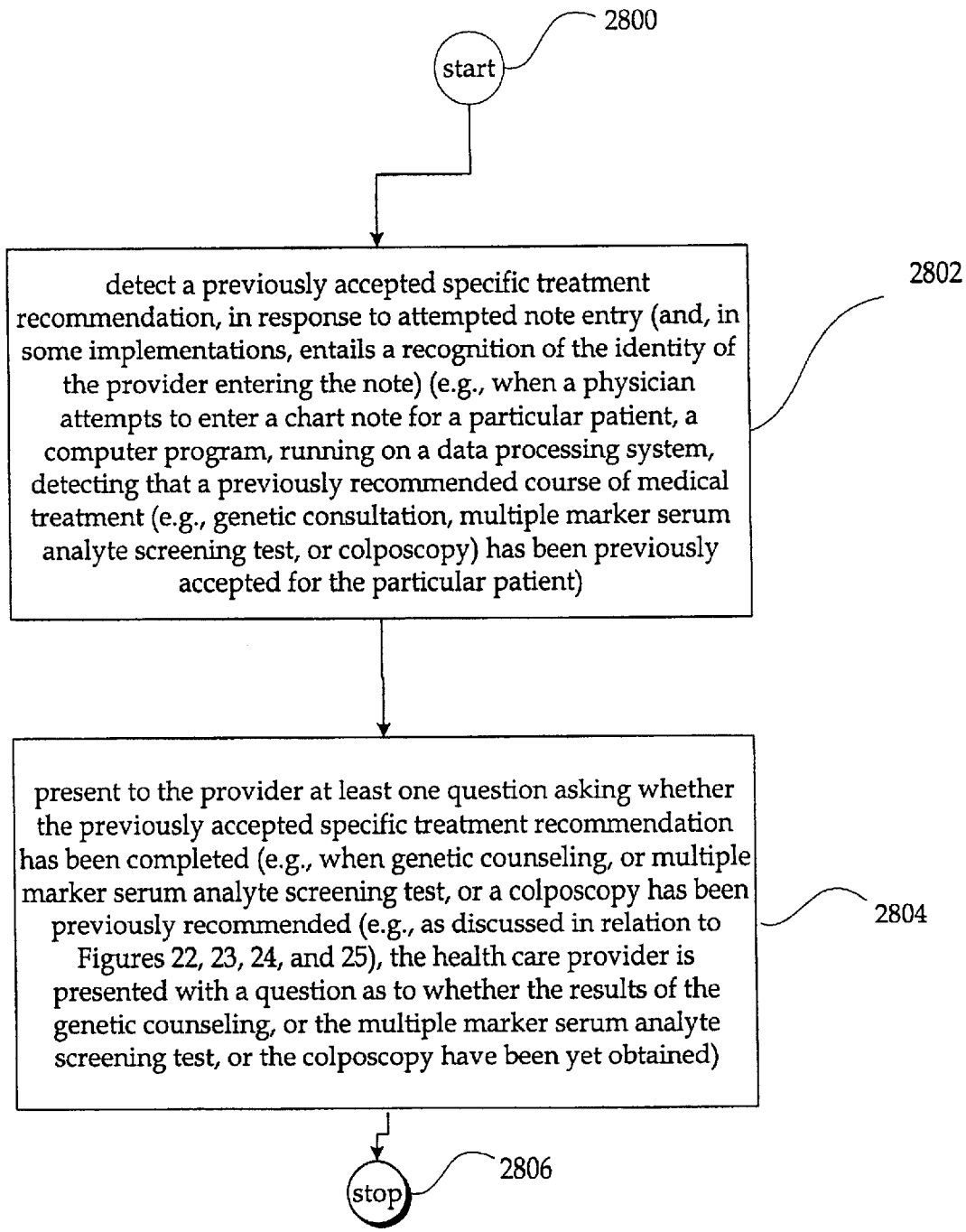

FIG. 28 depicts a high-level logic flowchart depicting a process.

Figure 29:
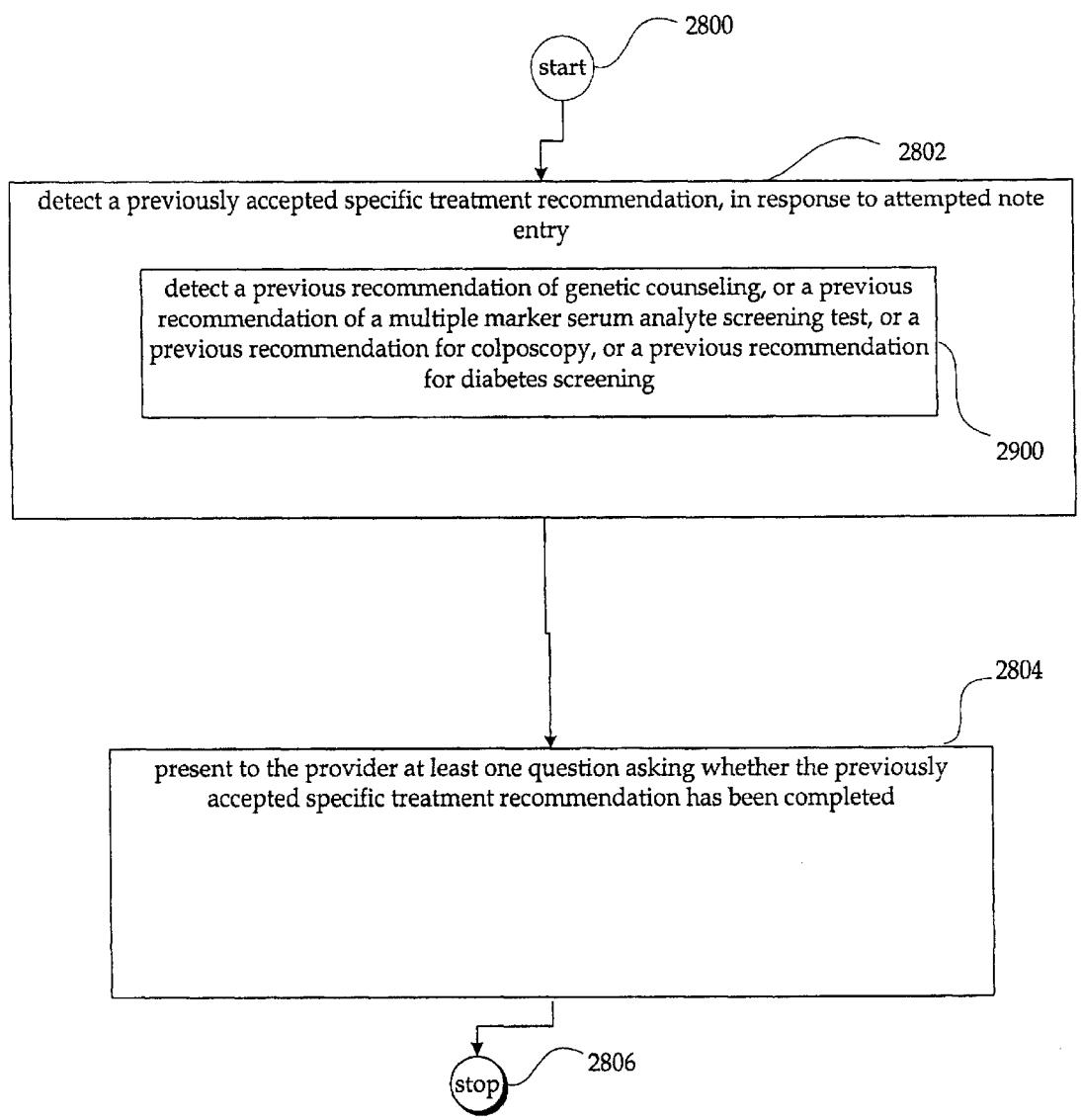

FIG. 29 depicts a high-level logic flowchart depicting an alternate implementation of the process shown in FIG. 28.

Figure 30:
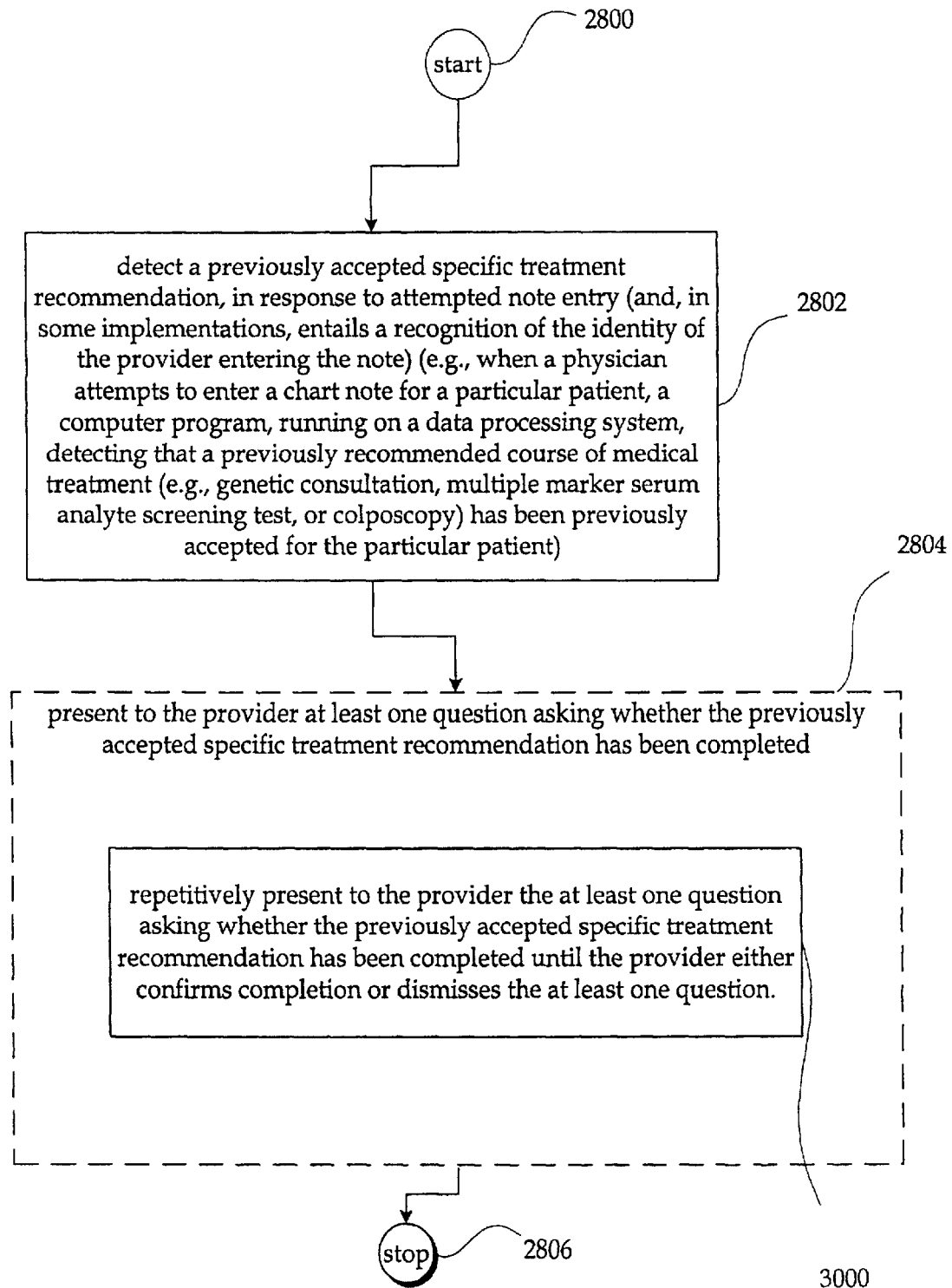

FIG. 30 depicts a high-level logic flowchart depicting alternate implementations of the process shown in FIG. 28.

Figure 31:
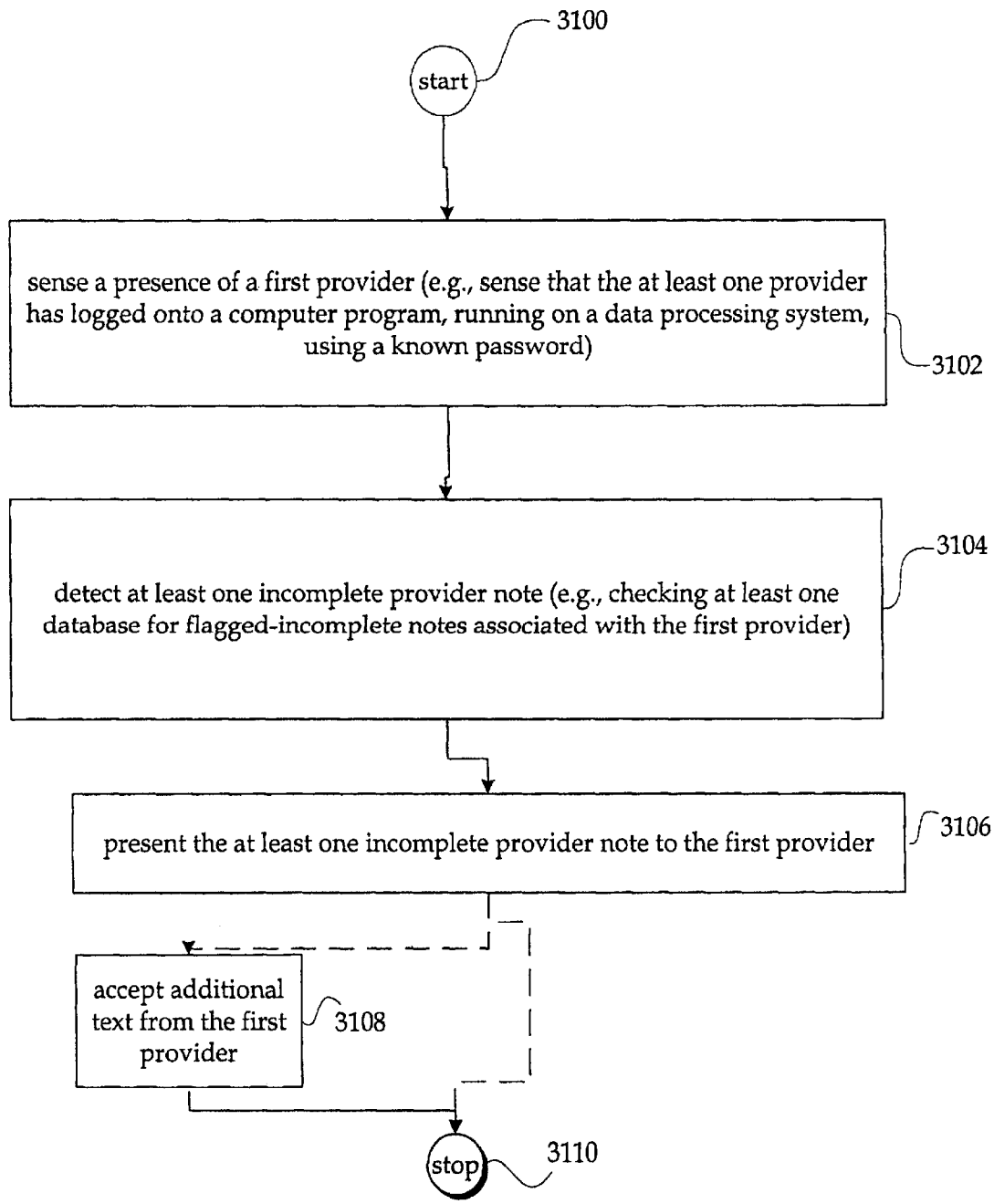

FIG. 31 shows a high-level logic flowchart depicting a process.

Figure 32:
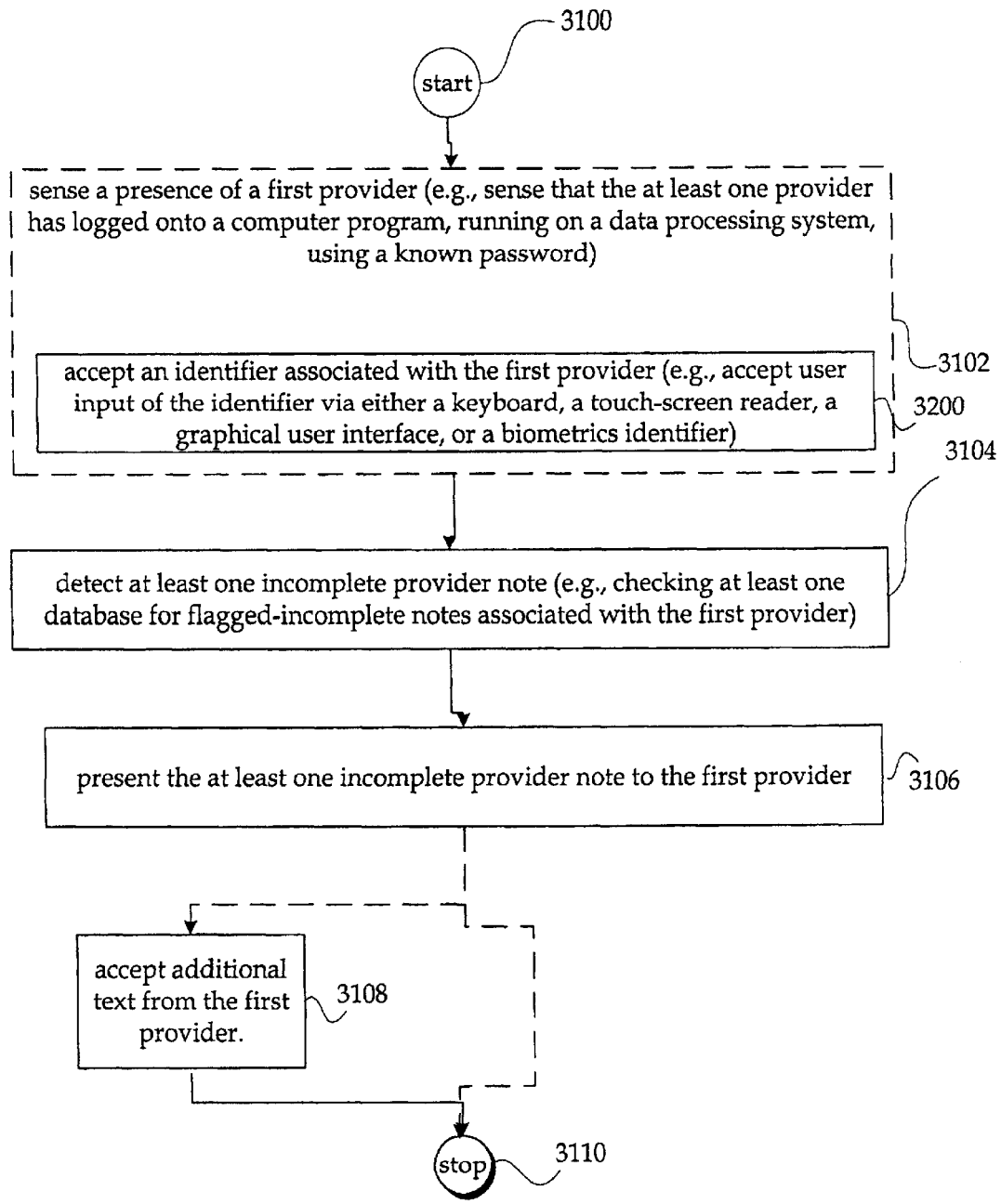

FIG. 32 depicts a high-level logic flowchart depicting an alternate implementation of the process shown in FIG. 31.

Figure 33:
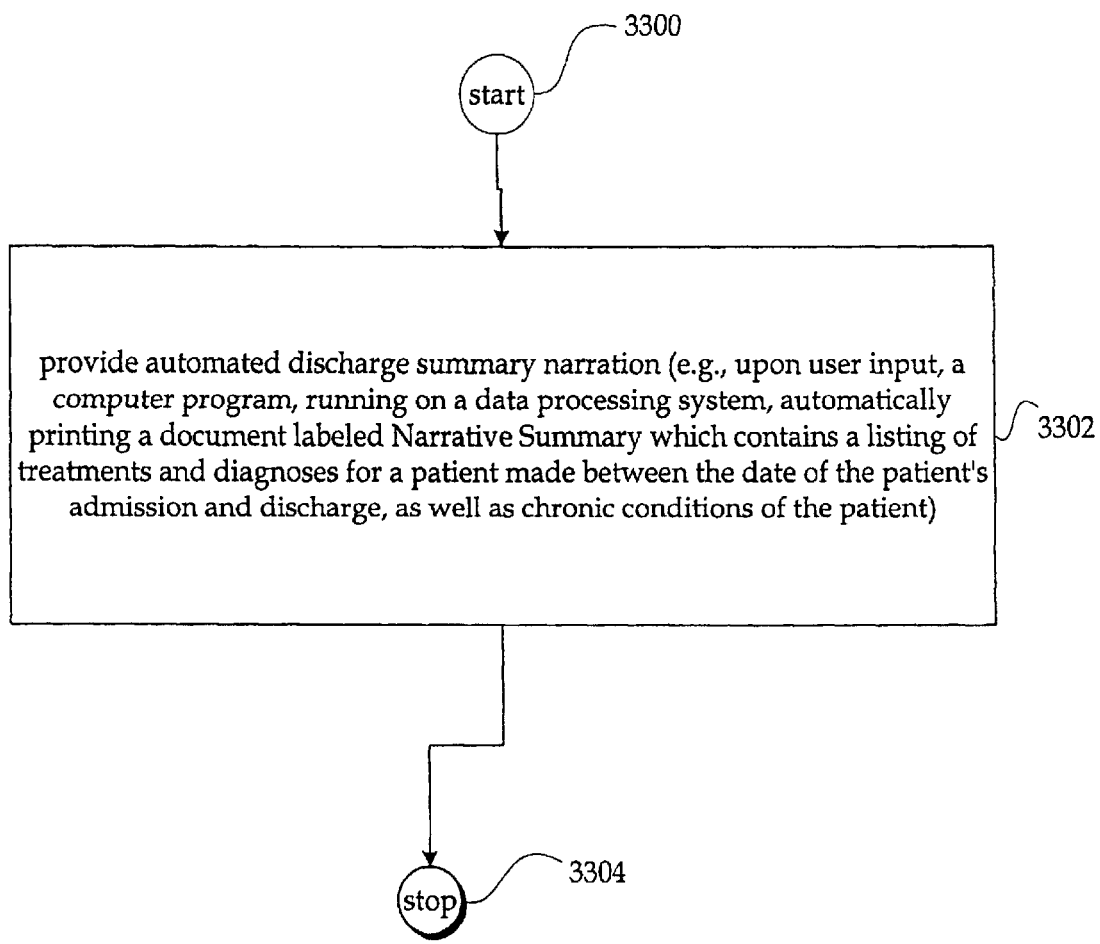

FIG. 33 shows a high-level logic flowchart depicting a process.

Figure 33A:
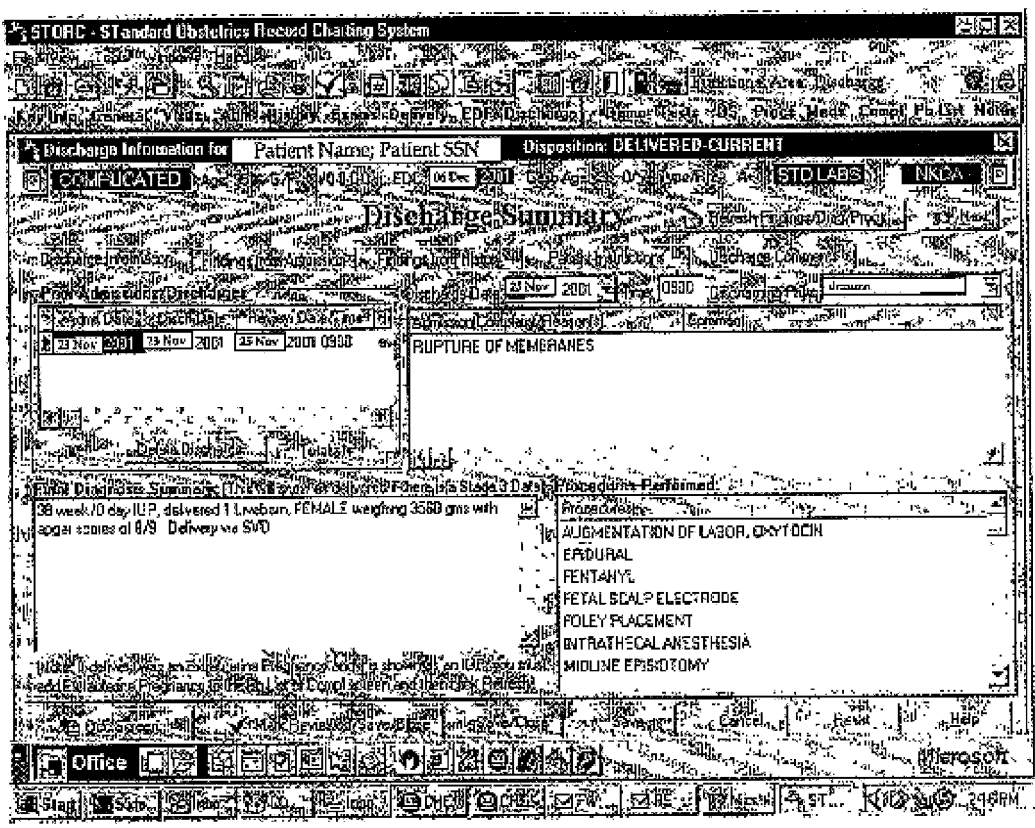

FIG. 33A depicts a GUI showing a "discharge information" discharge summary wherein are illustrated "discharge date," "prior admissions," "reasons for admission," "final diagnosis summary," and "procedures performed" listings.

Figure 33B:
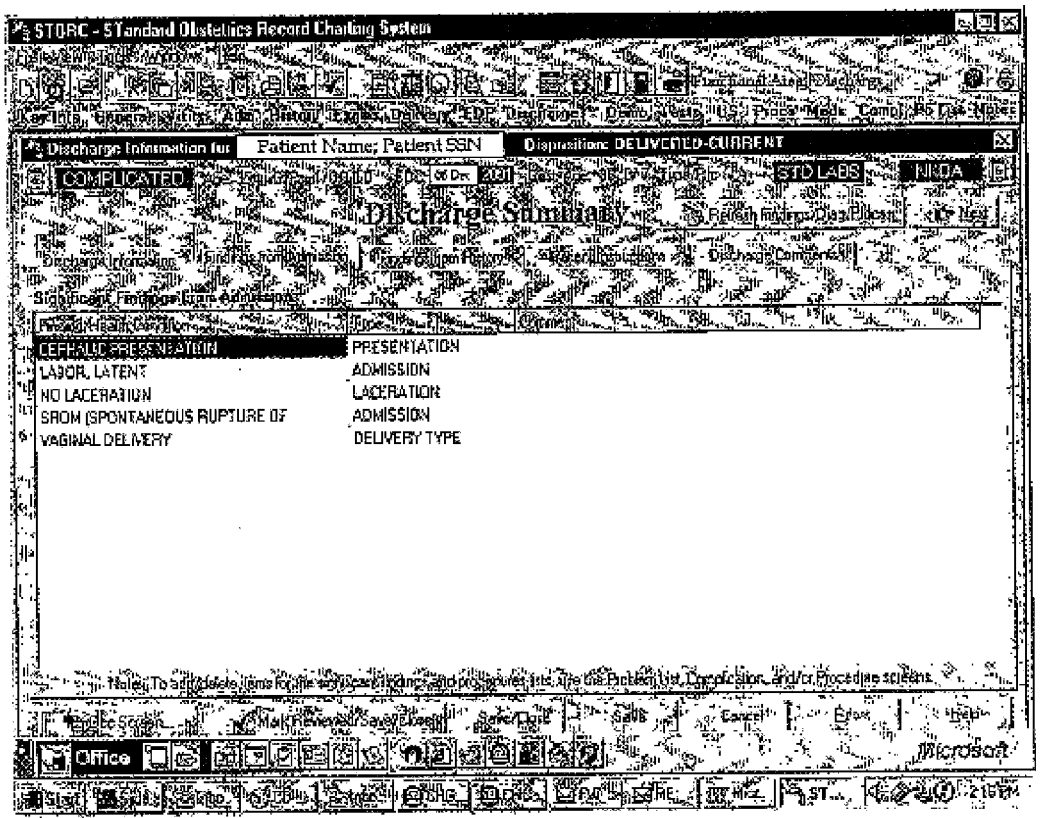
Figure 33C:
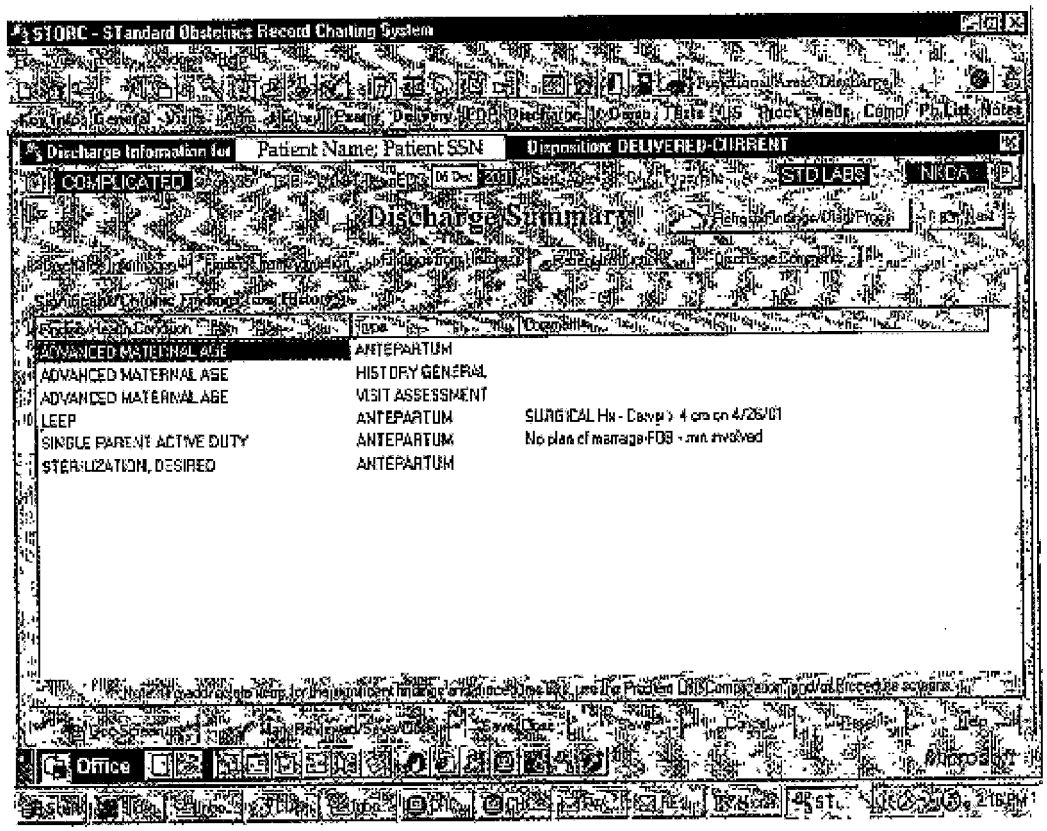

FIG. 33B depicts a GUI showing a "findings from admission" discharge summary wherein is illustrated a "significant findings from admission" listing. FIG. 33C depicts a GUI showing a "findings from history" discharge summary wherein is illustrated a "significant/chronic findings from history" listing.

Figure 33D:
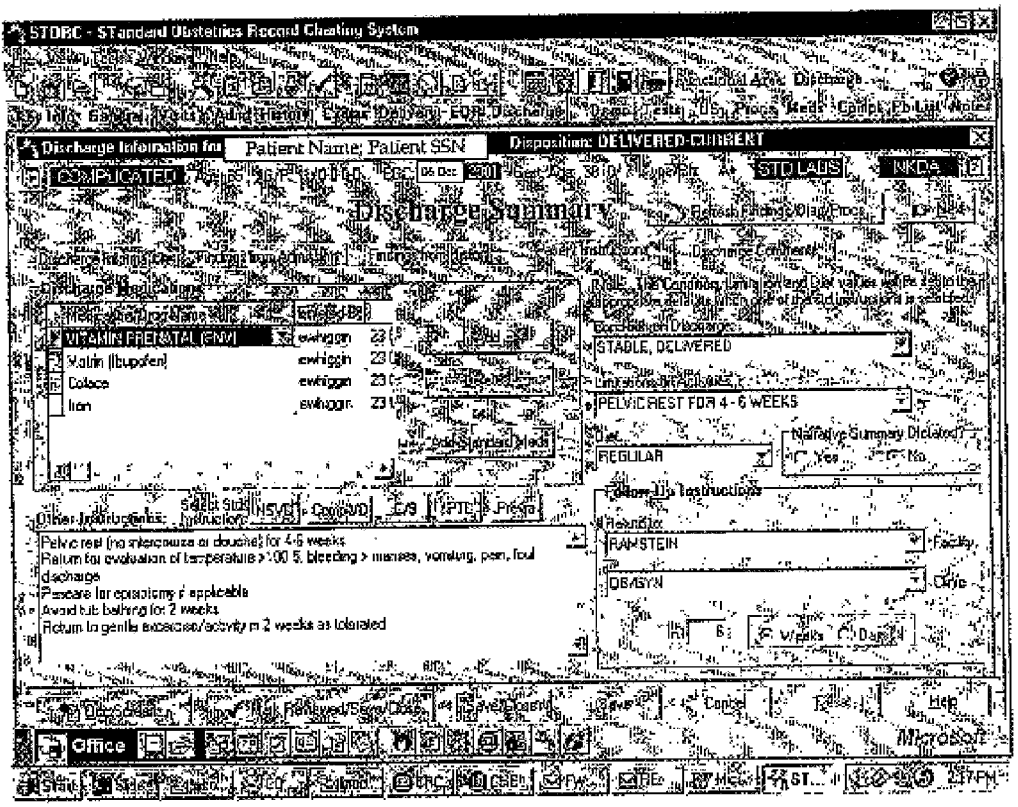

FIG. 33D depicts a GUI showing a "patient instructions" discharge summary wherein are illustrated "discharge medications," "other instructions," "limitations on activities," "diet," and "return to facility/clinic" listings; insofar as the discharge medications and other instructions listings are often loaded automatically, FIG. 33D also constitutes another example of an automated plan of treatment.

FIG. 33E depicts a GUI showing a "discharge comments" discharge summary wherein a health care provider can enter his or her comments free text.

Figure 34:
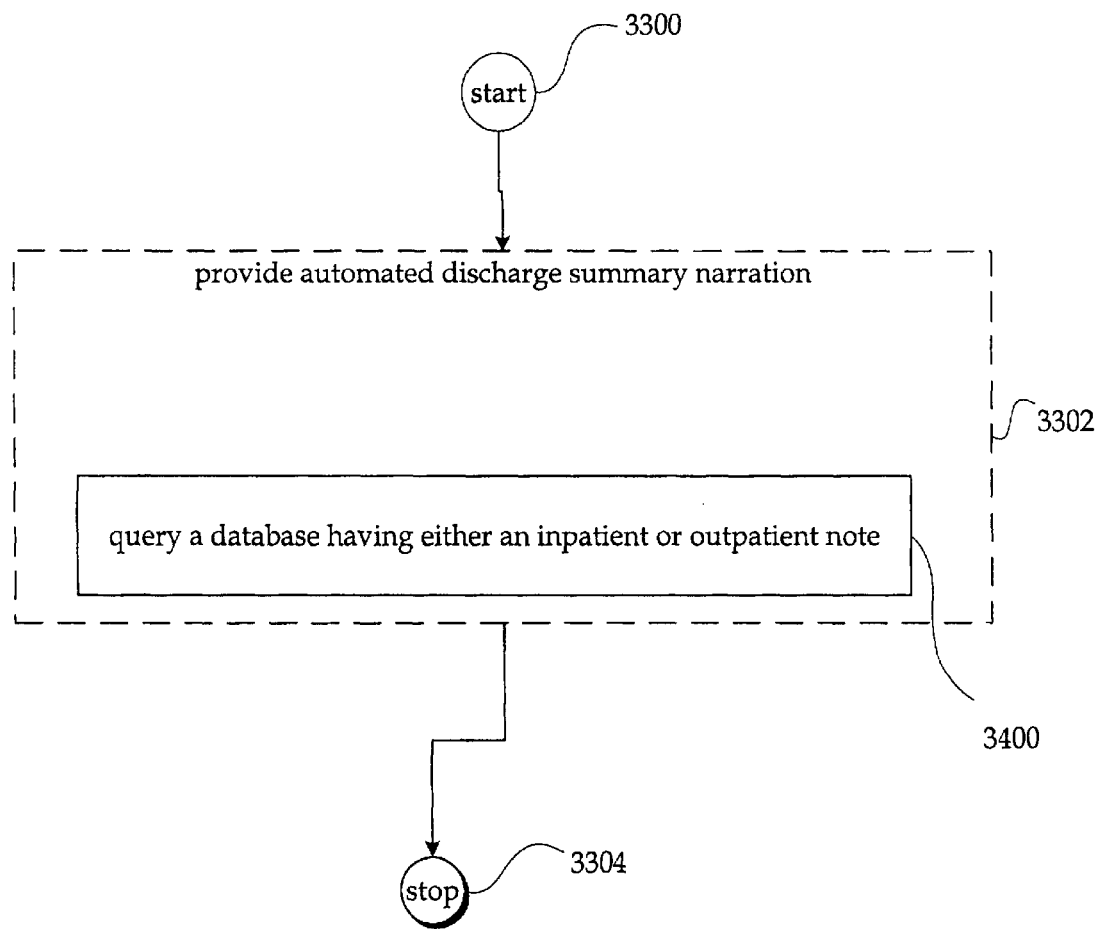

FIG. 34 depicts a high-level logic flowchart depicting an alternate implementation of the process shown in FIG. 33. The use of the same symbols in different drawings typically indicates similar or identical items.

DETAILED DESCRIPTION OF THE INVENTION

As noted above, the inventors have devised several methods and systems which support the practice of medicine. In some implementations, the methods and systems are embodied within one or more data processing systems in an environment including either or both inpatient and outpatient medical care facilities.

A. Outpatient and Inpatient Medical Care Facilities Environment

Figure 1:
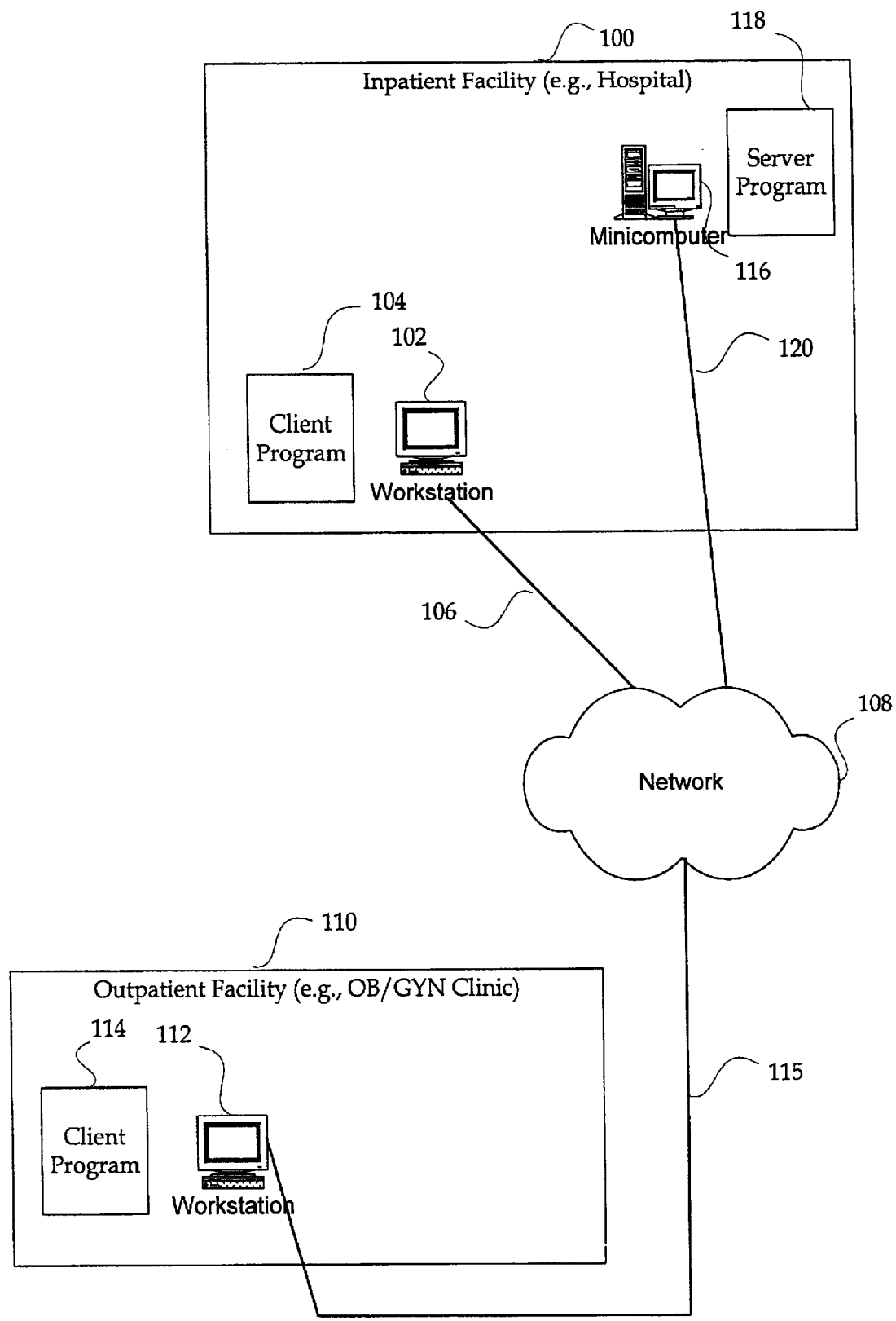
FIG. 1 shows an environment wherein methods and systems described herein may be utilized.

Referring now to FIG. 1, shown is an environment wherein methods and systems described herein may be utilized. Depicted is an inpatient facility (e.g., a hospital) 100 having a workstation data processing system 102 upon which is executing a client program (e.g., software) 104. Illustrated is that the workstation data processing system 102 has a data communications link 106 with a data communications network (e.g., a Wide Area Network (WAN), such as a private WAN or the public Internet (an internetworked agglomeration of subnetworks, which can be treated as a large LAN)) 108.

Illustrated is an outpatient facility (e.g., an OB/GYN clinic) 110 which has a workstation data processing system 112 upon which is executing a client program (e.g., software) 114. Illustrated is that the workstation data processing system 112 has a data communications link 115 with the data communications network 108.

Shown is a minicomputer data processing system 116 upon which is executing a server program (e.g., software) 118. Illustrated is that the minicomputer data processing system 116 has a data communications link 120 with the data communications network 108.

With respect to the depicted environment, although only one outpatient and inpatient facility are shown, those having ordinary skill in the art will recognize that more than one outpatient and/or inpatient facility could be present. Furthermore, those having ordinary skill in the art will appreciate that although only one workstation data processing system, and associated client program are shown in the context of each inpatient and outpatient facility in an actual implementation it is likely that several data processing systems and associated client programs will be present at each outpatient and inpatient facility. Those having ordinary skill in the art will also appreciate that although only one server program is shown, more than one server program running on more than one minicomputer could be present (e.g., redundant and/or distributed systems could be maintained). Lastly, those having ordinary skill in the art will recognize that the environment depicted has been kept simple for sake of conceptual clarity, and hence is not intended to be limiting.

Following are a series of flowcharts depicting implementations of processes. For ease of understanding, the flowcharts are organized such that the initial flowcharts present implementations via an overall "big picture" viewpoint and thereafter the following flowcharts present alternate implementations and/or expansions of the "big picture" flowcharts as either sub-steps or additional steps building on one or more earlier-presented flowcharts. Those having ordinary skill in the art will appreciate that the style of presentation utilized herein (e.g., beginning with a presentation of a flowchart(s) presenting an overall view and thereafter providing additions to and/or further details in subsequent flowcharts) generally allows for a rapid and easy understanding of the various process implementations.

B. Standardized Inpatient-Outpatient Nomenclatures

The inventors have discovered that, due to "mismatches" in professional, business, and administrative organizational structures, the dissemination of patent relevant information to the various health care providers involved in a particular patient's care is not always practicable. One specific difficulty that exists in the dissemination of patient relevant information is the common "mismatch" that exists between the nomenclatures used by health care providers in inpatient and outpatient contexts.

In order to understand the mismatch that often exists between inpatient and outpatient nomenclatures, it is helpful to understand what is meant by the terms "nomenclature," "inpatient," and "outpatient." The term "nomenclature" is etymologically related to the Latin word nomenclature ("assigning of names"), and hence as used herein means the set of terms or symbols (e.g., words) which are used in medical facilities to designate a grouping of medical criteria. The term "inpatient," as used herein, generally refers to persons receiving medical care who have been admitted to health facilities which provide room and board, for the purpose of observation, care, diagnosis, or treatment (e.g., persons admitted to hospitals). In contrast, the term "outpatient," as used herein, generally refers to a patient who is receiving medical care, but who does not meet the definition of inpatient (e.g., a person receiving medical care at an obstetrics/gynecology (OB/GYN) clinic).

The mismatch between inpatient and outpatient facilities can arise when the inpatient and outpatient facilities use a different name for a substantially similar grouping of one or more medical criteria. For example, in the specialty of OB/GYN, the term "toxaemia of pregnancy" typically refers to a condition, seen in the third trimester of pregnancy, that is characterized by hypertension, swelling, and the presence of protein in the urine, while the term "preclampsia" typically refers to a toxaemia of late pregnancy characterized by hypertension, edema and proteinuria. As can be seen, although there are slight differences in the groupings of the medical criteria to which the names "toxaemia of pregnancy" and "preclampsia," refer, the groupings of medical criteria are substantially similar. Accordingly, human OB/GYN health care providers treat the names as substantial synonyms, and so long as human OB/GYN health care providers interact the names can be used more or less simultaneously.

The inventors have discovered that in the day-to-day realities of medical practice, human health care providers typically do not communicate directly with each other, but rather that their communications are mediated by one or more inpatient and outpatient record-keeping systems, each of which has one or more nomenclatures. For example, rather than calling a patient's outpatient health care providers directly, an inpatient physician treating the patient often will consult the patient's "chart" (a record of the patient's medical treatment to date, which in the related art often appears in both electronic record and paper record format) to determine the patient's previous course of care and any medical conditions noted by the patient's outpatient health care provider(s).

The inventors have noted that if the patient's chart is "handwritten" (e.g., pen and ink), the mismatch in nomenclatures between the outpatient and inpatient facilities usually causes little difficulty, in that—returning to the earlier example—the human inpatient health care provider can recognize that "toxaemia of pregnancy" and "preclampsia" may be treated as synonyms. However, the inventors have discovered that when at least a part of the patient's chart is in an electronic form, mismatches in nomenclatures between inpatient and outpatient facilities can have grave implications for health-care providers.

The inventors have noted that, unlike pen-and-ink records, which allow the health care provider to enter basically whatever data he or she wants when referring to medical information, electronic records generally have a defined nomenclature which must be used if data is going to be entered into the system. The inventors have further noted that, as in the pen-and-ink example described above, the nomenclatures used in the outpatient and inpatient facilities, at least one of which uses electronic record keeping, can be inconsistent. For example, an outpatient electronic record-keeping system which uses and/or will accept the term "preclampsia," but not "toxaemia of pregnancy," and an inpatient record-keeping system which uses and/or will accept the term "toxaemia of pregnancy," but not "preclampsia."

As noted above, where both facilities use "pen and ink" charting, such mismatching is generally not that significant.

However, the inventors have discovered that where at least one facility uses electronic charting, the mismatches in nomenclature can become significant. Specifically, the inventors have discovered that, due to the fact that the people transferring data between the outpatient and inpatient facilities are often not the health care providers themselves (e.g., data entry people or systems), if the nomenclatures are not consistent across the outpatient and inpatient facilities, the data is often dropped. For example, if an inpatient data entry person sees the term toxaemia of pregnancy but the inpatient electronic charting system only accepts "preclampsia," the diagnosis of "preclampsia" is often dropped since the data entry person does not have sufficient information or authority to equate the two terms. So far as the inventors know, no one has yet recognized this problem, and the inventors believe that this arises, at least in part, from the fact that data entry personnel and health care providers are often widely separated professionally, geographically, and organizationally.

In light of the foregoing, the inventors have postulated that for effective communication between outpatient and inpatient facilities to occur, it would be helpful to have methods and systems that allow the outpatient and inpatient facilities to share the same nomenclature. Accordingly, the inventors describe herein methods and systems that allow the outpatient and inpatient facilities to share the same nomenclature.

In contradistinction to the related art, the inventors have taken the position that if the nomenclature problem is approached from a clinical (e.g., health care provider) perspective rather than from a data processing system perspective (which has typically been the case in the related art), transition to methods and system which provide a common nomenclature across inpatient and outpatient facilities will be easier. Toward this end, rather than beginning with the design of forms for the system, which is typically the case in the related art, the inventors decided that it would be better to begin by examining the course of treatment for particular patients, deciding what information is accepted within the art as helpful in such treatment, and making sure that the system captures that information. It is the inventors' hypothesis that—insofar as existing record keeping systems are intended to be ultimately related to patient care—it is likely that by focusing on the patient care approach it is probable that the information needed by any form will be captured by the "clinician-driven system. This approach has entails: (1) recording certain "clinically significant" medical diagnoses, medical treatments, and medical administrative matters (each of which are collectively referred to herein as "names for groupings of one or more medical criteria") which preferably should almost always be accessible to a health care provider; (2) for each set of names for each of the groupings of medical criteria, selecting at least one name as forming a common inpatient-outpatient nomenclature, and (3) providing at record-keeping system having a "pick-list" composed of the selected common inpatient-outpatient nomenclature, from which health care providers may select names, thereby providing consistency for clinically significant names across the system.

Those having ordinary skill in the art will appreciate that what might be considered "clinically significant" medical diagnoses, medical treatments, and medical administrative matters could vary from facility from facility, and thus the preferred way to determine what is clinically significant would be to actually record the responses of one or more persons actually involved in the delivery, administration, or legal review of patient care for a particular medical area.

Insofar as that the inventors are both OB/GYN specialists, the present discussion is based on OB/GYN practice. However, those having ordinary skill in the art will appreciate that the present discussion is not limited to OB/GYN practice but is instead applicable across all medical practice areas.

Figure 2:
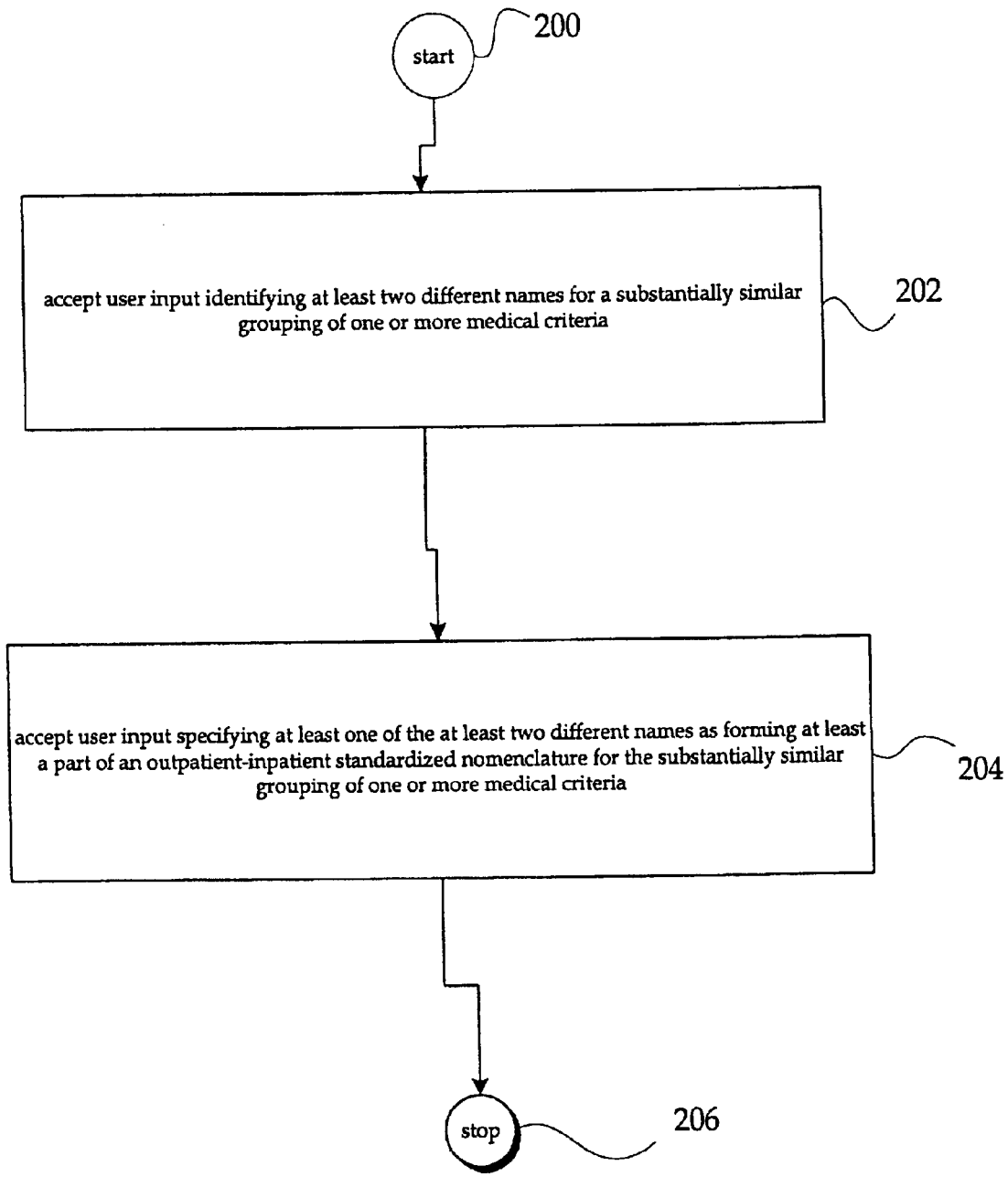
FIG. 2 shows a high-level logic flowchart depicting a process.

Referring now to FIG. 2, shown is a high-level logic flowchart depicting a process. Method step 200 shows the start of the process. Method step 202 depicts accepting user input identifying at least two different names for a substantially similar grouping of one or more medical criteria. Method step 202 entails recording whatever medical diagnoses, medical treatments, and/or medical administrative matters which identified one or more health care providers deem clinically significant (i.e., which should preferably almost always be known to a health provider treating a patient). For example, if the one or more identified health care provider worked in the field of OB/GYN, the recorded medical diagnoses, medical treatments, and/or medical administrative matters might respectively include a diagnosis of chronic diabetes, the fact that the patient is taking a prescribed blood thinner, and fact that the OB/GYN physician was awaiting the results of a genetics screening. Reasons why the foregoing might be deemed clinically significant might be that the chronic diabetes and blood thinner issues impact on what the OB/GYN physician might prescribe for the patient in terms of treatment and medication, while the fact that the OB/GYN physician is awaiting the results of genetic screening might ultimately prove important in a subsequent wrongful life lawsuit. Method step 202 will effectively often result in the recordation of substantial synonyms for substantially similar groupings of one or more medical criteria.

Method step 204 illustrates accepting user input specifying at least one of the at least two different names as forming at least a part of an outpatient-inpatient standardized nomenclature for the substantially similar grouping of one or more medical criteria. Typically, this input would be by the one or more health care providers identified across any inpatient and outpatient facilities under consideration. For example, if the identified names related to pregnancy, method step 204 would typically include accepting input from OB/GYN physicians, nurses, and nurse practitioners who work either in the OB/GYN department of a hospital or in an OB/GYN clinic (e.g., a "women's health" clinic). Method step 210 entails the selection, from among each of the created groups of synonyms, of at least one word which is used to at least partially define the inpatient-outpatient standardized nomenclature. In one implementation, the selection of words to be used to define the inpatient-outpatient standardized nomenclature is done via consensus reached among a group which includes both inpatient and outpatient OB/GYN physicians. However, in one instance, in order to accelerate and simplify implementation, the selection was done unilaterally by one OB/GYN physician. In some implementations, the health care providers identify the synonyms via use of a specialty dictionary.

The outpatient-inpatient standardized nomenclature now defined, method step 206 shows the end of the process.

Figure 3:
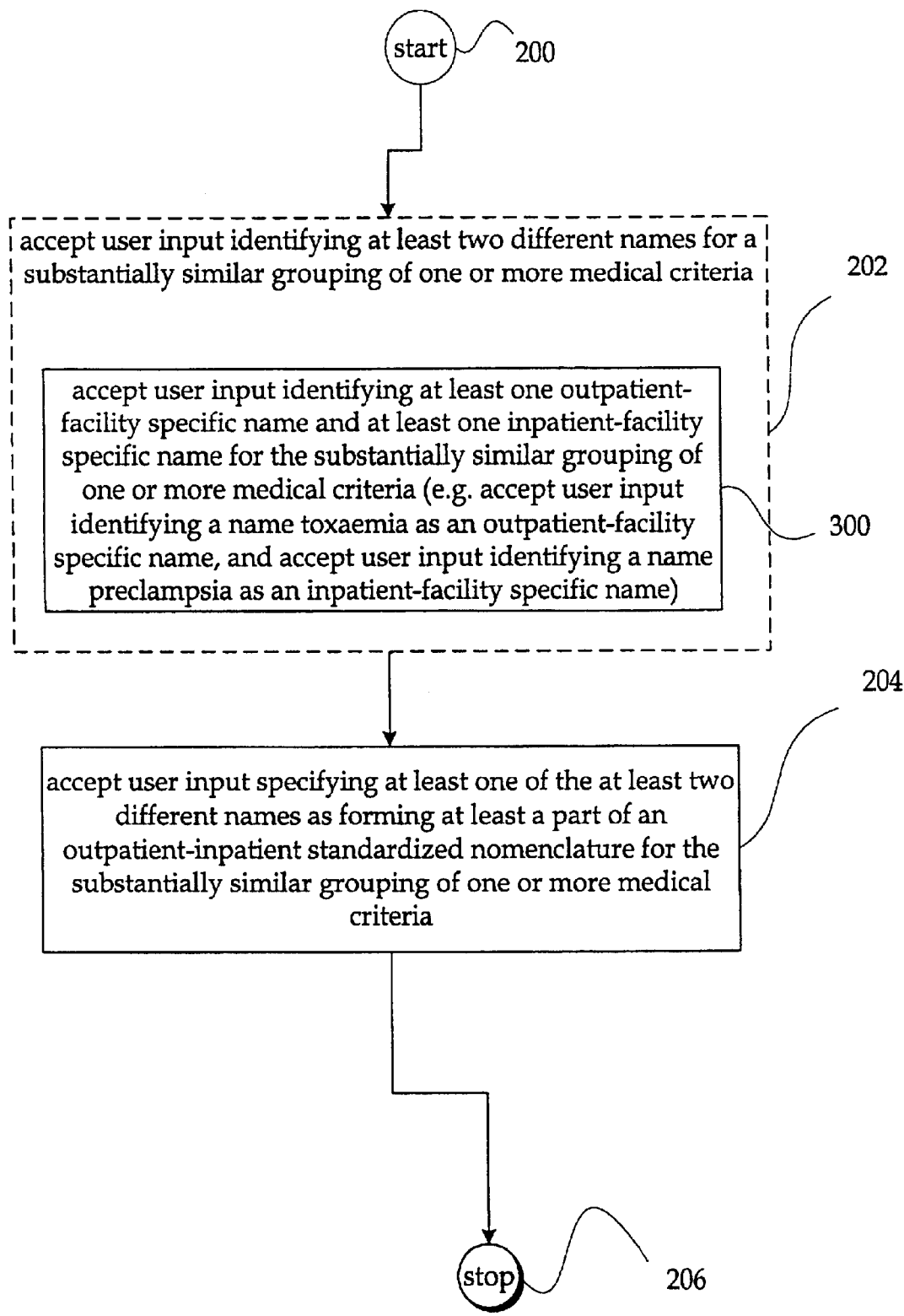
FIG. 3 depicts a high-level logic flowchart depicting an alternate implementation of the process shown in FIG. 2.

Referring now to FIG. 3, depicted is a high-level logic flowchart depicting an alternate implementation of the process shown in FIG. 2. Method step 300 illustrates that, in one implementation, method step 200 is characterized by accepting user input identifying at least one outpatient-facility specific name and at least one inpatient-facility specific name for the substantially similar grouping of one or more medical criteria; for example, accepting user input identifying a name toxaemia as an outpatient-facility specific name, and accepting user input identifying a name preclampsia as an inpatient-facility specific name. The remaining method steps function as described elsewhere herein.

Figure 4:
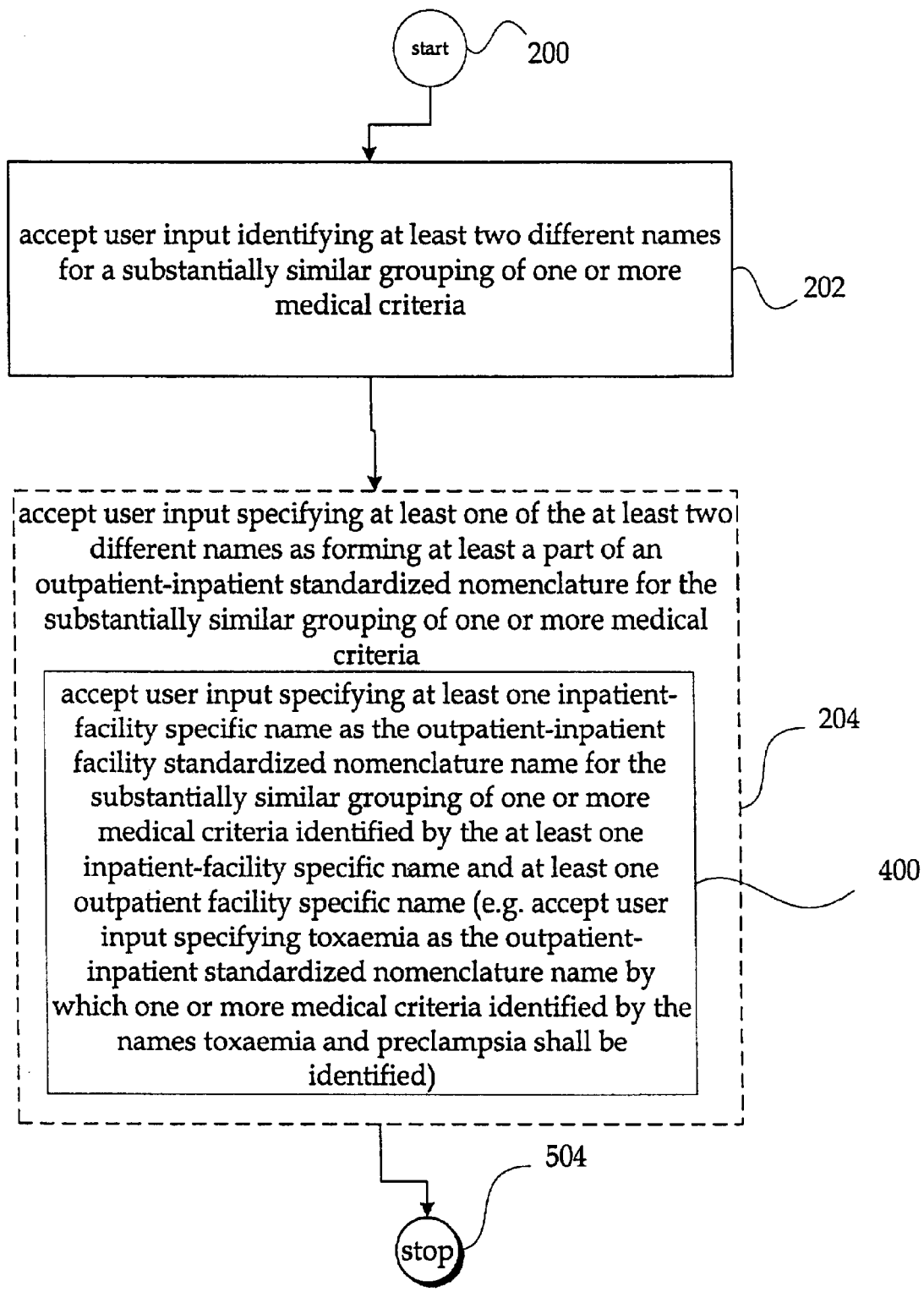
FIG. 4 depicts a high-level logic flowchart depicting an alternate implementation of the process shown in FIG. 2.

Referring now to FIG. 4, depicted is a high-level logic flowchart depicting an alternate implementation of the process shown in FIG. 2. Method step 400 illustrates that, in one implementation, method step 204 is characterized by accepting user input specifying at least one inpatient-facility specific name as the outpatient-inpatient standardized nomenclature name for the substantially similar grouping of one or more medical criteria identified by the at least one inpatient-facility specific name and at least one outpatient facility specific name; for example, accepting user input specifying toxaemia as the outpatient-inpatient standardized nomenclature name by which one or more medical criteria identified by the names toxaemia and preclampsia shall be identified. The remaining method steps function as described elsewhere herein.

C. Accepting Both Outpatient and Inpatient Data to Commonly Accessible Storage

Figure 5:
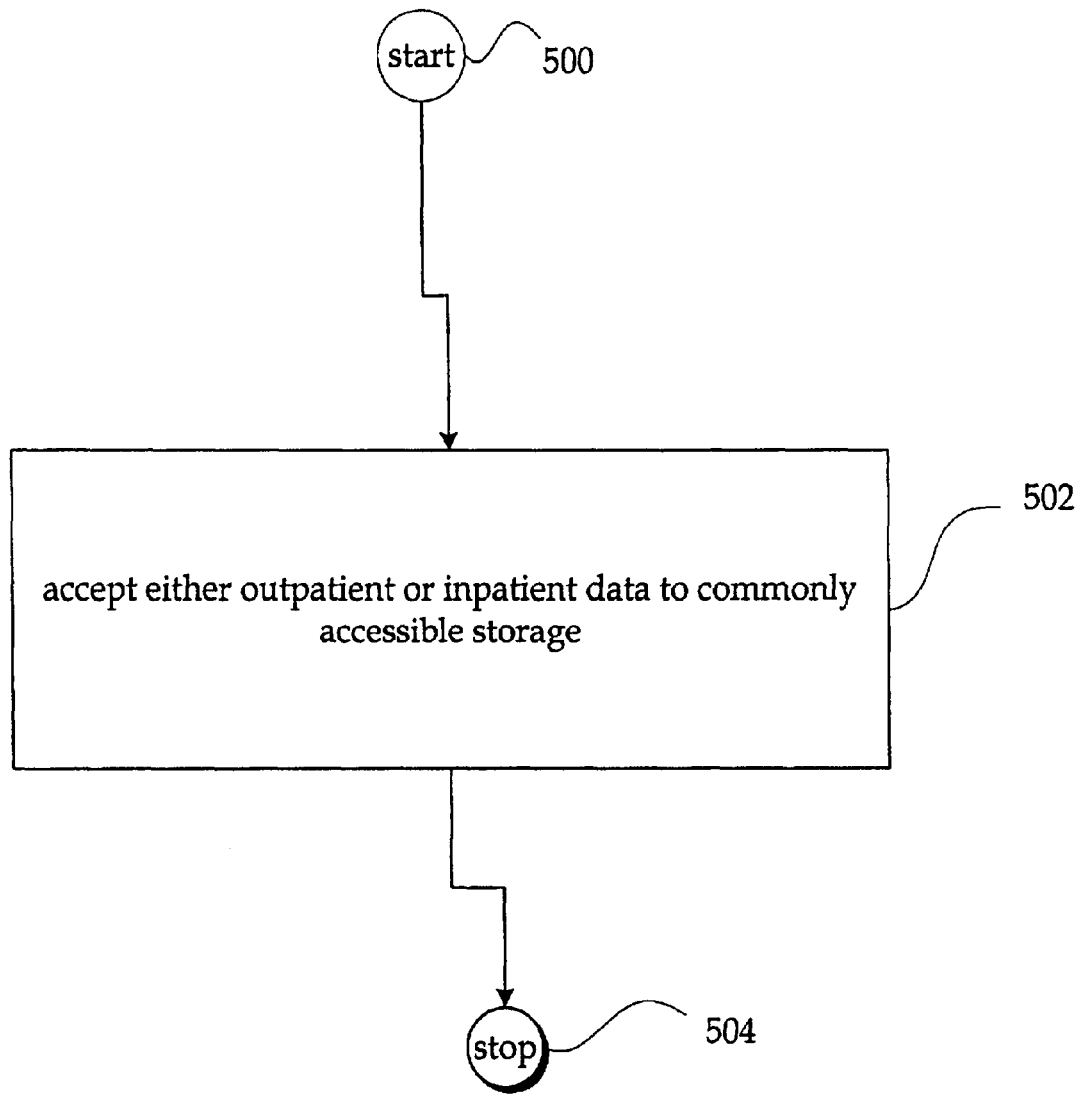
FIG. 5 shows a high-level logic flowchart depicting a process.

Referring now to FIG. 5, shown is a high-level logic flowchart depicting a process. Method step 500 shows the start of the process. Method step 502 depicts accepting either outpatient or inpatient data to commonly accessible storage. For example, specifying at least two patient treatment facilities from which medical diagnoses, medical treatments, and medical administrative matters are expected to be received (e.g., specifying an inpatient treatment facility and an outpatient treatment facility).

Method step 504 shows the end of the process.

Referring now to FIG. 6, depicted is a high-level logic flowchart depicting an alternate implementation of the process shown in FIG. 5. Method step 600 illustrates that in one implementation, method step 502 is characterized by accepting the user input via an inpatient-outpatient standardized nomenclature. In one implementation, method step 600 entails accepting the medical diagnoses, medical treatments, and medical administrative matters through one or more Graphical User Interfaces (GUIs) via "pick lists" where the medical diagnoses, medical treatments, and medical administrative matters are listed via the inpatient-outpatient standardized nomenclature described above. The remaining method steps function as described elsewhere herein.

Referring now to FIG. 7, illustrated is a graphical user interface depicting an example of the implementation illustrated in method step 600. Method step 700 illustrates that in one implementation, method step 600 is characterized by accepting the user input via a graphical user interface (GUI) having at least one field corresponding to at least one word in the inpatient-outpatient standardized nomenclature. The remaining method steps function as described elsewhere herein. With reference now to FIG. 7A, illustrated is a GUI used in one implementation of method step 600. Shown is an example GUI 750 having a pull-down menu 752 showing a "picklist." Each field in the picklist is =populated with least one word in an inpatient-outpatient standardized nomenclature (e.g., condyloma, vaginal; constipation, Crohn disease, etc.). Those skilled in the art will appreciate that GUI 750 is merely exemplary, and that many other equally serviceable GUI's could be produced in light of the teachings set forth herein.

With reference now to FIGS. 7B–E illustrated are a series of GUIs used in one implementation of method step 600. FIG. 7B depicts a labor and delivery information GUI which is used to acquire labor and delivery information as shown in FIG. 7B (in addition, in one implementation, an automated Narrative Summary culls database information gathered at least in part from the GUI shown in FIG. 7B. FIG. 7C depicts another labor and delivery GUI analogous to FIG. 7A. FIGS. 7D–E shown two GUIs respectively having a procedure and a complication "picklist." Each entry in the picklists of FIGS. 7D–E is populated with least one word in an inpatient-outpatient standardized nomenclature (e.g., amniofusion and bladder injury in FIGS. 7D–E, respectively), which can be added by the health care provider via and pointing and clicking the "add selected procedure for patient" and "add selected complication for patient" GUI buttons. Those skilled in the art will appreciate that the GUIs of FIGS. 7B–E are merely exemplary, and that many other equally serviceable GUI's could be produced in light of the teachings set forth herein.

Referring now to FIG. 8, depicted is a high-level logic flowchart depicting an alternate implementation of the process shown in FIG. 6. Method step 800 illustrates that in one implementation, method step 600 is characterized by accepting the user input from an input device associated with an outpatient facility or accepting the user input from an input associated with an inpatient facility; for example, accepting the user input via the client program 114 running on workstation 112 internal to an outpatient facility as illustrated in FIG. 1, or accepting the user input via the client program 104 running on workstation 102 internal to an inpatient facility as illustrated in FIG. 1, both of which ultimately transmit the user input to the server program 118 running on the minicomputer 116. The remaining method steps function as described elsewhere herein.

In one implementation, the fact that data is accepted into a commonly accessible storage area gives rise to a very useful but unexpected advantage: it will allow "key" information to be culled and displayed across inpatient and outpatient systems, independent of the geographical or organizational location of a person entering data at the inpatient or outpatient location. In addition to the foregoing, it should be noted in passing that in one implementation the ability to segregate the data in outpatient and inpatient records is preserved, which means that inpatient and outpatient facilities can still access their own independent records, should they so desire. Further in addition to the foregoing, the inventors have also discovered that an additional advantage arises in that it makes the "key" inpatient and outpatient data available across both facilities, thereby alleviating the errors and difficulties often associated with a patient's outpatient records not being present in the inpatient facility, and vice versa. An example of a GUI representative of the foregoing appears in FIG. 13A.

D. Providing Outpatient and Inpatient Data Across Outpatient and Inpatient Facilities Referring now to FIG. 9, shown is a high-level logic flowchart depicting a process. Method step 900 shows the start of the process. Method step 902 shows the step of providing both outpatient and inpatient data in response to user input. Method step 904 shows the end of the process.

Referring now to FIG. 10, depicted is a high-level logic flowchart depicting an alternate implementation of the process shown in FIG. 9. Method step 1000 illustrates that in one implementation, method step 902 is characterized by accepting the user input via an inpatient-outpatient standardized nomenclature. The remaining method steps function as described elsewhere herein.

Referring now to FIG. 11, depicted is a high-level logic flowchart depicting an alternate implementation of the process shown in FIG. 9. Method step 1100 illustrates that in one implementation, method step 1000 is characterized by accepting the user input via a graphical user interface having at least one field corresponding to at least one word in the inpatient-out patient standardized nomenclature. The remaining method steps function as described elsewhere herein. An example of a GUIs which might be used in one implementation of method step 1100 appear in the context of FIGS. 7A–E.

Referring now to FIG. 12, depicted is a high-level logic flowchart depicting an alternate implementation of the process shown in FIG. 9. Method step 1200 illustrates that in one implementation, method step 902 is characterized by accepting the user input from an input device, associated with an outpatient facility or accepting the user input from an input device associated with an inpatient facility; for example, accepting the user input via the client program 114 running on workstation 112 internal to an outpatient facility as illustrated in FIG. 1, or accepting the user input via the client program 104 running on workstation 102 internal to an inpatient facility as illustrated in FIG. 1, both of which ultimately transmit the user input to the server program 118 running on the minicomputer 116. The remaining method steps function as described elsewhere herein.

Figure 13A:
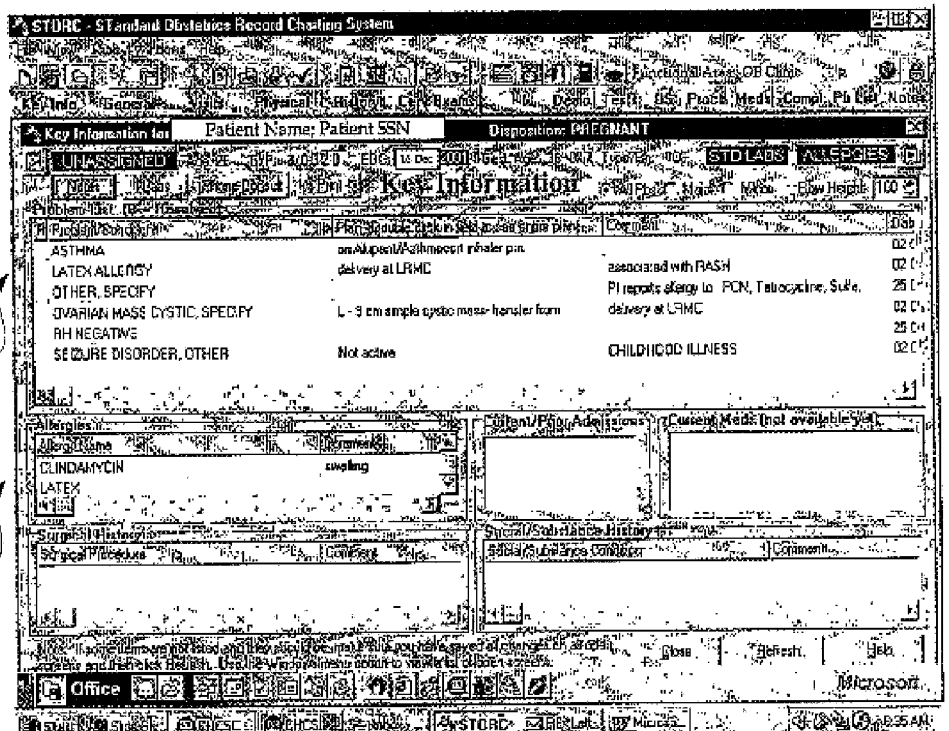

Referring now to FIG. 13, illustrated is a user interface depicting an alternative of the implementation illustrated in method step 902. Method step 1300 shows providing the outpatient and inpatient OB-GYN data via a graphical user interface having at least one field corresponding to aninpatient-outpatient standardized nomenclature. With reference now to FIG. 13A, illustrated is a GUI used in one implementation of method step 1300. Shown is an example GUI 1350, having a key information screen, wherein a "problem/condition" list 1352 and an "allergy" list 1354 are shown. Each field in the "problem/condition" list 1352 is populated with least one word in an inpatient-outpatient standardized nomenclature (e.g., asthma, ovarian mass, cystitic, etc.). Those skilled in the art will appreciate that GUI 1350 is merely exemplary, and that many other equally serviceable GUI's could be produced in light of the teachings set forth herein.

Referring now to FIG. 14, depicted is a high-level logic flowchart depicting an alternate implementation of the process shown in FIG. 13. Method step 1400 illustrates that in one implementation, method step 1300 is characterized by method steps 1400 and 1402. Method step 1400 shows recalling at least one name as categorized as a prior diagnosis. Method step 1402 depicts automatically placing the prior diagnosis in the assessment/diagnosis provision of the note. The remaining method steps function as described elsewhere herein. In one implementation of method steps 1400, 1402, applicable mostly to an inpatient setting, both chronic and acute conditions are automatically recalled and placed in the assessment/diagnosis provision of the note; in another implementation, only chronic conditions are automatically recalled and placed in an assessment/diagnosis provision of a chart note, while any acute conditions must be manually inserted, in the assessment/diagnosis provision of the chart note, by the health care provider during any particular visit. In one implementation, chronic diagnoses and non-chronic diagnoses are predefined. What constitutes a chronic or acute diagnosis varies with the decisions of system designer. With reference now to FIG. 14A, illustrated is a GUI used in one implementation of method step 1402. Shown is an example GUI 1450, having a detailed OB visit information screen, wherein "assessment" list 1452 is shown. Depicted is that a first list member 1454 in the "assessment" list 1452 is populated with a chronic condition (e.g., "latex allergy"), and that a second list member 1456 in the "assessment" list 1452 is populated with an acute condition (e.g., "ROB, uncomplicated"). Those skilled in the art will appreciate that GUI 1450 is merely exemplary, and that many other equally serviceable GUI's could be produced in light of the teachings set forth herein.

Referring now to FIG. 15, depicted is a high-level logic flowchart depicting an alternate implementation of the process shown in FIG. 9. Method step 1500 illustrates that in one implementation, method step 902 is characterized by providing the outpatient and inpatient OB-GYN data via a graphical user interface in either an ad-hoc or a standardized reporting format. The remaining method steps function as described elsewhere herein. With reference now to FIG. 15A, illustrated is a GUI used in one implementation of method step 1500. Shown is an example GUI 1550, having a detailed ad hoc reporting screen 1552 for a particular physician ("Doe, John"). The ad hoc reporting screen 1552, in one implementation, is produced via specifying a physician name, a delivery type, and a date. Those skilled in the art will appreciate that GUI 1550 is merely exemplary, and that many other equally serviceable GUI's could be produced in light of the teachings set forth herein. Referring now to FIG. 15B, shown is a GUI 1570 which depicts a GUI used in another ad hoc reporting screen 1572 implementation of method step 1500. Referring now to FIG. 15C, shown is a GUI 1580 which depicts a GUI used in another ad hoc reporting screen 1582 implementation of method step 1500; ad hoc reporting screen 1582 shows an administrative data implementation in that it lists the outpatient facilities from which inpatients originated (e.g., German cites in which the outpatients were treated). Those skilled in the art will also recognize that ad hoc reporting screens 1552, 1572, 1582 are merely exemplary, and that, in light of the teaching herein, a health care provider could direct a contract programmer to create many other ad hoc reporting screens in light of the teachings herein. What ad hoc reporting screens are to be produced is a design choice within the purview of the health care provider.

Referring now to FIG. 16, depicted is a high-level logic flowchart depicting an alternate implementation of the process shown in FIG. 15. Method step 1600 illustrates that in one implementation, method step 1500 is characterized by providing a report of rates of specific diagnoses, specific procedures, specific complications, or administrative data (e.g., countersignatures not completed, number of patients seen, unfinished discharge notes, etc.) with respect to a specific provider over a range of dates. The remaining method steps function as described elsewhere herein.

Referring now to FIG. 17, illustrated is a graphical user interface depicting an example of the implementation illustrated in method step 15. Method step 1700 illustrates that in one implementation, method step 1500 is characterized by providing clinically-significant data selected from the clinically-significant data group which includes but is not limited to a known allergy, a surgical complication, a social problem, a substance abuse problem, medications, a lab test result, and a previous admission.

In light of the foregoing, the inventors have further posited that the foregoing provides a method and system which allow the smooth and easy transition to common nomenclatures between inpatient and outpatient facilities. The inventors have posited that the foregoing can be accomplished because—insofar as existing record keeping systems are intended to be ultimately related to patient care—it is likely that by focusing on the patient care approach it is probable that the information needed by any form will be captured by the "clinician-driven system, thus allowing the data captured by the system to be "made to look like" or given the "presentation" of any preexisting form. Accordingly, in one implementation of the system described herein, a form-generating engine is used to "repackage" the data so that the data is presented in a fashion which substantially mimics a form used by a treatment facility (e.g., via printing the data such that the data is presented in a fashion which substantially mimics the hardcopy form previously used by a facility). The inventors have speculated that this allows facilities to transition to newer systems without the reluctance which often comes when health care practitioners are told their forms are going to be changed, since many health care providers look for information at certain locations on a printed page, rather than via a field labeling the data.

E. Collecting Countersignatures

Referring now to FIG. 18, shown is a high-level logic flowchart depicting a process. Method step 1800 shows the start of the process. Method step 1802 shows the step of detecting that a first provider note needs a countersignature. Method step 1804 shows the step of presenting the first provider note for second provider countersignature, in response to said detecting. Method step 1806 shows the end of the process. Referring now to FIG. 19, depicted is a high-level logic flowchart depicting alternate implementations of the process shown in FIG. 18. Method step 1900 illustrates that in one implementation, method step 1802 is characterized by detecting that the first provider note is associated with a countersignature required provider; for example, detecting that the person entering the note has an identifier (e.g., a password) associated with an intern status, a resident status, or a nurse practitioner status, or an associated institutional-specific countersignature requirement, or an associated billing-required countersignature requirement. Method step 1902 illustrates that in one implementation, method step 1802 is characterized by detecting that the first provider note has been designated as requiring a countersignature; for example, detecting that another person (e.g., by a nurse practitioner, intern, resident, or physician) has designated the note as needing a countersignature. Method step 1904 illustrates that in one implementation, method step 1802 is characterized by detecting that the first provider note has been designated by the person entering the note as requiring a countersignature; for example, detecting that the person entering the note (e.g., by a nurse practitioner, intern, resident, or physician) has designated the note as needing a countersignature, such as approval by an OB/GYN specialist. With reference now to FIG. 19A, illustrated is a GUI used in one implementation of method step 1902 and in one implementation of method step 1904. Shown is an example GUI 1950, having a progress notes screen, wherein "provider to review note" designator 1952 is shown. Depicted is that the provider to review note is shown as "Doe." In one implementation of method step 1902, the provider entering the note (e.g., a first health care provider, such as a nurse practitioner or resident, is "preidentified" as being a provider needing countersignature, in which case the provider to review note designator 1952 is filled in automatically by the computer program. In one implementation of method step 1904, the provider entering the note (e.g., a first health care provider, such as a nurse practitioner or resident, is NOT "pre-identified" as being a provider needing countersignature, and in such implementation, in which case the provider to review note designator 1952 is filled in by the provider entering the note (e.g., such as when a physician wants "second read" on a note by a colleague or a specialist). Those skilled in the art will appreciate that GUI 1950 is merely exemplary, and that many other equally serviceable GUI's could be produced in light of the teachings set forth herein. The remaining method steps function as described elsewhere herein.

Figure 20A:
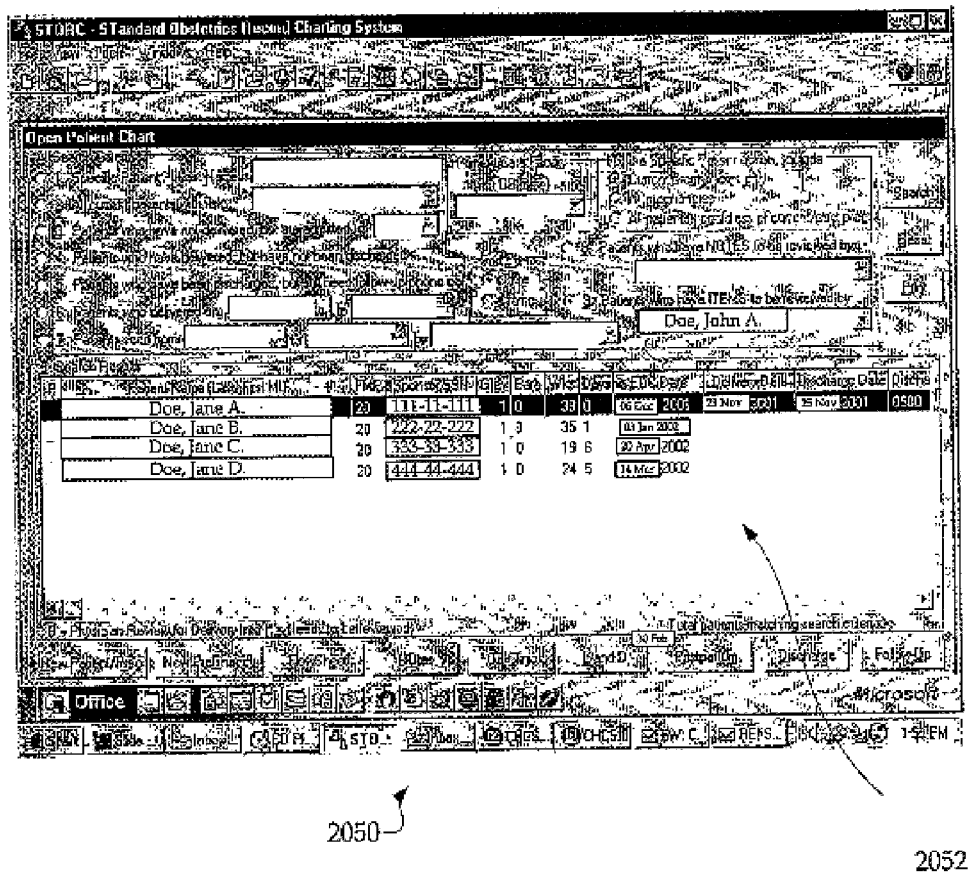

Referring now to FIG. 20, depicted is a high-level logic flowchart depicting an alternate implementation of the process shown in FIG. 18. Method step 2000 illustrates that in one implementation, method step 1804 is characterized by displaying the note to a second provider via a graphical user interface; for example, displaying the note to the second provider for countersignature when the second provider logs onto the client program 104 internal to workstation data processing system 102, which ultimately communicates with the server program 118 running on the minicomputer 116. The remaining method steps function as described elsewhere herein. With reference now to FIG. 20A, illustrated is a GUI used in one implementation of method step 2000. Shown is an example GUI 2050, having a open patient chart screen, wherein "patient notes needing review" list 2052 is shown. Depicted is a "patients who have ITEMS to be reviewed by:" field wherein it is shown that the patient notes appearing in the "patient notes needing review" list 2052 are to be reviewed by the health care provider Doe, and in one implementation is what a health care provider (e.g., Doe) sees when the health care provider first logs in. Those skilled in the art will appreciate that GUI 2050 is merely exemplary, and that many other equally serviceable GUI's could be produced in light of the teachings set forth herein.

Referring now to FIG. 21, depicted is a high-level logic flowchart depicting an alternate implementation of the process shown in FIG. 18. Method step 2100 illustrates that in one implementation, method step 1804 is characterized by accepting the second provider countersignature via a graphical user interface; for example, accepting a graphical signature (e.g., picture of the countersigner's handwritten signature) or a digital signature (e.g., a code known only to the counter signer). The remaining method steps function as described elsewhere herein.

F. Providing A Suggested Course of Treatment

Even the best health care provider can forget, or miss, important details at critical moments during patient care. In addition, the amount of information that health care providers are expected to know is staggering (see, e.g., the roughly 2200 page Cecil's Textbook of Medicine, which is roughly what a general practitioner is expected to know and carry in his or her head).

Unsurprisingly, during the day in and day out operations of medical practice, it is not surprising that health care providers can occasionally forget one or more pages of the tomes that they are expected to carry about in their heads. And when a health care provider forgets such information, the consequences can be devastating.

One example of something a health care provider could easily forget would be to order a genetic screening consult based on the age of the mother. Those having ordinary skill in the art will appreciate that, although this might seem to be a minor thing to forget, it can have devastating consequences to prospective parents in the form of a Down's syndrome child, or the health care provider in terms of a wrongful life suit, which can have extremely high damages awards due to the long-term costs associated with raising and maintaining a disabled individual. As another, related, example, it is possible that the health care provider could forget to obtain the results of a genetic screening consult that had previously been ordered. This, too, could cause similar difficulties.

Accordingly, it is apparent that a need exists for a method and system which will augment the memories and/or practices of health care providers.

Referring now to FIG. 22, shown is a high-level logic flowchart depicting a process. Method step 2200 shows the start of the process. Method step 2204 shows the step of presenting a specific treatment recommendation, in response to detecting a first event; for example, detecting a condition which has been entered as an OB/GYN note in an OB/GYN patient's chart. Method step 2206 shows the end of the process. With reference now to FIG. 22A-C, illustrated are three different GUIs used in three different implementations of method step 2204. FIG. 22A shows an example GUI 2250 having a gestational age field 2252, wherein is shown standard plan overview field 2254, which in one implementation identifies the plan (e.g., "a standard plan for 15–19 wks is shown"), who authorized the plan (e.g., health care provider "jdoe"), and the date the plan was authorized (e.g., 16 Oct. 2001); and further wherein is shown a patient-specific plan field 2256, which in one implementation gives the details of the plan identified in the standard plan overview field 2254 as well as any additional plan specific to the patient which may have been entered, free text, by a health care provider. FIGS. 22B–C are substantially analogous to FIG. 22A except for respectively depicting plans for gestational age 28 to 36 weeks and gestational age greater than 41 weeks. Those skilled in the art will appreciate that GUI 2250 is merely exemplary, and that many other equally serviceable GUI's could be produced in light of the teachings set forth herein.

Referring now to FIG. 23, depicted is a high-level logic flowchart depicting an alternate implementation of the process shown in FIG. 22. Illustrated is that, in one implementation, method step 2204 is characterized by method step 2300, 2302, and 2304. Method step 2300 shows detecting that the age of a patient, at an expected time of delivery, is greater than or equal to a predefined age at time of delivery; for example, detecting that the patient will be greater than 34 years of age at the expected time of delivery. Method step 2302 depicts determining a first provider classification; for example, determining the first provider classification to be a family physician or an OB/GYN physician (e.g., via a previously entered password the health care provider entering a note). Method step 2304 illustrates recommending consultation in response to the first provider classification and the age of the patient; for example, recommending (e.g., via a display on a graphical user interface) to a family physician treating a patient who will be over 34 at the time of the expected delivery of her baby that the patient be referred for a genetic counseling consult, thereby ensuring that the first provider (e.g., the family physician or OB/GYN physician) meets the reasonably prudent practitioner standard (thereby providing the industry-standard of care and thereby substantially immunizing the practitioner from a lawsuit for failing to identify the issue and make the referral). The remaining method steps function as described elsewhere herein.

Referring now to FIG. 24, depicted is a high-level logic flowchart depicting an alternate implementation of the process shown in FIG. 22. Illustrated is that, in one implementation, method step 2204 is characterized by method step 2400, and 2402. Method step 2400 shows detecting a gestational age between a first date and a second date gestation; for example, detecting that the gestational age of the patient's fetus is between 15–20 weeks. Method step 2402 depicts recommending a specific course of treatment in response to said detecting the gestational age; for example, recommending multiple marker serum analyte screening test, thereby ensuring that the first provider (e.g., the family physician or OB/GYN physician) meets the reasonably prudent practitioner standard (e.g. thereby providing the industry-standard of care and thereby substantially immunizing the practitioner from a lawsuit for failing to identify the issue and make the referral). The remaining method steps function as described elsewhere herein.

Referring now to FIG. 25, depicted is a high-level logic flowchart depicting an alternate implementation of the process shown in FIG. 22. Illustrated is that, in one implementation, method step 2204 is characterized by method step 2500, and 2502. Method step 2500 shows detecting a specific diagnosis; for example, detecting that the patient has gestational diabetes or that the patient has had an abnormal Pap smear result. Method step 2502 depicts recommending a specific course of treatment in response to said detecting the specific diagnosis; for example, recommending dietary consultation and/or glucose monitoring, and/or a colposcopy, as appropriate, thereby ensuring that the first provider (e.g., the family physician or OB/GYN physician) meets the reasonably prudent practitioner standard (e.g., thereby providing the industry-standard of care and thereby substantially immunizing the practitioner from a lawsuit for failing to identify the issue and make the referral). The remaining method steps function as described elsewhere herein.

Referring now to FIG. 26, depicted is a high-level logic flowchart depicting an alternate implementation of the process shown in FIG. 22. Illustrated is that, in one implementation, the process shown in FIG. 22 entails an additional method step 2600. Method step 2600 illustrates suspending operation until a response to the specific treatment recommendation has been received; for example, a computer interface not allowing data entry unless and until the treating physician attempting to enter a note either actively declines the recommended treatment or accepts and recommends the treatment. The remaining method steps function as described elsewhere herein. With reference now to FIG. 26A, illustrated is a GUI used in one implementation of method step 2600. Shown is an example GUI 2650, having a "force plan acceptance or rejection" screen 2652. Depicted is a specific "GBS Prophylaxis" instance of the "force plan acceptance or rejection" screen 2652. As shown, the "force plan acceptance or rejection" screen 2652 alerts the health care provider that specific criteria have been met which indicate a specific plan of treatment (e.g., GBS prophylaxis), and the "force plan acceptance or rejection" screen 2652 gives the health care provider the forced option of either adding the plan or rejecting the plan, in the absence of which the GUI will allow no further entry of data; in addition, further shown is that, in one implementation, should the health care provider refuse to add the treatment plan, he or she is forced to give a reason why. Those skilled in the art will appreciate that GUI 2650 is merely exemplary, and that many other equally serviceable GUI's could be produced in light of the teachings set forth herein.

Referring now to FIG. 27, depicted is a high-level logic flowchart depicting alternate implementations of the process shown in FIG. 26. Illustrated is that, in one implementation, method step 2600 is characterized by method step 2700. Method step 2700 shows suspending operation until a response to suggested genetic counseling has been received; for example, in the case where the mother will be over age 34 at the time of delivery, a computer interface refusing further data entry by a physician unless and until the physician either requests a genetic counseling consult or actively declines requesting the genetic counseling consult. Illustrated is that, in another implementation, method step 2600 is characterized by method step 2702. Method step 2702 depicts suspending operation until a response to suggested colposcopy has been received; for example, in the case where the mother has an abnormal Pap smear, a computer interface refusing further data entry by a physician unless and until the physician either requests a colposcopy consult or actively declines such requesting the colposcopy consult. The remaining method steps function as described elsewhere herein.

Referring now to FIG. 28, depicted is a high-level logic flowchart depicting a process. Method step 2800 shows the start of the process. Method step 2802 illustrates detecting a previously accepted specific treatment recommendation, in response to attempted note entry (and, in some implementations, entails a recognition of the identity of the provider entering the note); for example, when a physician attempts to enter a chart note for a particular patient, the client program 104 running internal to workstation data processing system 102 communicates with the server program 118 running internal to the minicomputer 116 and detects that a previously recommended course of medical treatment (e.g., genetic consultation, multiple marker serum analyte screening test, or colposcopy) has been previously accepted for the particular patient. Method step 2804 shows presenting to the provider at least one question asking whether the previously accepted specific treatment recommendation has been completed; for example, when genetic counseling, or multiple marker serum analyte screening test, or a colposcopy has been previously recommended (e.g., as discussed in relation to FIGS. 22, 23, 24, and 25), the health care provider is presented with a question as to whether the results of the genetic counseling, or the multiple marker serum analyte screening test, or the colposcopy have been yet obtained. Method step 2806 illustrates the end of the process.

Referring now to FIG. 29, depicted is a high-level logic flowchart depicting an alternate implementation of the process shown in FIG. 28. Illustrated is that, in one implementation, method step 2800 is characterized by method step 2900. Method step 2900 shows detecting a previous recommendation of genetic counseling, or a previous recommendation of a multiple marker serum analyte screening test, or a previous recommendation for colposcopy, or a previous recommendation for diabetes screening. The remaining method steps function as described elsewhere herein.

Referring now to FIG. 30, depicted is a high-level logic flowchart depicting alternate implementations of the process shown in FIG. 28. Illustrated is that, in one implementation, method step 2804 is characterized by method step 3000. Method step 3000 shows repetitively presenting to the provider the at least one question asking whether the previously accepted specific treatment recommendation has been completed until the provider either confirms completion or dismisses the at least one question. The remaining method steps function as described elsewhere herein.

G. Providing For Automated Note Completion

In some contexts, health care providers can be very busy. In such situations, it is not uncommon for the health care providers to sometimes forget to complete their notes or charts. Those having ordinary skill in the art will appreciate that in some instances such failure to complete the notes and charts could prove deleterious, for various reasons.

Referring now to FIG. 31, shown is a high-level logic flowchart depicting a process. Method step 3100 shows the start of the process. Method step 3102 shows the step of sensing a presence of a first provider; for example, sensing that the at least one provider has logged onto the server program 118 running internal to the minicomputer 116 using a known password. Method step 3104 shows the step of detecting at least one incomplete provider note; for example, checking at least one database for flagged-incomplete notes associated with the first provider. Method step 3106 shows the step of presenting the at least one incomplete provider note to the first provider. Method step 3108 shows the additional alternate step of accepting additional text from the first provider. Method step 3110 shows the end of the process.

Referring now to FIG. 32, depicted is a high-level logic flowchart depicting an alternate implementation of the process shown in FIG. 31. Illustrated is that, in one implementation, method step 3102 is characterized by method step 3200. Method step 3200 shows accepting an identifier associated with the first provider; for example, accepting user input of the identifier via either a keyboard, a touch-screen reader, a graphical user interface, or a biometrics identifier. The remaining method steps function as described elsewhere herein.

H. Providing Automated Discharge Summary Narration

Those having ordinary skill in the art will appreciate that one of the most tedious and time consuming tasks an inpatient health care provider must perform is the creation and finalization of the Discharge Narrative Summary ("Narsum"). In the absence of the present invention, upon discharge the primary health care provider—generally after a long and demanding day treating patients—retires to his or her office with the charts of his or her discharged patients. Thereafter, with the chart(s) in one hand and a Dictaphone in the other, the health care provider proceeds to dictate a "narrative summary" of each discharged patient's progression, diagnosis, and treatment during his or her inpatient admission. Those skilled in the art will recognize that, in the absence of the present invention, the way in which Narsums are created in the related art is both tedious and fraught with chance of error. It is therefore apparent that a need exists for a method and system which provide an automated Discharge Summary Narration.

Referring now to FIG. 33, shown is a high-level logic flowchart depicting a process. Method step 3300 shows the start of the process. Method step 3302 shows the step of providing automated discharge summary narration; for example, upon user input, a computer program (e.g., the client program 104 running on a workstation computer system processing system 102 communicating with the server program 118 to automatically print a document labeled Narrative Summary which contains a listing of treatments and diagnoses for a patient made between the date of the patient's admission and discharge, as well as chronic conditions of the patient. In one implementation, the foregoing is achieved via providing at least one treatment-identifier selected from the treatment-identifier group including but not limited to a procedure, a diagnosis, a date of admission, a date of discharge, and a brief clinical course overview (where the brief clinical course overview may be entered via free-text form). Method step 3304 shows the end of the process.

The diagnosis in the treatment-identifier group can be either chronic condition or a current condition. A specific example of a current condition would be acute pyelonephritis (a kidney infection), which is a condition a patient has contracts and is subsequently cured of in a relatively short time frame. In contrast, an example of a chronic condition would be diabetes which is to be managed over a relatively long time frame, rather than cured over a relatively short time frame. Those skilled in the art will recognized that one advantage of having chronic conditions listed on the Narsum is that it increases the likelihood that health care providers will receive increased reimbursement, available under some contracts, for treatment of a patient having a chronic condition.

Those having ordinary skill in the art will appreciate that there is a myriad of different information that may be present in a Narrative Summary. The information present is a design choice within the purview of the health care provider.

With reference now to FIGS. 33A–E, shown are a series of GUIs used in various implementations of method step 3320. FIG. 33A depicts a GUI showing a "discharge information" discharge summary wherein are illustrated "discharge date," "prior admissions," "reasons for admission," "final diagnosis summary," and "procedures performed" listings. FIG. 33B depicts a GUI showing a "findings from admission" discharge summary wherein is illustrated a "significant findings from admission" listing. FIG. 33C depicts a GUI showing a "findings from history" discharge summary wherein is illustrated a "significant/chronic findings from history" listing. FIG. 33D depicts a GUI showing a "patient instructions" discharge summary wherein are illustrated "discharge medications," "other instructions," "limitations on activities," "diet," and "return to facility/clinic" listings; insofar as the discharge medications and other instructions listings are often loaded automatically, FIG. 33D also constitutes another example of an automated plan of treatment. Lastly, FIG. 33E depicts a GUI showing a "discharge comments" discharge summary wherein a health care provider can enter his or her comments free text. Those skilled in the art will appreciate that GUIs of FIGS. 33A–E are merely exemplary, and that many other equally serviceable GUI's could be produced in light of the teachings set forth herein.

Referring now to FIG. 34, depicted is a high-level logic flowchart depicting an alternate implementation of the process shown in FIG. 33. Illustrated is that, in one implementation, method step 3302 is characterized by method step 3400. Method step 3400 shows querying a database having either an inpatient or outpatient note. The remaining method steps function as described elsewhere herein.

Those having ordinary skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having ordinary skill in the art will appreciate that there are various vehicles by which processes and/or systems described herein can be effected (e.g., hardware, software, and/or firmware), and that the preferred vehicle will vary with the context in which the processes are deployed. For example, if an implementer determines that speed and accuracy are paramount, the implementer may opt for a hardware and/or firmware vehicle; alternatively, if flexibility is paramount, the implementer may opt for a solely software implementation; or, yet again alternatively, the implementer may opt for some combination of hardware, software, and/or firmware. Hence, there are several possible vehicles by which the processes described herein: may be effected, none of which is inherently superior to the other in that any vehicle to be utilized is a choice dependent upon the context in which the vehicle will be deployed and the specific concerns (e.g., speed, flexibility, or predictability) of the implementer, any of which may vary.

The foregoing detailed description has set forth various embodiments of the devices and/or processes via the use of block diagrams, flowcharts, and examples. Insofar as such block diagrams, flowcharts, and examples contain one or more functions and/or operations, it will be understood as notorious by those within the art that each function and/or operation within such block diagrams, flowcharts, or examples can be implemented, individually and/or collectively, by a wide range of hardware, software, firmware, or virtually any combination thereof. In one embodiment, the present invention may be implemented via Application Specific Integrated Circuits (ASICs). However, those skilled in the art will recognize that the embodiments disclosed herein, in whole or in part, can be equivalently implemented in standard Integrated Circuits, as one or more computer programs running on one or more computers (e.g., as one or more programs running on one or more data processing systems), as one or more programs running on one or more controllers (e.g., microcontrollers) as one or more programs running on one or more processors e.g., microprocessors, as firmware, or as virtually any combination thereof, and that designing the circuitry and/or writing the code for the software and or firmware would be well within the skill of one of ordinary skill in the art in light of this disclosure. In addition, those skilled in the art will appreciate that the mechanisms of the present invention are capable of being distributed as a program product in a variety of forms, and that an illustrative embodiment of the present invention applies equally regardless of the particular type of signal bearing media used to actually carry out the distribution. Examples of signal bearing media include, but are not limited to, the following: recordable type media such as floppy disks, hard disk drives, CD ROMs, digital tape, and computer memory; and transmission type media such as digital and analogue communication links using TDM or IP based communication links (e.g., packet links).

In a general sense, those skilled in the art will recognize that the various embodiments described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and electrical circuitry forming a communications device (e.g., a modem, communications switch, or optical-electrical equipment).

Those skilled in the art will recognize that it is common within the art to describe devices and/or processes in the fashion set forth herein, and thereafter use standard engineering practices to integrate such described devices and/or processes into data processing systems. That is, the devices and/or processes described herein can be integrated into a data processing system via a reasonable amount of experimentation.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. Note: it will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

What is claimed is:

1. A method comprising:

sensing a presence of a first provider;

detecting at least one incomplete provider note; and presenting the at least one incomplete provider note to the first provider.

2. The method of claim 1, wherein said sensing a presence of a first provider comprises:

accepting an identifier associated with the first provider.

3. The method of claim 2, wherein said accepting an identifier associated with the first provider comprises:

accepting user input of the identifier via either a keyboard, a touch-screen reader, a graphical user interface, or a biometrics identifier.

4. The method of claim 1, wherein said detecting at least one incomplete provider note comprises:

checking at least one database for flagged-incomplete notes associated with the at least one provider.

5. The method of claim 1, further comprising:

accepting additional text from the first provider.

6. A system comprising:

means for sensing a presence of a first provider;

means for detecting at least one incomplete provider note; and means for presenting the at least one incomplete provider note to the first provider.

7. The system of claim 6, wherein said means for sensing a presence of a first provider comprises:

means for accepting an identifier associated with the first provider.

8. The system of claim 7, wherein said means for accepting an identifier associated with the first provider comprises:

means for accepting user input of the identifier via either a keyboard, a touch-screen reader, a graphical user interface, or a biometrics identifier.

9. The system of claim 6, wherein said means for detecting at least one incomplete provider note comprises:

means for checking at least one database for flagged-incomplete notes associated with the at least one provider.

10. The system of claim 1, further comprising:

means for accepting additional text from the first provider.

* * * * *